(12) United States Patent
Matsui et al.

(10) Patent No.: US 6,468,606 B1
(45) Date of Patent: *Oct. 22, 2002

(54) PHENYLBENZOATE DERIVATIVES AND LIQUID CRYSTAL COMPOSITIONS

(75) Inventors: Shuichi Matsui; Tomoyuki Kondo; Kazutoshi Miyazawa, all of Ichihara; Noriyuki Ohnishi, Tsukuba; Yasuyuki Goto, Ichihara; Etsuo Nakagawa, Ichihara; Shinichi Sawada, Ichihara, all of (JP)

(73) Assignee: Chisso Corporation, Osaka (JP)

( * ) Notice: Subject to any disclaimer, the term of this patent is extended or adjusted under 35 U.S.C. 154(b) by 57 days.

This patent is subject to a terminal disclaimer.

(21) Appl. No.: 09/234,318

(22) Filed: Jan. 21, 1999

Related U.S. Application Data

(63) Continuation of application No. 08/875,995, filed as application No. PCT/JP96/00256 on Feb. 7, 1996, now Pat. No. 5,922,243.

(30) Foreign Application Priority Data

Feb. 9, 1995 (JP) ................................................ 7-46353
Jun. 27, 1995 (JP) ............................................. 7-184933

(51) Int. Cl.$^7$ ..................... C09K 19/30; C09K 19/20; C07C 69/78; C07C 25/13
(52) U.S. Cl. .............. 428/1.1; 252/299.63; 252/299.67; 560/65; 570/127; 570/129; 570/130
(58) Field of Search .................. 252/299.01, 299.67, 252/299.63; 570/127, 129, 130; 428/1.1; 560/65

(56) References Cited

U.S. PATENT DOCUMENTS

| | | | |
|---|---|---|---|
| 4,405,488 A | 9/1983 | Sugimori et al. | 252/299.63 |
| 5,324,449 A | 6/1994 | Kumeier et al. | 252/299.01 |
| 5,725,799 A | 3/1998 | Bremer et al. | 252/299.67 |
| 5,855,814 A | 1/1999 | Matsui et al. | 252/299.67 |
| 5,922,243 A * | 7/1999 | Matsui et al. | 252/299.67 |

FOREIGN PATENT DOCUMENTS

| | | |
|---|---|---|
| JP | 1 68659 | 7/1989 |
| JP | 2-233626 | 9/1990 |
| JP | 6-220454 | 8/1994 |
| JP | 6-248268 | 9/1994 |
| JP | 6-316540 | 11/1994 |
| JP | 7-316082 | 12/1995 |
| WO | WO 92/05230 | 4/1992 |
| WO | WO 9426838 | 11/1994 |

OTHER PUBLICATIONS

"Reactions of Grignard reagents with peroxy compounds", S.O. Lawesson, et al, (19590 4230–4233, vol. 81.
"Phenols:6–Methoxy–2–Naphthol", Organic Synthesis, pp. 918–921, 1973.

* cited by examiner

Primary Examiner—Shean C. Wu
(74) Attorney, Agent, or Firm—Oblon, Spivak, McClelland, Maier & Neustadt, P.C.

(57) ABSTRACT

A liquid crystal composition which comprises at least one phenylbenzoate derivative represented by formula (1)

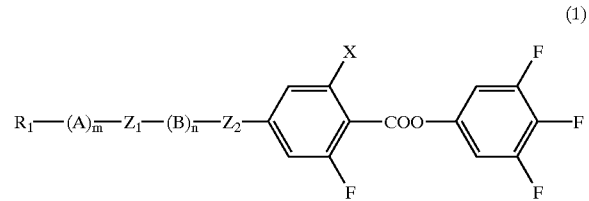

wherein $R_1$ is a hydrogen atom or an alkyl group of 1–10 carbons and others; X is a hydrogen atom or a halogen atom; A and B each independently represent a 1,4-phenylene group or a trans-1,4-cyclohexylene group and others; $Z_1$ and $Z_2$ each independently represent —$CH_2CH_2$—, —CO—O—, a covalent bond and others; m and n each independently represent 0 or 1.

16 Claims, No Drawings

PHENYLBENZOATE DERIVATIVES AND LIQUID CRYSTAL COMPOSITIONS

This is a continuation of Ser. No. 08/875,995 filed Aug. 11, 1997 now U.S. Pat. No. 5,922,243 which is a 371 PCT/JP96/00256 filed Feb. 7, 1996.

TECHNICAL FIELD

This invention relates to a novel liquid crystalline compound which can demonstrate favorable properties principally in a twisted nematic liquid crystal composition and a liquid crystal composition having favorable properties using said novel liquid crystalline compound.

BACKGROUND ART

A liquid crystal display element utilizes an optical anisotropy and a dielectric anisotropy which a liquid crystalline material possesses. As a display mode therefor, there are known a twisted nematic mode (TN), a super twisted nematic mode (STN), a dynamic scattering mode (DS), a guest-host mode (G-H), DAP mode and others. As a driving mode therefor, there are known a static-driving mode, a time-sharing driving mode, an active-matrix driving mode, a dual frequency driving mode and others. The properties of liquid crystalline materials used for these various liquid crystal display elements vary depending on the application of the elements, but liquid crystalline materials are required to be stable to external environmental factors such as moisture, air, heat, light, etc. and to show a liquid crystal phase over a wide temperature range around room temperature, with a lower viscosity and a lower driving voltage. In addition, a liquid crystalline material generally used for a liquid crystal display element is composed of several to twenty liquid crystalline compounds for providing the optimum dielectric anisotropy ($\Delta\epsilon$) or optical anisotropy ($\Delta n$) which is required for individual display elements. In view of this, there has been required a compatibility with other liquid crystalline compounds, particularly in recent years, a good low-temperature compatibility from the demand for application under various environments.

A liquid crystalline compound having as a substituent a fluorine atom at the end generally shows a lower dielectric anisotropy ($\Delta\epsilon$) and optical anisotropy ($\Delta n$) as compared with a compound having a cyano group as a substituent, but has a remarkably superior chemical stability to that of the cyano-substituted compound and is considered to cause a less production of ionic impurities due to a change with time. Therefore, the fluorine-containing compounds have been actively used for various modes including an active-matrix mode. The recent trend of development in this field is directed to making a small-sized liquid crystal element including a portable TV and lowering in driving voltage in compliance with the demand for a lower voltage. In order to achieve this object, the development of a compound having a high dielectric anisotropy ($\Delta\epsilon$) is active.

In order to increase a dielectric anisotropy ($\Delta\epsilon$) in the fluorine-containing compound, it is effective to increase the substitution number of a fluorine atom, which is a procedure usually carried out by those skilled in the art. However, it has been empirically realized by those skilled in the art that there is a proportional relationship between the substitution number of a fluorine atom and the viscosity of the compound, and further that there is an inverse relationship between the substitution number of a fluorine atom and the temperature range of a liquid crystal phase. Accordingly, it has been considered to be difficult to improve a dielectric anisotropy ($\Delta\epsilon$) only, while inhibiting an increase in the viscosity and a reduction in the temperature range of a liquid crystal phase. As an example of the compounds multi-substituted with fluorine atoms, those having the following structure are disclosed.

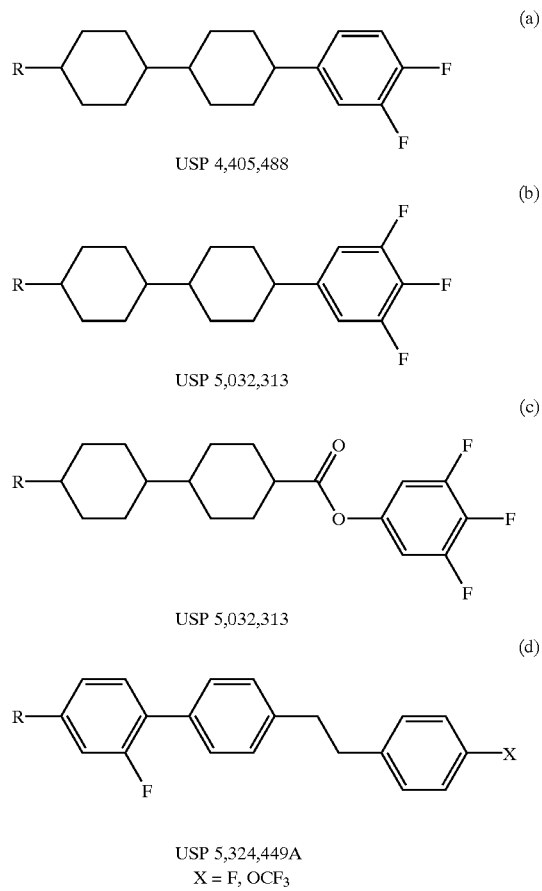

The dielectric anisotropy values ($\Delta\epsilon$) of the compounds (a), (b) and (c) are high in the order of (c)>(b)>(a). However, the compound (c) is not appreciably good in respect of a compatibility with other liquid crystalline compounds, especially, a low temperature compatibility. On the other hand, the compound (d) shows an example wherein a fluorine atom is laterally substituted on the phenyl ring to which R is attached, but this compound is not so appreciably good in respect of compatibility.

DISCLOSURE OF INVENTION

It is an object of this invention to provide a novel liquid crystalline compound having a relatively low viscosity, a high dielectric anisotropy, a low optical anisotropy and an excellent compatibility with other known liquid crystalline compounds, in particular, an excellent low temperature compatibility, and a liquid crystal composition containing the same.

We have investigated various compounds in an effort to solve the aforesaid problems and found as a liquid crystalline compound with a high dielectric anisotropy, a compound having a phenylbenzoate moiety and a fluorine atom substituted at the ortho-position to the ester carbonyl group. As a result of further study of its physical properties, it has been found that the fluorine atom substituted at the ortho-position to the ester carbonyl group of the phenylbenzoate moiety can serve to improve the viscosity and suppress a reduction in a temperature range of a liquid crystal phase and to exhibit an extremely higher dielectric anisotropy than that as we initially expected and further to accomplish a remarkable effect on improvement in a compatibility with other liquid crystalline compounds, in particular, in a low temperature compatibility, which leads to the completion of the present invention directed to a novel liquid crystalline material.

In the first aspect, the invention relates to phenylbenzoate derivatives represented by formula (1)

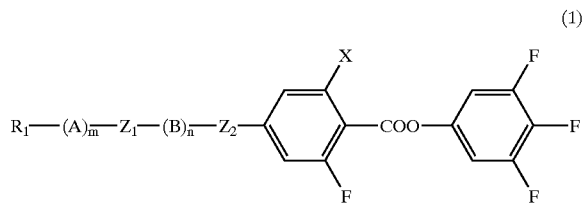

(1)

wherein $R_1$ is a hydrogen atom or a straight or branched-chain alkyl group of 1–10 carbons, one or two non-adjacent $CH_2$ groups of which can be replaced by an oxygen atom or a group of —CH=CH—; X is a hydrogen atom or a halogen atom; A and B each independently represent a 1,4-phenylene group or a trans-1,4-cyclohexylene group, which may be substituted by one or more halogen atoms; $Z_1$ and $Z_2$ each independently represent —$CH_2CH_2$—, —CO—O—, —O—CO—, —CH=CH—, —C≡C—, —$(CH_2)_4$— or a covalent bond; m and n each independently represent 0 or 1.

Where $R_1$ in formula (1) is a group other than a hydrogen atom, the following groups are included as specific groups.

Where $R_1$ is a straight-chain group, it includes an alkyl group of 1–10 carbons, an alkoxy group of 1–9 carbons, an alkoxyalkyl group of 2–9 carbons, an alkoxyalkoxy group of 2–8 carbons, an alkenyl group of 2–11 carbons, an alkenyloxy group of 2–10 carbons, an alkenyloxyalkyl group of 3–10 carbons and an alkoxyalkenyl group of 3–10 carbons.

Where $R_1$ is a branched-chain group, it includes an alkyl group of 3–10 carbons, an alkoxy group of 3–9 carbons, an alkoxyalkyl group of 4–9 carbons, an alkoxyalkoxy group of 4–8 carbons, an alkenyl group of 3–11 carbons, an alkenyloxy group of 3–10 carbons, an alkenyloxyalkyl group of 4–10 carbons and an alkoxyalkenyl group of 4–10 carbons.

Where $R_1$ is a branched-chain group, in particular, an optically active group, the corresponding compound can be used as an additive to induce a twisted structure in a nematic liquid phase or as a component for a chiral smectic liquid crystal having a ferroelectricity.

One preferred embodiment in the first aspect of this invention is a phenylbenzoate derivative of formula (1) wherein m=n=0, both $Z_1$ and $Z_2$ are a covalent bond.

Another preferred embodiment in the first aspect of this invention is a phenylbenzoate derivative of formula (1) wherein m=1, n=0, either of $Z_1$ and $Z_2$ is a covalent bond, A is a trans-1,4-cyclohexylene group.

A still another preferred embodiment in the first aspect of this invention is a phenylbenzoate derivative of formula (1) wherein m=1, n=0, either of $Z_1$ and $Z_2$ is a covalent bond, A is a 1,4-phenylene group.

A still another preferred embodiment in the first aspect of this invention is a phenylbenzoate derivative of formula (1) wherein m=1, n=1, and A and B each are a trans-1,4-cyclohexylene group.

A still another preferred embodiment in the first aspect of this invention is a phenylbenzoate derivative of formula (1) wherein m=1, n=1, and A is a trans-1,4-cyclohexylene group and B is a 1,4-phenylene group.

A still another preferred embodiment in the first aspect of this invention is a phenylbenzoate derivative of formula (1) wherein m=1, n=1, and A is a 1,4-phenylene group and B is a trans-1,4-cyclohexylene group.

A still another preferred embodiment in the first aspect of this invention is a phenylbenzoate derivative of formula (1) wherein m=1, n=1, and A and B each are a 1,4-phenylene group.

In the second aspect, the invention relates to liquid crystal compositions composed of at least two components, which comprise at least one phenylbenzoate derivative represented by formula (1) as defined in the first aspect of this invention.

One preferred embodiment in the second aspect of this invention is a liquid crystal composition which comprises as a first component at least one of the phenylbenzoate derivatives represented by formula (1) as defined in the first aspect of this invention and as a second component one or more compounds selected from the group consisting of the compounds of formulae (2), (3) and (4)

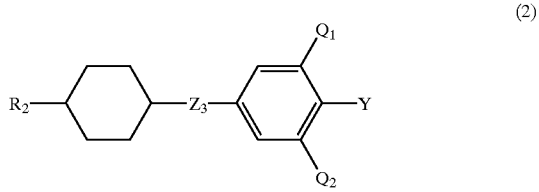

(2)

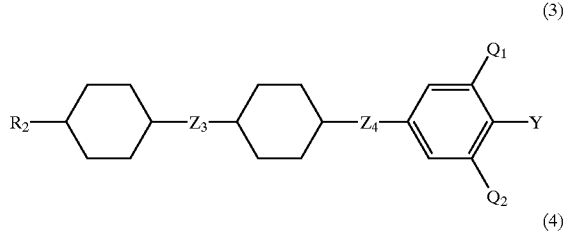

(3)

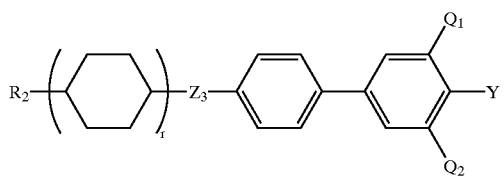

(4)

wherein $R_2$ is an alkyl group of 1–10 carbons, Y is F or Cl, $Q_1$, and $Q_2$ each independently represent H or F, r is 1 or 2, and $Z_3$ and $Z_4$ each independently represent —$CH_2CH_2$— or a covalent bond.

An another preferred embodiment in the second aspect of this invention is a liquid crystal composition which comprises as a first component at least one phenylbenzoate derivative of formula (1) as defined in the first aspect of this invention and as a second component one or more compounds selected from the group consisting of the compounds of formulae (5), (6), (7), (8) and (9)

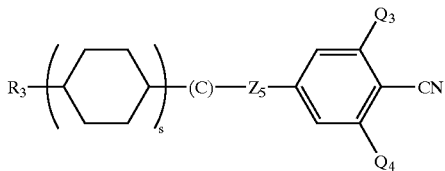
(5)

wherein $R_3$ is an alkyl group of 1–10 carbons or an alkenyl group of 2–10 carbons. In any case, an optional methylene group (—CH$_2$—) may be replaced by an oxygen atom (—O—), but two or more methylene groups are not consecutively replaced by an oxygen atom, $Z_5$ is —CH$_2$CH$_2$—, —COO— or a covalent bond, $Q_3$ and $Q_4$ represent H or F, C stands for a cyclohexane ring, a benzene ring or a 1,3-dioxane ring, and s is 0 or 1,

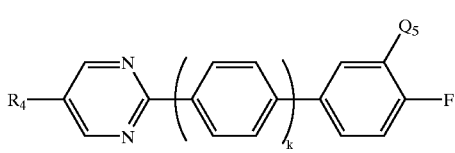
(6)

wherein $R_4$ is an alkyl group of 1–10 carbons, $Q_5$ represents H or F, and k is 0 or 1,

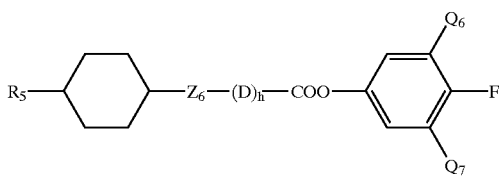
(7)

wherein $R_5$ is an alkyl group of 1–10 carbons, D stands for a cyclohexane ring or a benzene ring, $Q_6$ and $Q_7$ each independently represent H or F, $Z_6$ is —COO— or a covalent bond, and h is 0 or 1,

(8)

wherein $R_6$ and $R_7$ each independently represent an alkyl, an alkyloxy or alkyloxymethyl group of 1–10 carbons, E stands for a cyclohexane ring, a pyrimidine ring or a benzene ring, F stands for a cyclohexane ring or a benzene ring, and $Z_7$ is (—C≡C—), —COO—, —CH$_2$CH$_2$—or a covalent bond,

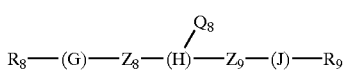
(9)

wherein $R_8$ is an alkyl or alkyloxy group of 1–10 carbons, $R_9$ is an alkyl, alkyloxy or alkyloxymethyl group of 1–10 carbons, G stands for a cyclohexane ring or a pyrimidine ring, H and J each independently represent a cyclohexane ring or a benzene ring, $Z_8$ is —COO—, —CH$_2$CH$_2$—or a covalent bond, $Z_9$ is —C≡C—, —COO— or a covalent bond, and $Q_8$ is H or F.

In the third aspect, the invention relates to a liquid crystal display element using a liquid crystal composition comprising at least two components, which comprises at least one phenylbenzoate derivative represented by formula (1) as defined in the first aspect of this invention.

A preferred embodiment of the liquid crystal composition used in the third aspect of this invention is a liquid crystal composition described in any embodiments of the second aspect of this invention.

Examples of the preferred embodiments of the phenylbenzoate derivatives represented by formula (1) in the first aspect of this invention include the compounds represented by the following formulae (1-a)–(1-g).

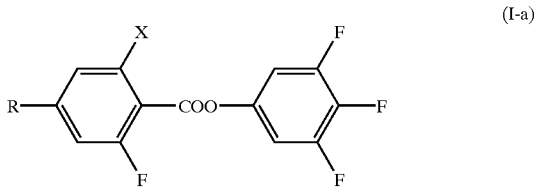
(I-a)

(I-b)

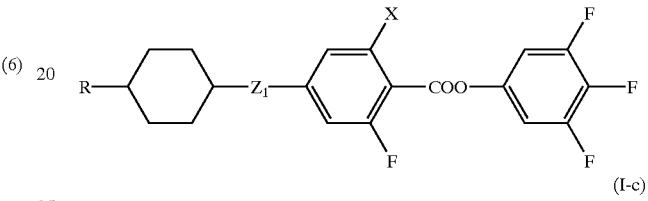
(I-c)

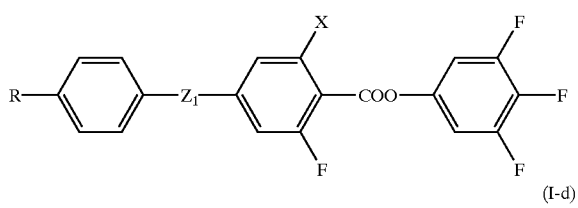
(I-d)

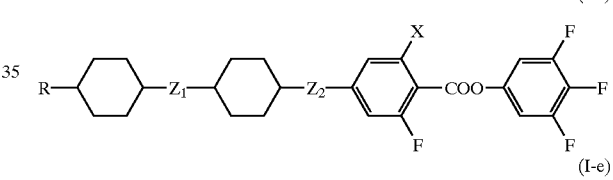
(I-e)

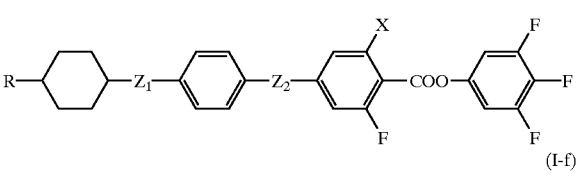
(I-f)

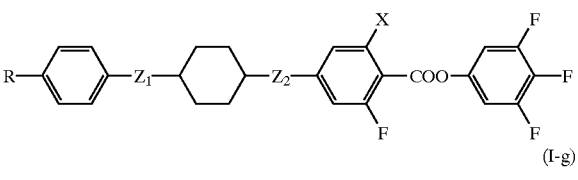
(I-g)

wherein R is a hydrogen atom or a straight or branched-chain alkyl group of 1–9 carbons, one or two non-adjacent CH$_2$ groups of which may be replaced by an oxygen atom or —CH=CH—group, X is a hydrogen atom or a halogen atom, $Z_1$ and $Z_2$ each independently are —CH$_2$CH$_2$—, —CO—O—, —O—CO—, —CH=CH—, —C≡C— or a covalent bond.

Preferred compounds of formula (1-b) are more specifically referred to by the following compounds.

(I-b-1)
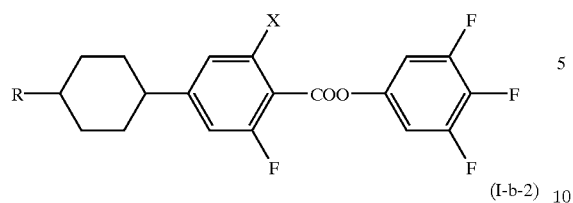

(I-b-2)
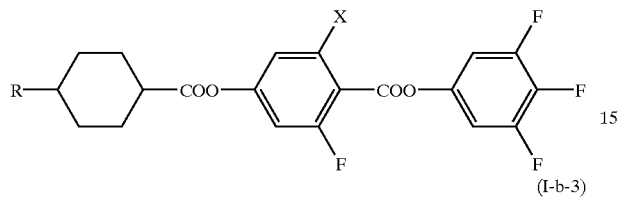

(I-b-3)
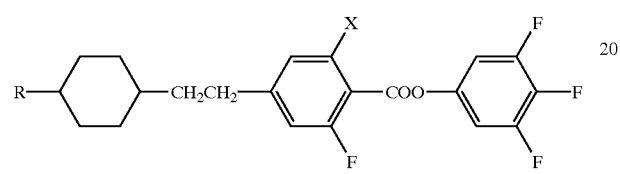

wherein R is a hydrogen atom or a straight or branched-chain alkyl group of 1–9 carbons, one or two non-adjacent CH$_2$ groups of which may be replaced by an oxygen atom or —CH=CH— group, X is a hydrogen atom or a halogen atom.

Preferred compounds of formula (1-c) are more specifically referred to by the following compounds.

(1-c-1)
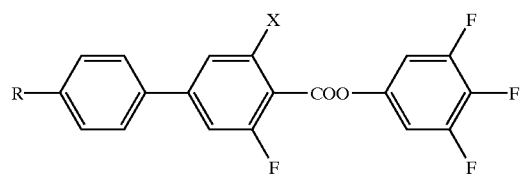

(1-c-2)
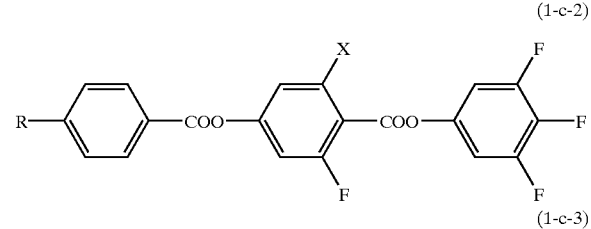

(1-c-3)
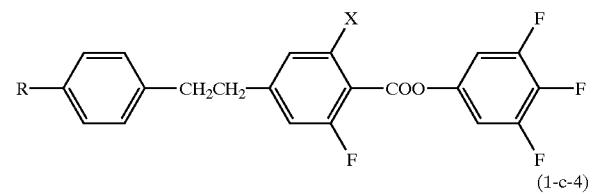

(1-c-4), (1-c-5)
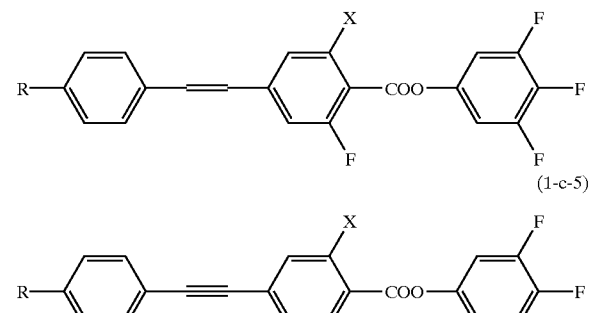
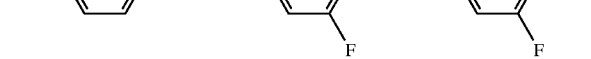

wherein R is a hydrogen atom or a straight or branched-chain alkyl group of 1–9 carbons, one or two non-adjacent CH$_2$ groups of which may be replaced by an oxygen atom or —CH=CH— group, X is a hydrogen atom or a halogen atom.

Preferred compounds of formula (1-d) are more specifically referred to by the following compounds.

(1-d-1)
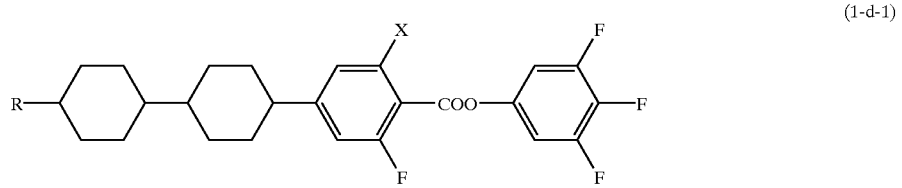

(1-d-2)
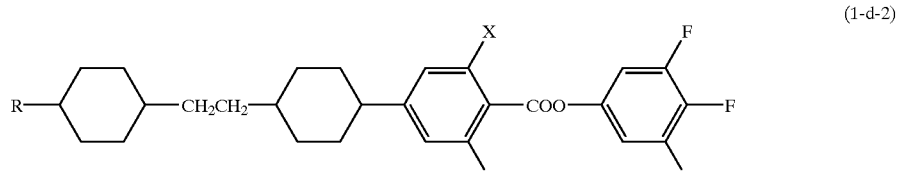

(1-d-3)
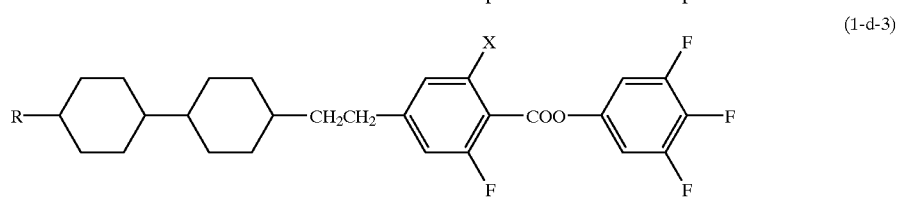

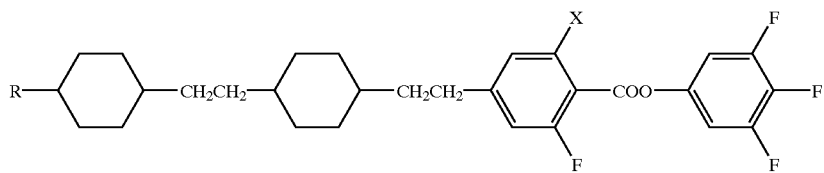 (1-d-4)
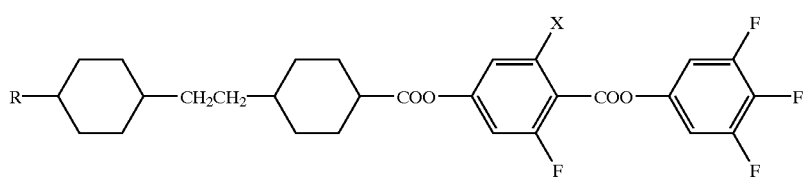 (1-d-5)
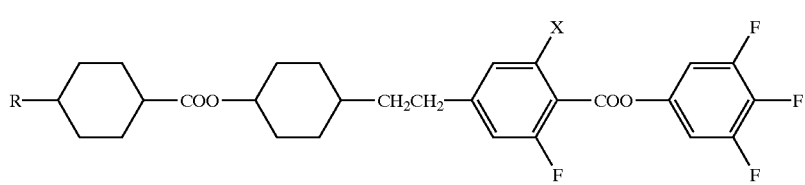 (1-d-6)
wherein R is a hydrogen atom or a straight or branched-chain alkyl group of 1–9 carbons, one or two non-adjacent $CH_2$ groups of which may be replaced by an oxygen atom or —CH=CH— group, X is a hydrogen atom or a halogen atom.
Preferred compounds of formula (1-e) are more specifically referred to by the following compounds.
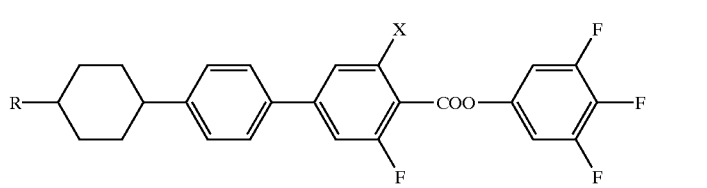 (1-e-1)
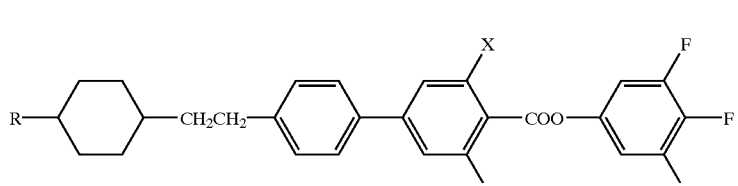 (1-e-2)
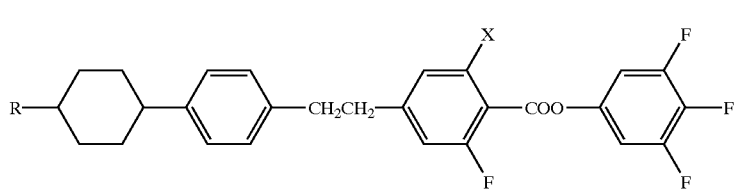 (1-e-3)
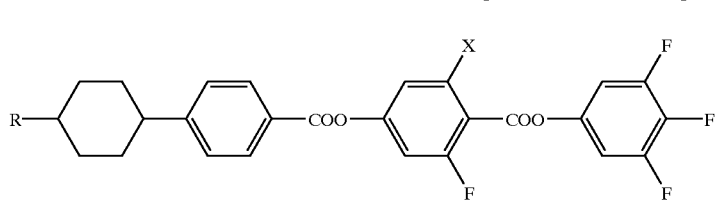 (1-e-4)

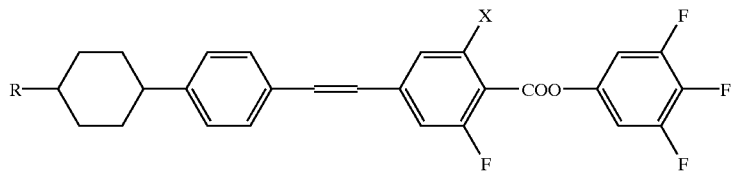
(1-e-5)
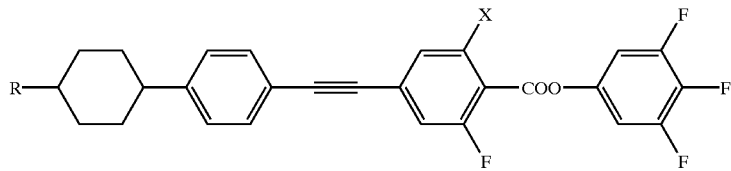
(1-e-6)
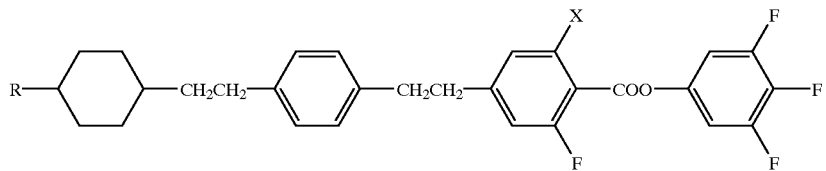
(1-e-7)
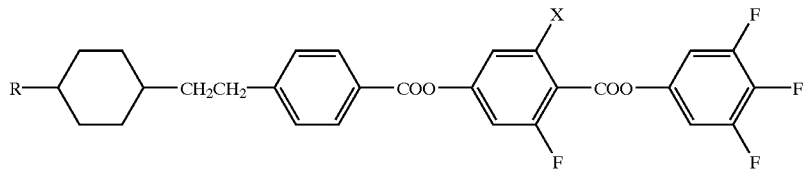
(1-e-8)
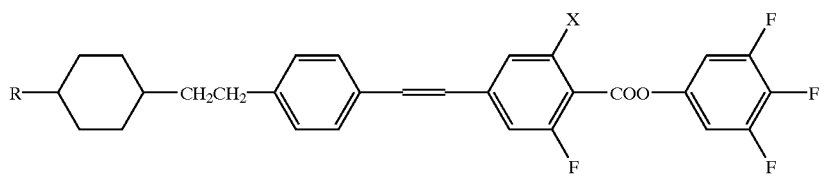
(1-e-9)
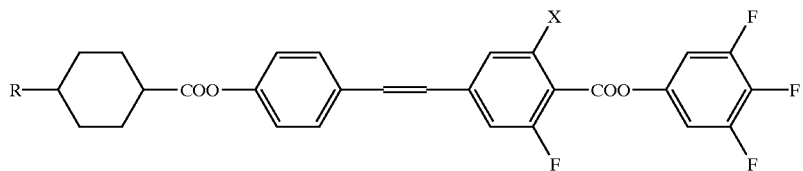
(1-e-10)
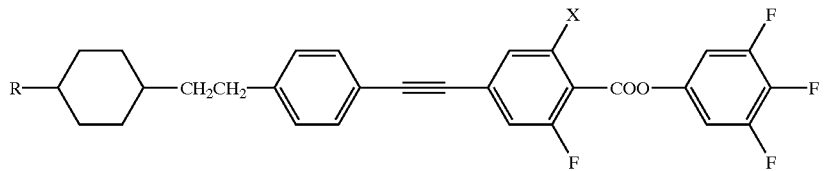
(1-e-11)
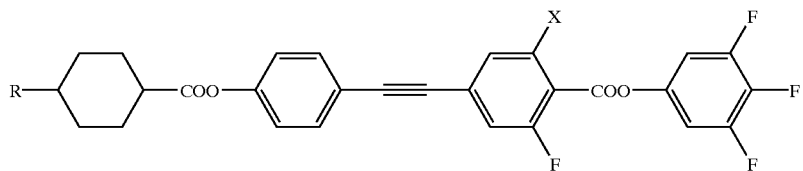
(1-e-12)

wherein R is a hydrogen atom or a straight or branched-chain alkyl group of 1–9 carbons, one or two non-adjacent CH$_2$ groups of which may be replaced by an oxygen atom or —CH=CH— group, X is a hydrogen atom or a halogen atom.
Preferred compounds of formula (1-f) are more specifically referred to by the following compounds.
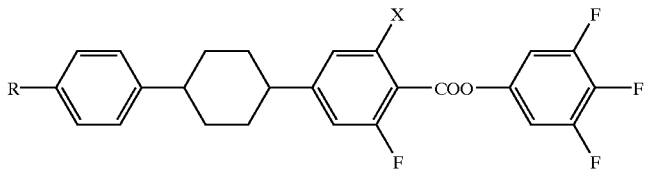
(1-f-1)
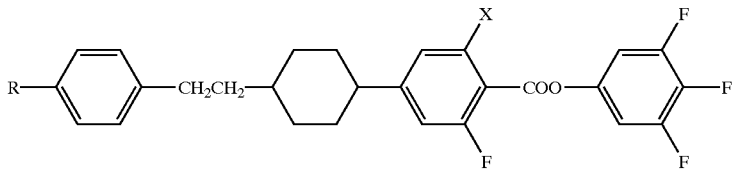
(1-f-2)
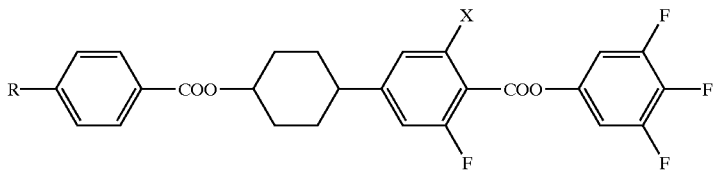
(1-f-3)
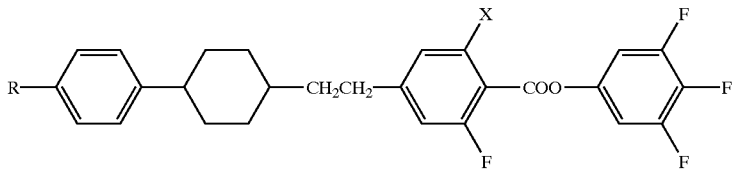
(1-f-4)
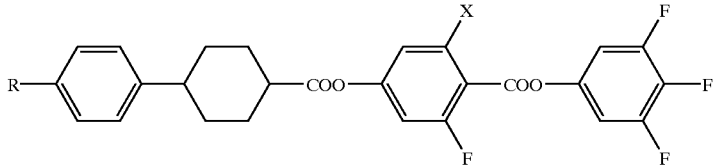
(1-f-5)
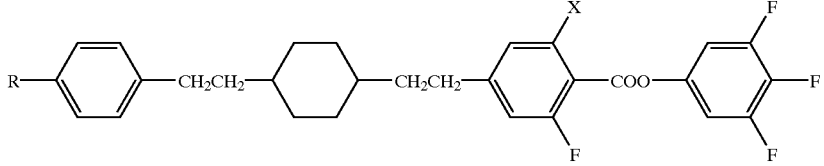
(1-f-6)
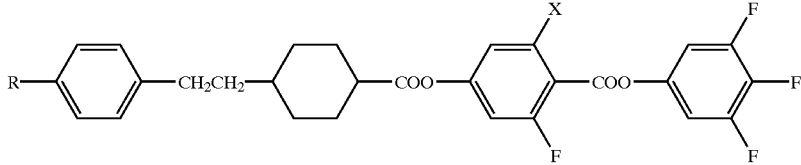
(1-f-7)
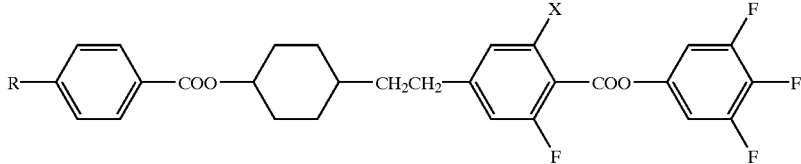
(1-f-8)

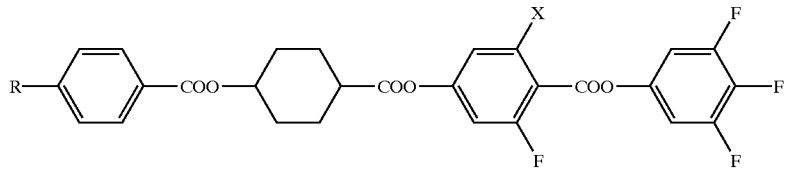
(1-f-9)
wherein R is a hydrogen atom or a straight or branched-chain alkyl group of 1–9 carbons, one or two non-adjacent $CH_2$ groups of which may be replaced by an oxygen atom or —CH=CH— group, X is a hydrogen atom or a halogen atom.
Preferred compounds of formula (1-g) are more specifically referred to by the following compounds.
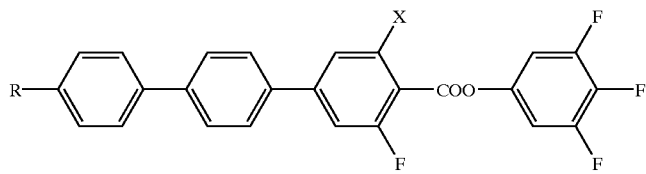
(1-g-1)
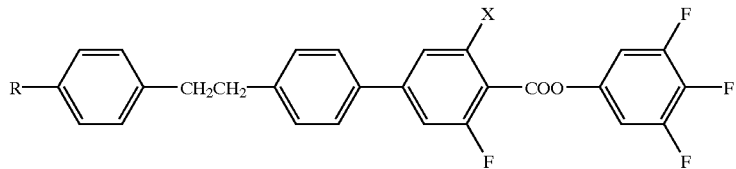
(1-g-2)
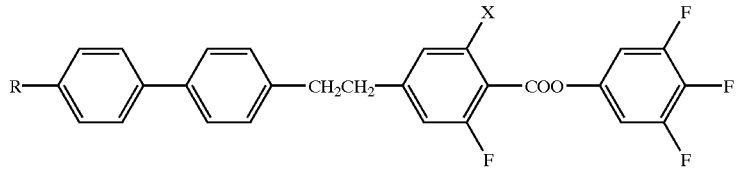
(1-g-3)
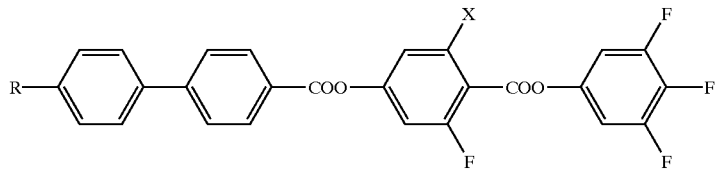
(1-g-4)
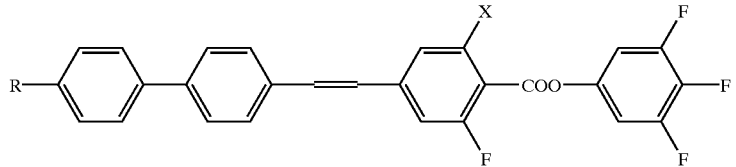
(1-g-5)
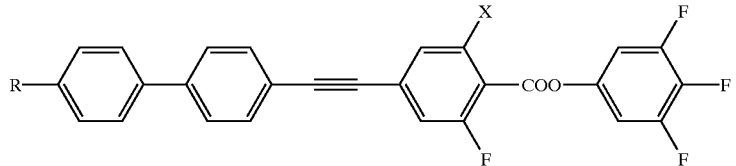
(1-g-6)

-continued
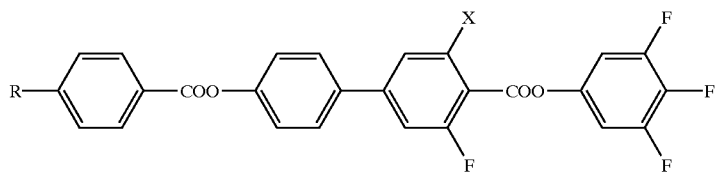
(1-g-7)
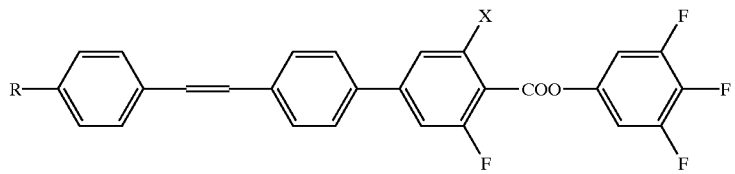
(1-g-8)
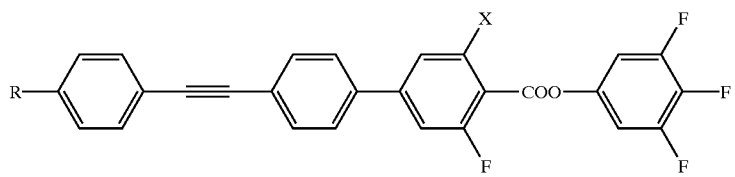
(1-g-9)
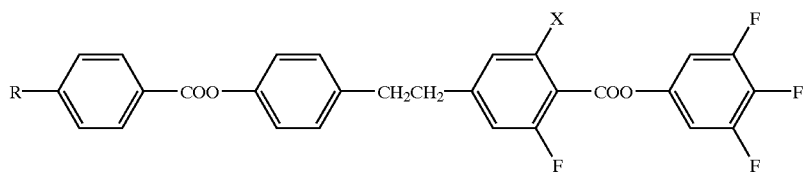
(I-g-10)
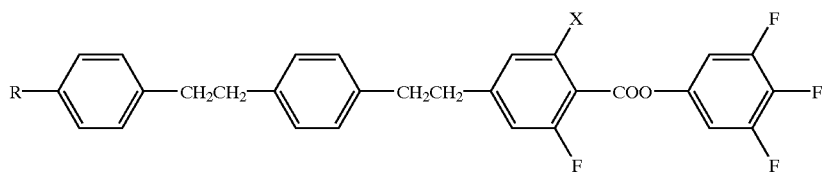
(I-g-11)
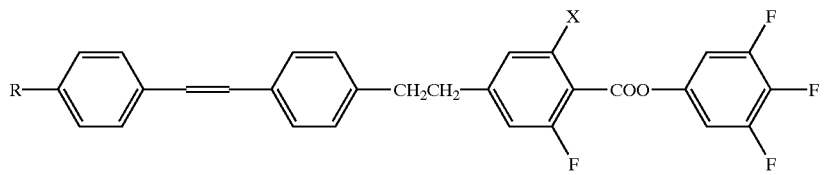
(I-g-12)
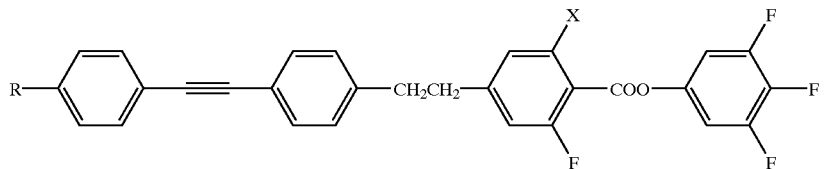
(I-g-13)
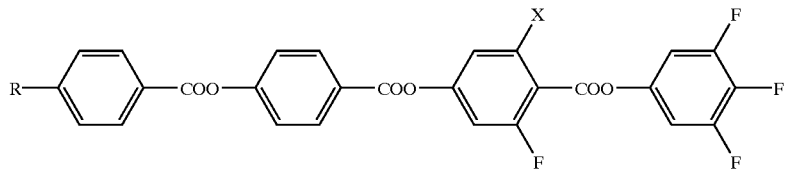
(I-g-14)
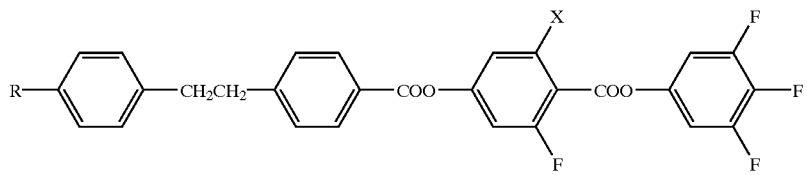
(I-g-15)

-continued
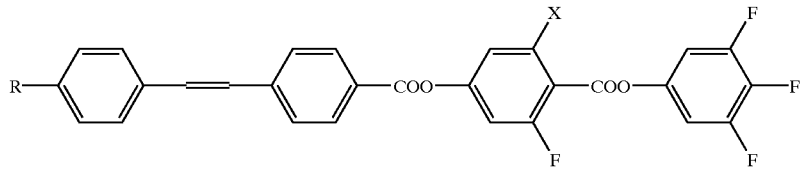
(I-g-16)
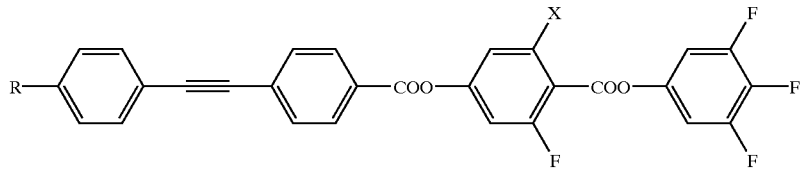
(I-g-17)
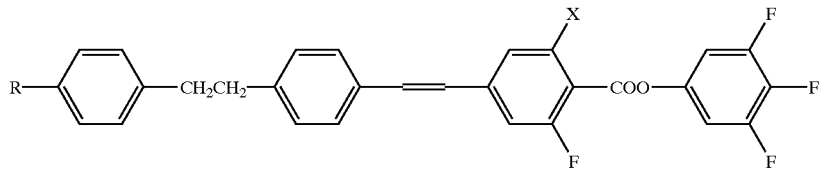
(I-g-18)
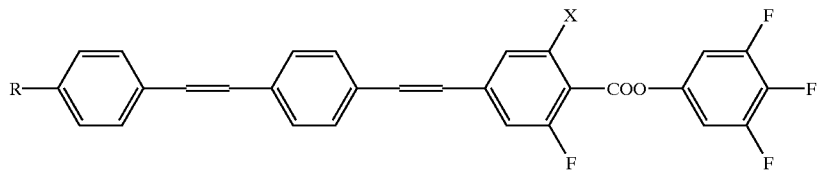
(I-g-19)
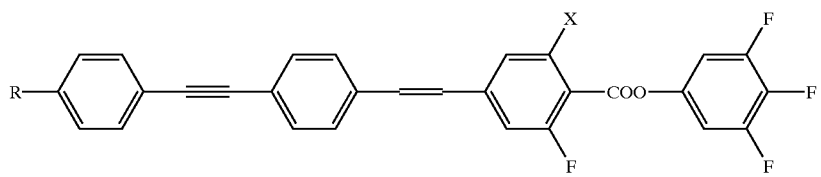
(I-g-20)
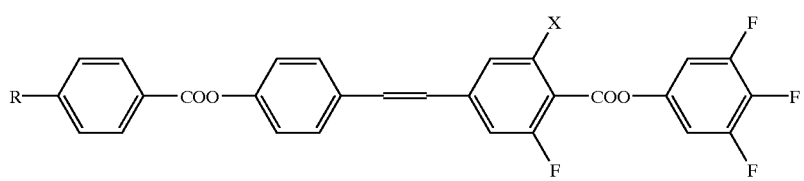
(I-g-21)
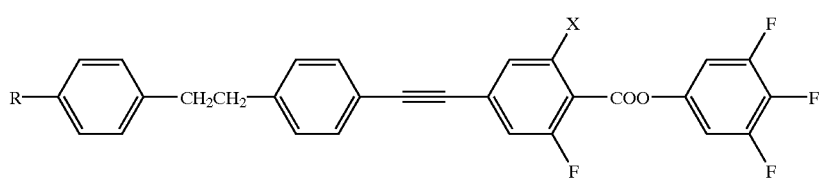
(I-g-22)
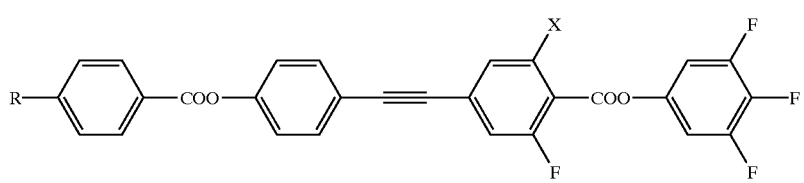
(I-g-23)
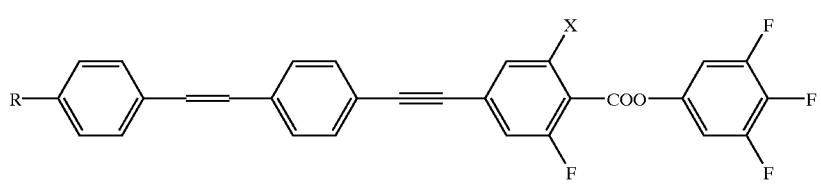
(I-g-24)

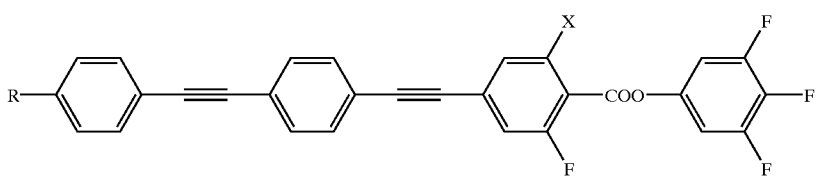
(I-g-25)

wherein R is a hydrogen atom or a straight or branched-chain alkyl group of 1–9 carbons, one or two non-adjacent $CH_2$ groups of which may be replaced by an oxygen atom or —CH=CH— group, X is a hydrogen atom or a halogen atom.

A liquid crystal composition according to the second aspect of this invention may preferably contain one or more of the phenylbenzoate derivatives of formula (1) in an amount of 0.1–99% by weight for producing very good characteristics.

More specifically, the liquid crystal composition provided by the present invention can be completed by blending a first component containing at least one phenylbenzoate derivative of formula (1) with a compound optionally selected from the compounds of formulae (2)–(9) in compliance with the object of a liquid crystal composition.

As the compounds of formulae (2)–(4) used in the invention, the following compounds are preferred, in which $R_1$ is an alkyl or alkoxy group.

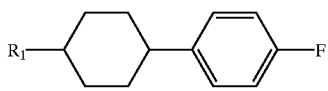
(2-1)

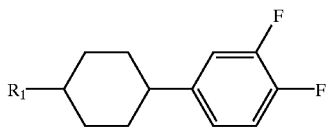
(2-2)

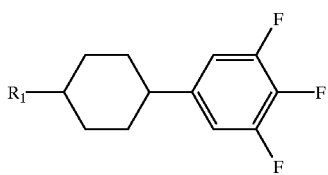
(2-3)

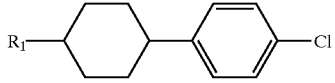
(2-4)

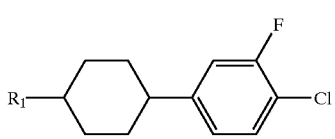
(2-5)

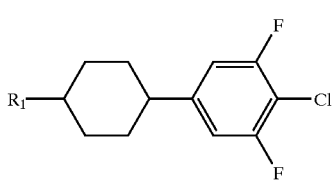
(2-6)

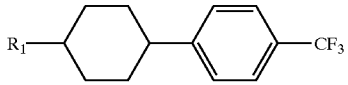
(2-7)

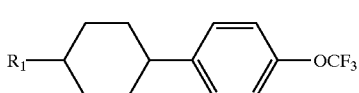
(2-8)

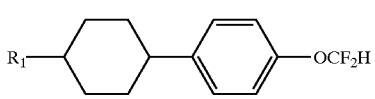
(2-9)

(2-10)

(2-11)

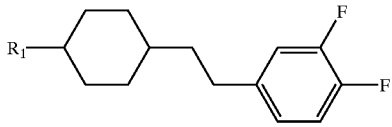
(2-12)

(2-13)

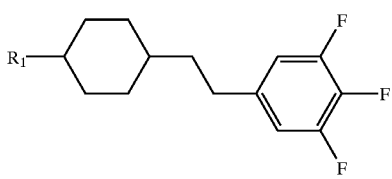
(2-14)

(2-15)

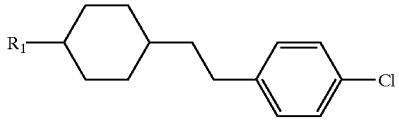

(3-1)

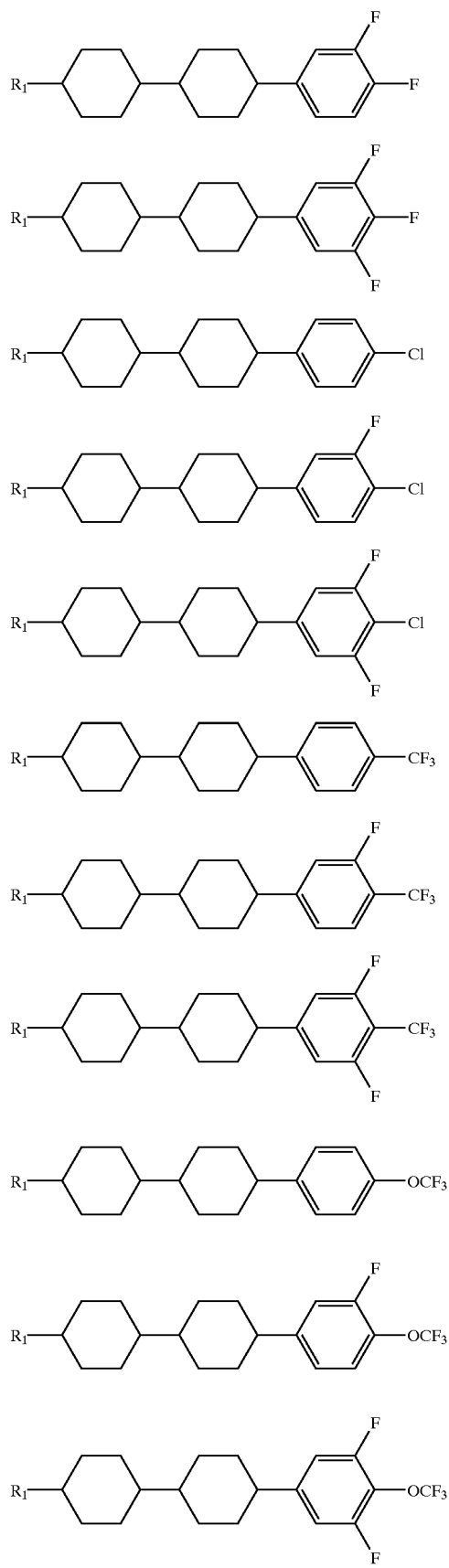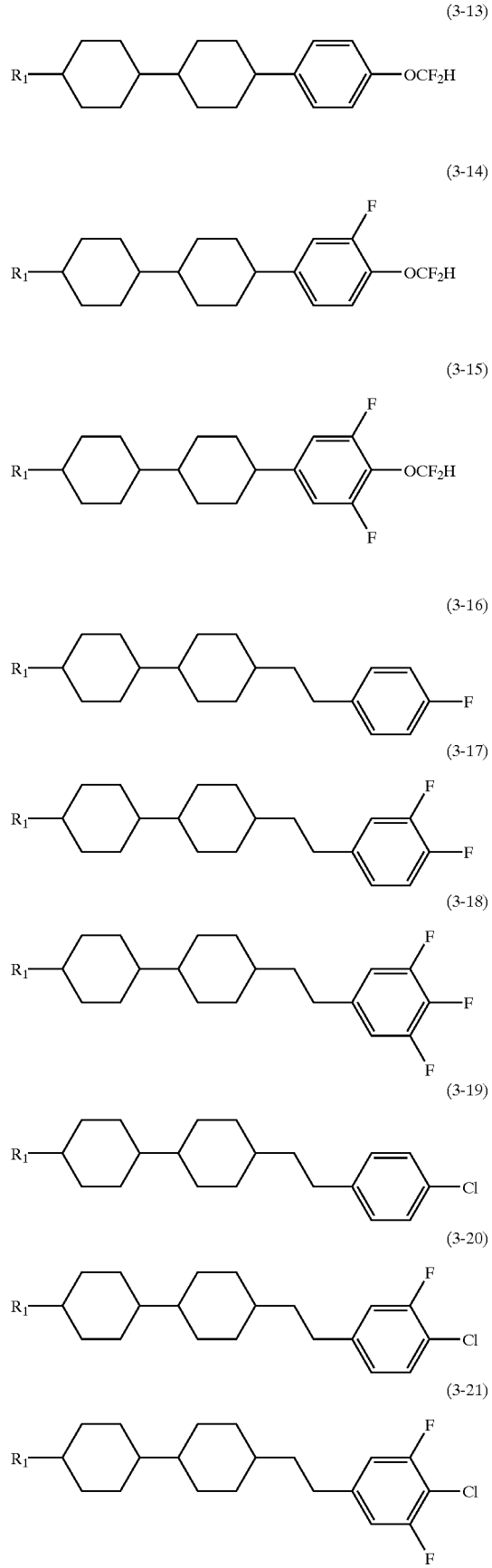

(3-22) 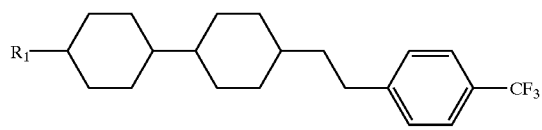
(3-23) 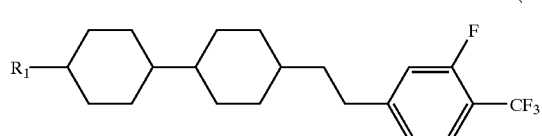
(3-24) 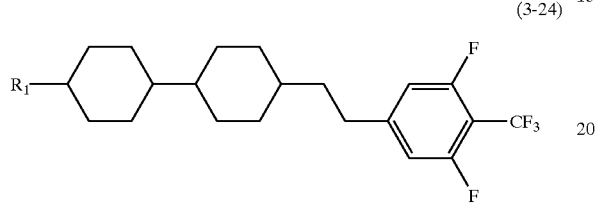
(3-25) 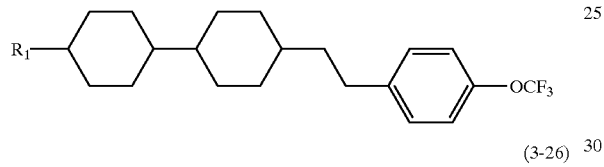
(3-26) 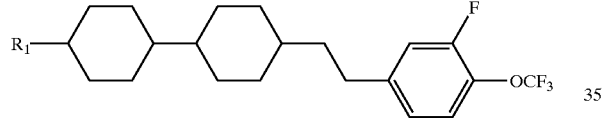
(3-27) 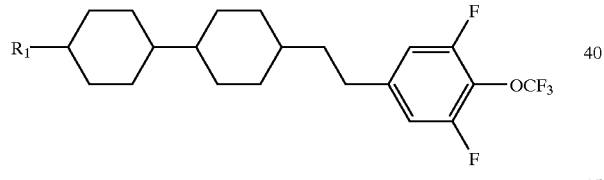
(3-28) 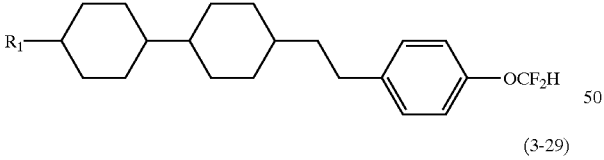
(3-29) 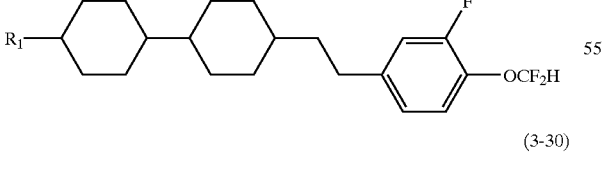
(3-30) 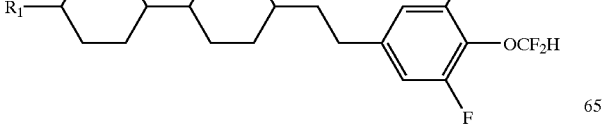
(3-31) 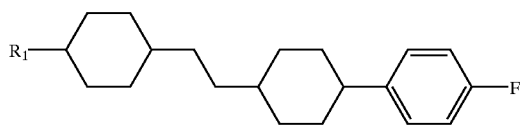
(3-32) 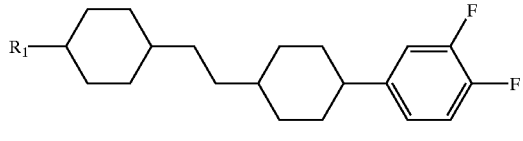
(3-33) 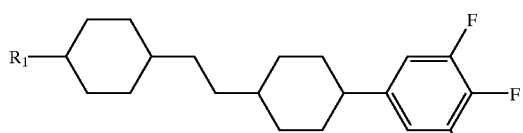
(3-34) 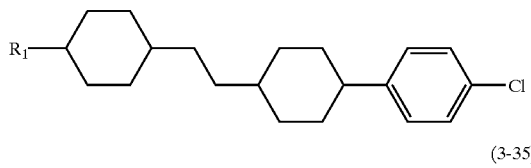
(3-35) 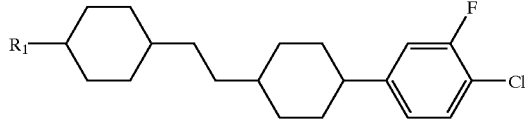
(3-36) 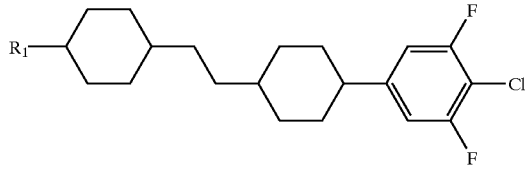
(3-37) 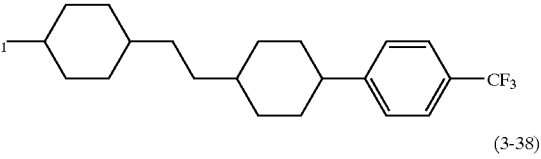
(3-38) 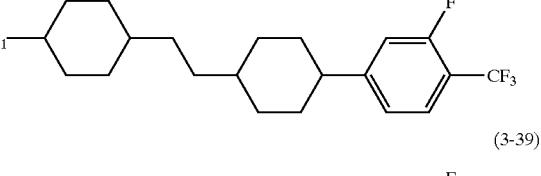
(3-39) 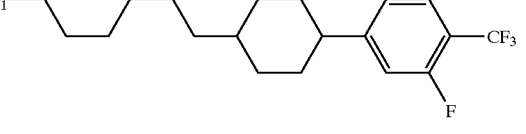

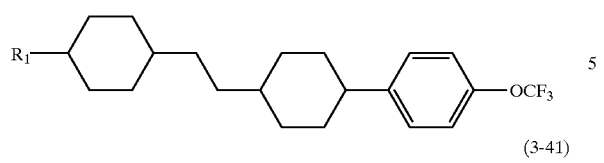
(3-40)
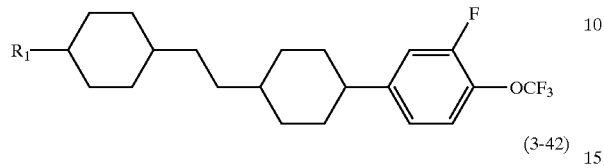
(3-41)
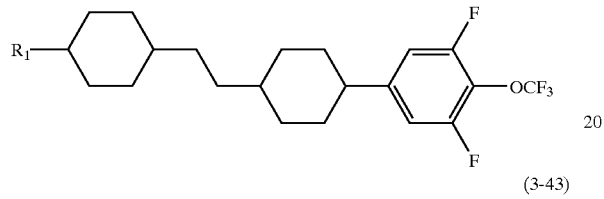
(3-42)
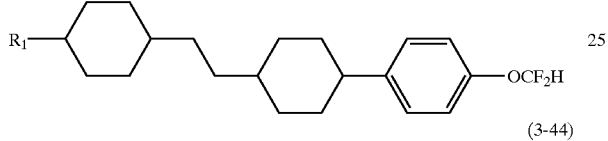
(3-43)
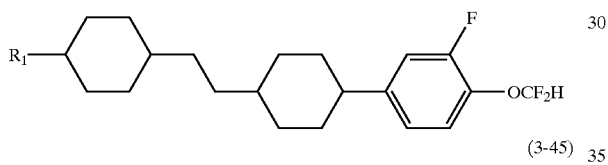
(3-44)
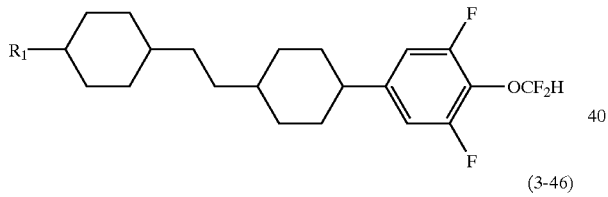
(3-45)
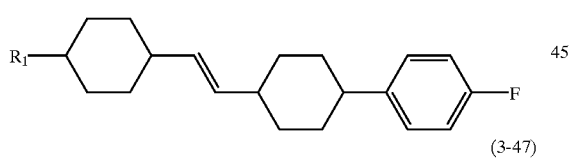
(3-46)
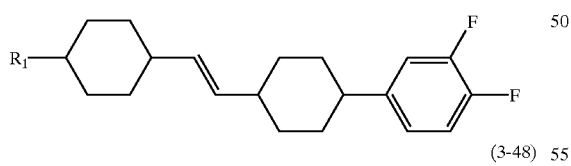
(3-47)
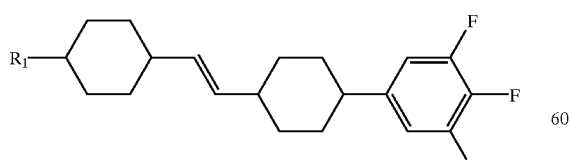
(3-48)
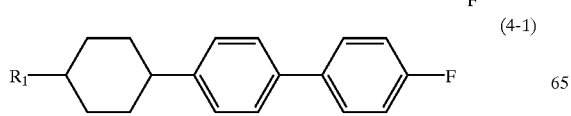
(4-1)
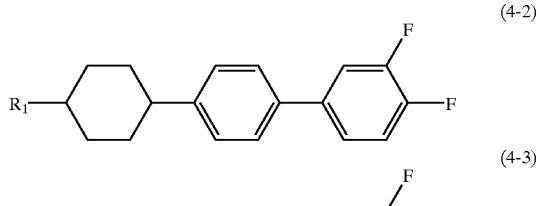
(4-2)
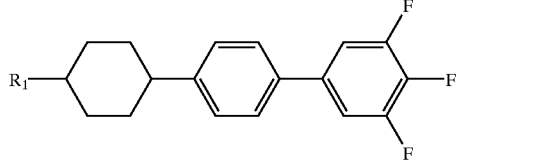
(4-3)
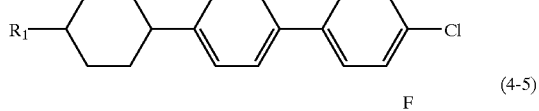
(4-4)
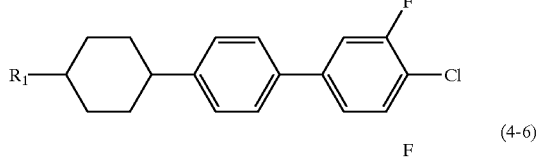
(4-5)
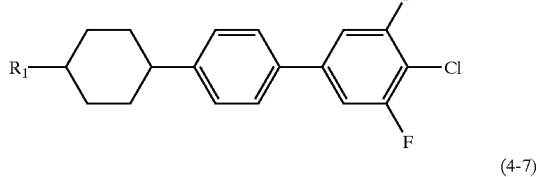
(4-6)
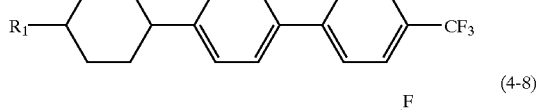
(4-7)
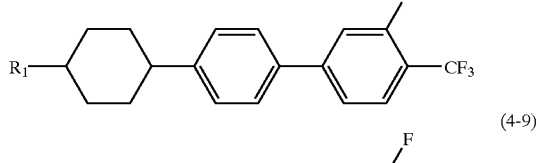
(4-8)
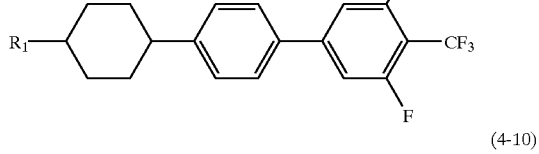
(4-9)
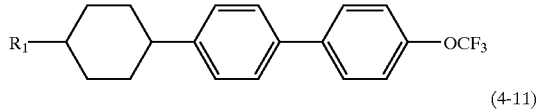
(4-10)
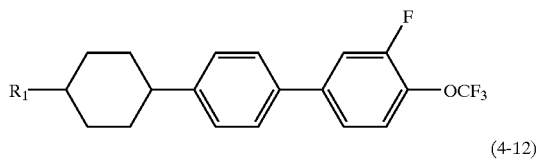
(4-11)
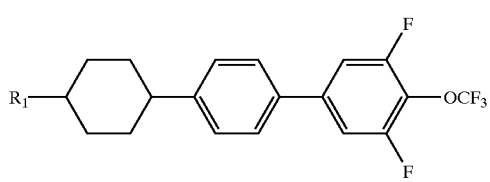
(4-12)

(4-13)
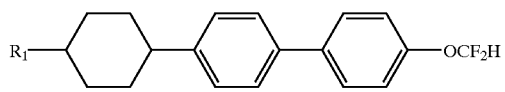
(4-14)
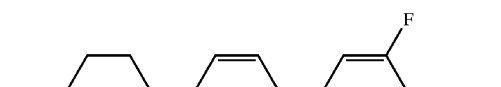
(4-15)
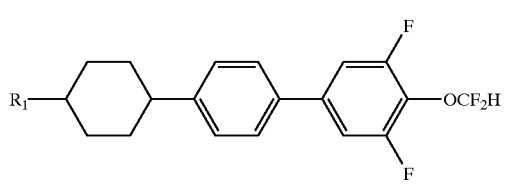
(4-16)
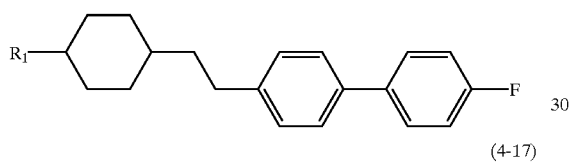
(4-17)
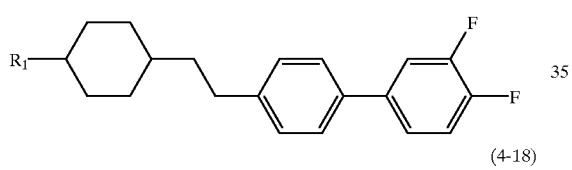
(4-18)
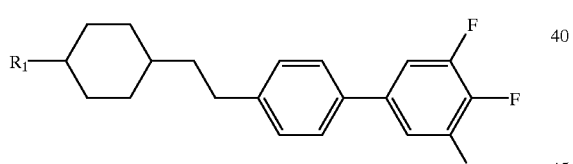
(4-19)
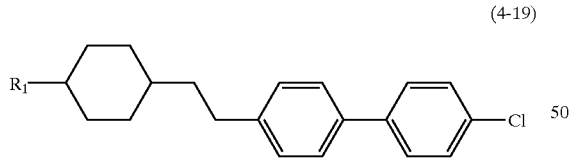
(4-20)
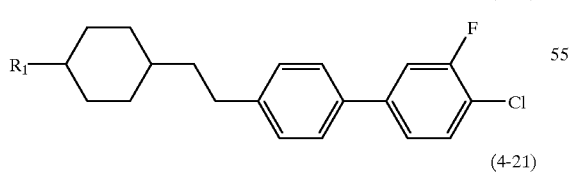
(4-21)
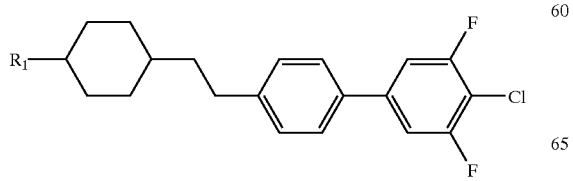
(4-22)
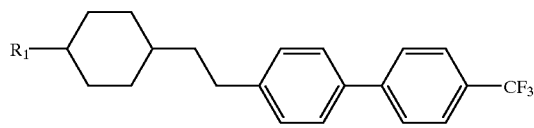
(4-23)
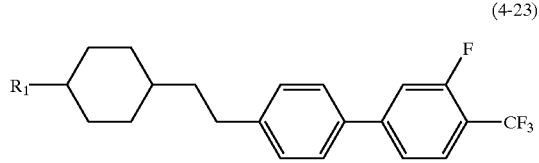
(4-24)
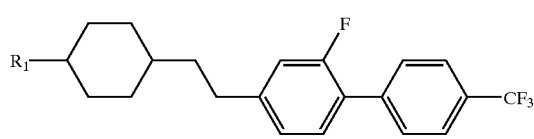
(4-25)
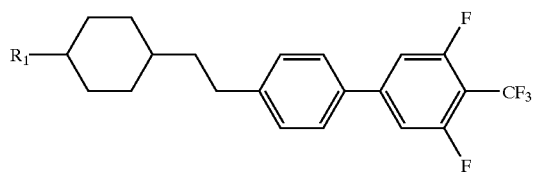
(4-26)
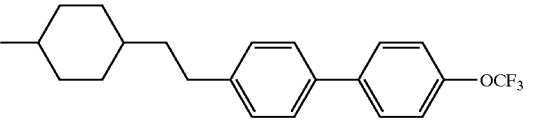
(4-27)
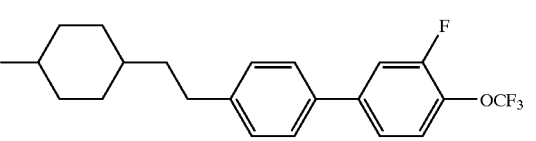
(4-28)
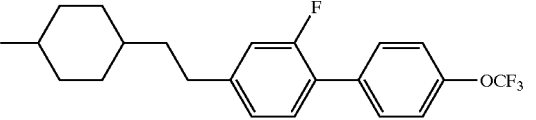
(4-29)
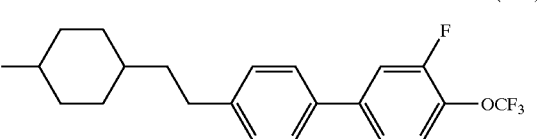
(4-30)
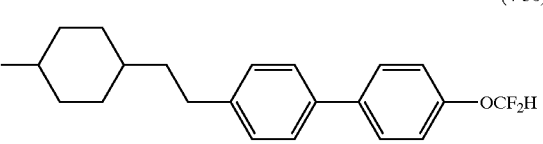

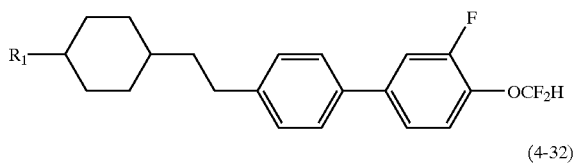
(4-31)

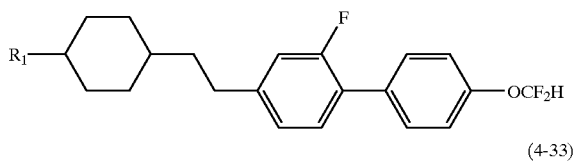
(4-32)

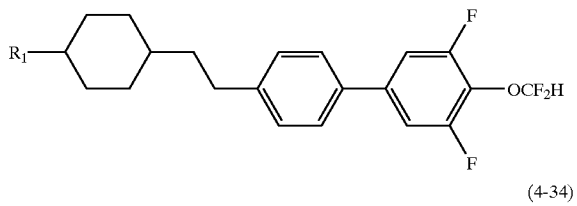
(4-33)

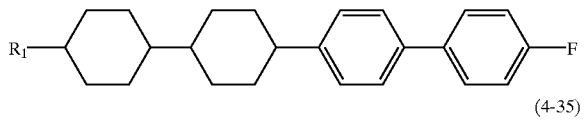
(4-34)

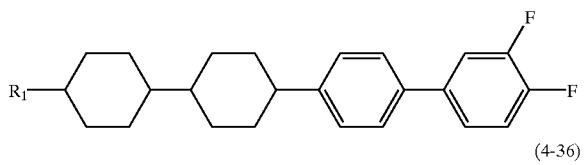
(4-35)

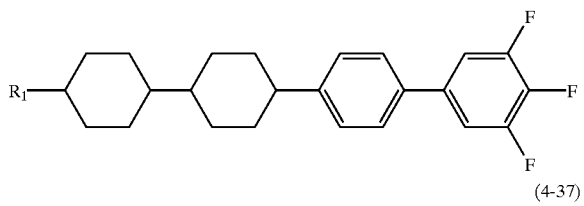
(4-36)

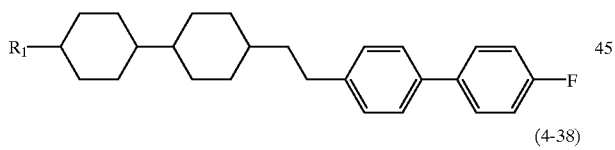
(4-37)

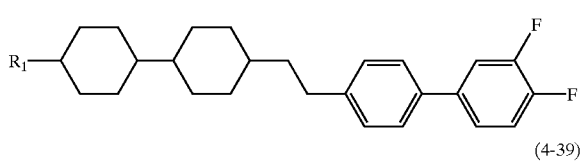
(4-38)

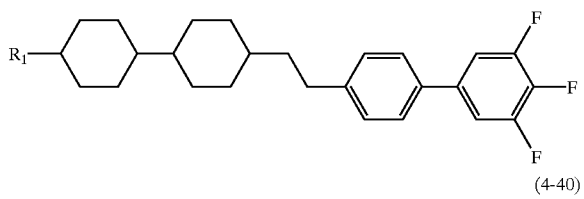
(4-39)

(4-40)

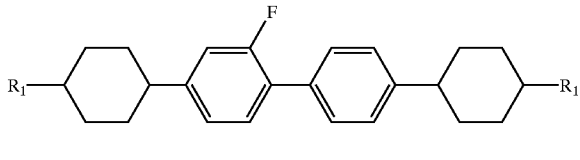
(4-41)

The compounds of formulae (2)–(4) have a positive dielectric anisotropy and very good thermal and chemical stabilities, and they are essential in preparing a liquid crystal composition for TFT (AM-LCD) which requires a high reliability, in particular, a high voltage holding rate or a high specific resistance.

The amount of the compounds of formulae (2)–(4) used may be in the range of 1–99% by weight, preferably 10–97% by weight, based on the total weight of a liquid crystal composition, in the preparation of a liquid crystal composition for TFT. More preferably, it is 40–95% by weight. In this case, the composition may partly contain the compounds of formulae (5)–(9). In the preparation of a liquid crystal composition for STN display mode or usual TN display mode, the compounds of formulae (2)–(4) can be used.

As the compounds of formulae (5)–(7) of the invention, the following compounds are preferable, in which $R_2$, $R_3$ and $R_4$ are an alkyl or alkenyl group and R' is an alkylene group.

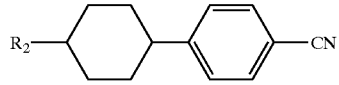
(5-1)

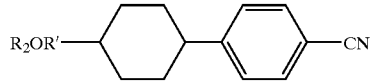
(5-2)

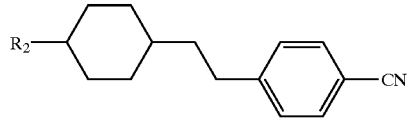
(5-3)

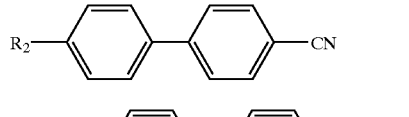
(5-4)

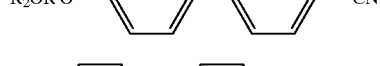
(5-5)

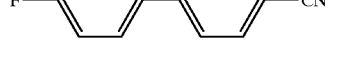
(5-6)

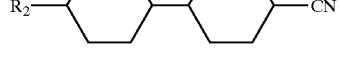
(5-7)

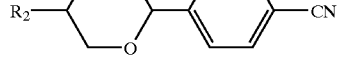
(5-8)

(5-9) (5-10) (5-11) (5-12) (5-13) (5-14) (5-15) (5-16) (5-17) (5-18) (5-19) (5-20) (5-21) (5-22) (5-23) (5-24) (5-25) (5-26) (5-27) (6-1) (6-2) (6-3) (7-1)

-continued (7-2) 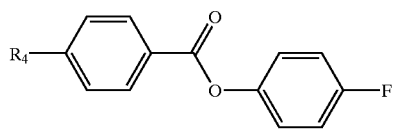

(7-3) 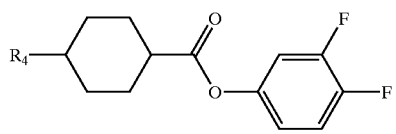

(7-4) 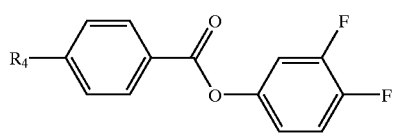

(7-5) 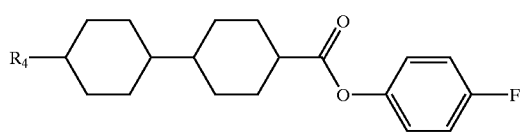

(7-6) 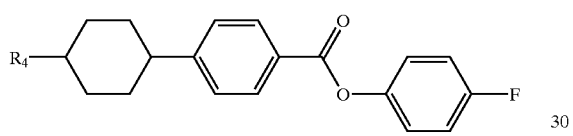

(7-7) 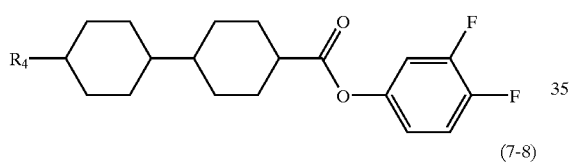

(7-8) 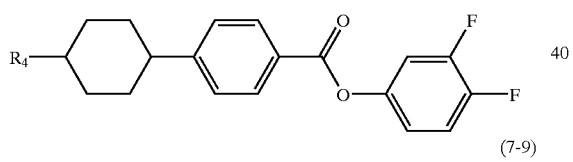

(7-9) 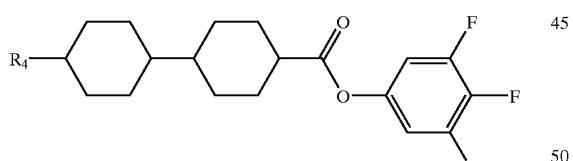

(7-10) 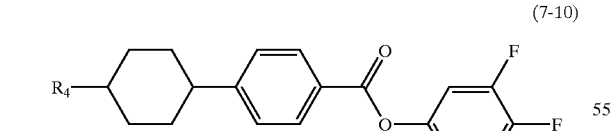

(7-11) 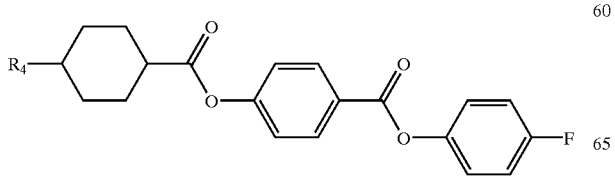

-continued (7-12) 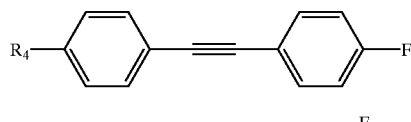

(7-13) 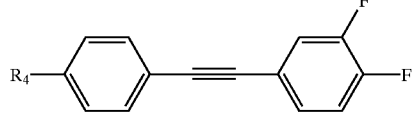

The compounds of formulae (5)–(7) have a positive and high dielectric anisotropy and are used especially for reducing a threshold voltage. They are also used for adjusting a viscosity, adjusting an and broadening a nematic phase range such as an increase in clearing point or the like. Further, they are used for improving steepness.

As the compounds of formulae (8) and (9), the following compounds are preferable, in which $R_5$, $R_6$, $R_7$ and $R_8$ are an alkyl or alkenyl group.

(8-1) 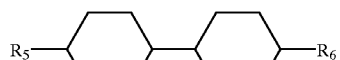

(8-2) 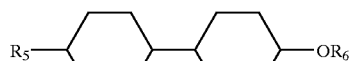

(8-3) 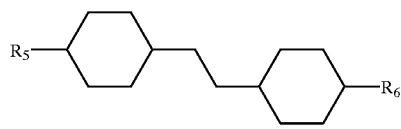

(8-4) 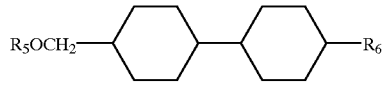

(8-5) 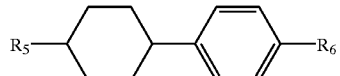

(8-6) 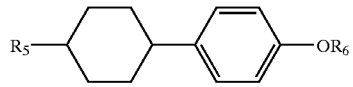

(8-7) 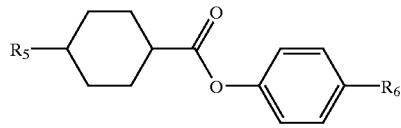

(8-8) 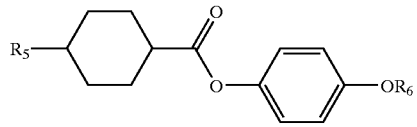

(8-9) 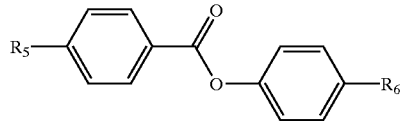

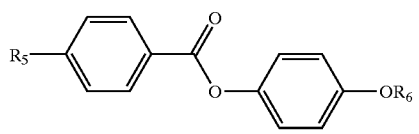
(8-10)

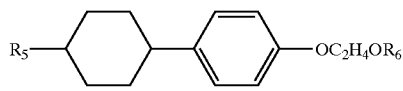
(8-11)

(8-12)

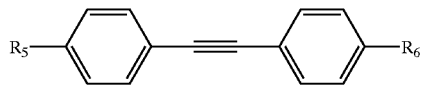
(8-13)

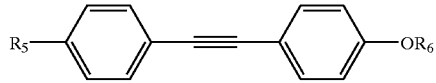
(8-14)

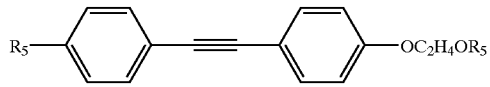
(8-15)

(9-1)

(9-2)

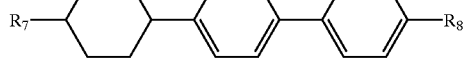
(9-3)

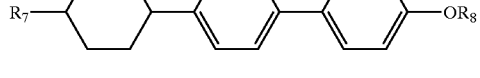
(9-4)

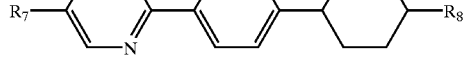
(9-5)

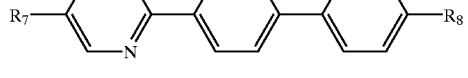
(9-6)

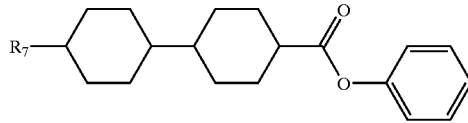
(9-7)

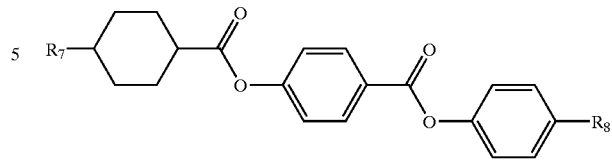
(9-8)

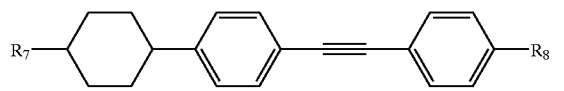
(9-9)

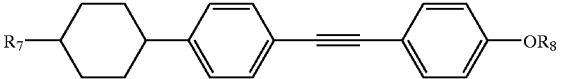
(9-10)

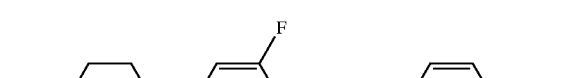
(9-11)

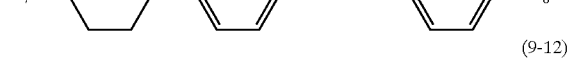
(9-12)

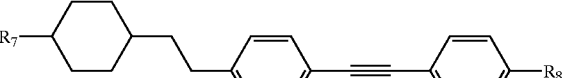
(9-13)

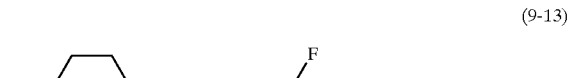
(9-14)

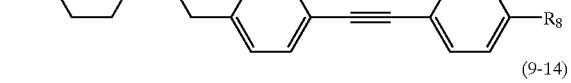

The compounds of formulae (8) and (9) are those which have a negative or weakly positive dielectric anisotropy. The compounds of formula (8) are used mainly for reducing viscosity and/or for adjusting an. The compounds of formula (9) are used for broadening a nematic phase range such as an increase in a clear point and/or for adjusting Δn.

The compounds of formulae (5)–(9) are essential particularly for the preparation of a liquid crystal composition for STN display mode and usual TN display mode.

The amount of the compounds of formulae (5)–(9) used may be in the range of 1–99% by weight in the preparation of a liquid crystal composition for usual TN display mode and STN display mode, and 10–97% by weight is preferable. 40–95% by weight is more preferable. In this case, the compounds of formulae (2)–(4) may also be used in part.

The use of the present liquid crystal composition for a TFT liquid crystal display element can improve the steepness and the viewing angle. Since the compounds of formula (1) are of a low viscosity, the response rate of the liquid crystal display element using those compounds is improved.

The liquid crystal compositions used according to the invention are prepared by the processes conventional per se.

In general, there are employed the processes wherein various components are mutually dissolved at an elevated temperature. The liquid crystal materials of the invention are improved and optimized in compliance with the use as intended by using suitable additives. Such additives are well known to those skilled in the art and also described in detail in literatures. Usually, a chiral dopant is added for inducing helical structures of the liquid crystal to control necessary twist angle and preventing a reverse twist.

Further, the liquid crystal compositions of the present invention can be used as liquid crystal materials for guest-host (GH) mode by incorporating therein dichronic dyes such as merocyanines, styryls, azo, azomethines, azoxy, quinophthalones, anthraquinones, tetrazines or the like. Alternatively, they can be used as liquid crystal materials for NPCA formed by micro-capsulation of nematic liquid crystals, or as liquid crystal materials for polymer dispersed liquid crystal display elements (PDLCD), a typical example of which is a polymer network liquid crystal display element (PNLCD) wherein a three-dimensional network polymer is formed in the liquid crystal. In addition, they can be used as liquid crystal materials for electrically controlled birefringence (ECB) mode and dynamic scattering (DS) mode.

The nematic liquid crystal compositions containing the phenylbenzoate derivatives of the invention can be illustrated by the following Composition Examples.

Composition Example 1

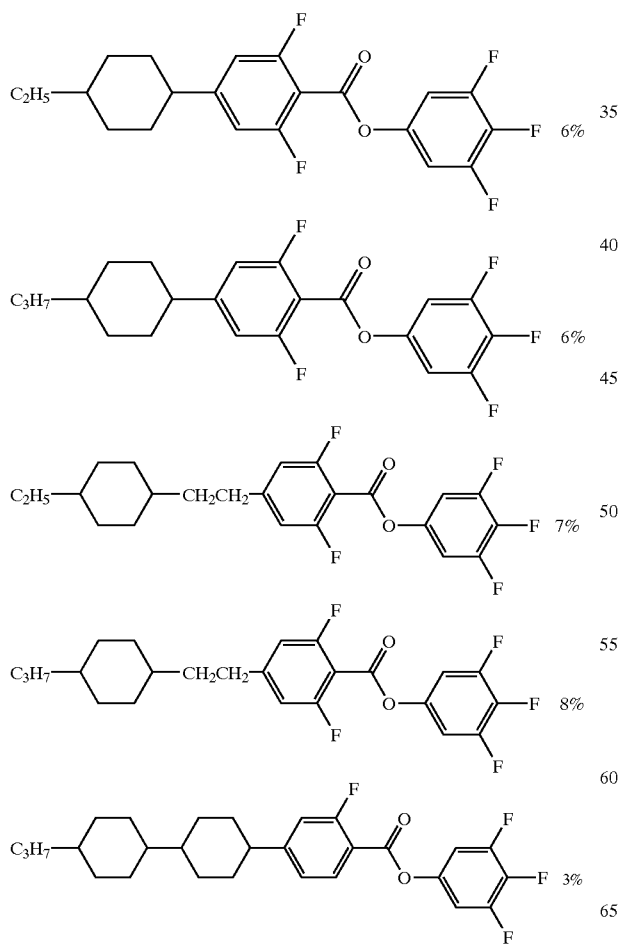

-continued

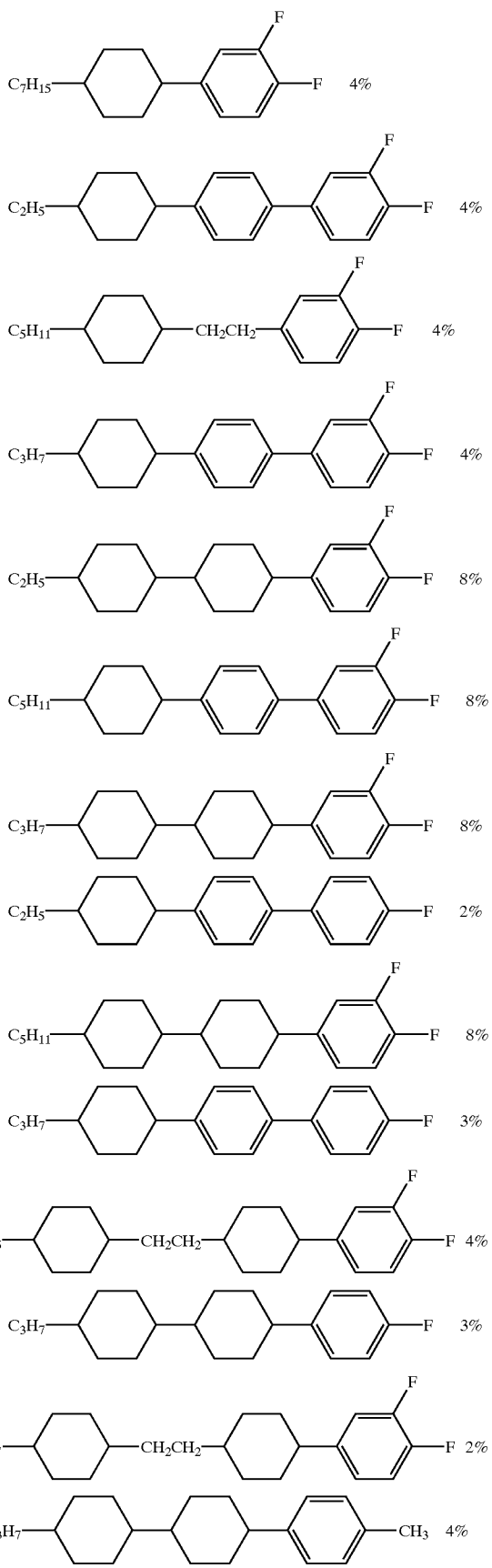

-continued
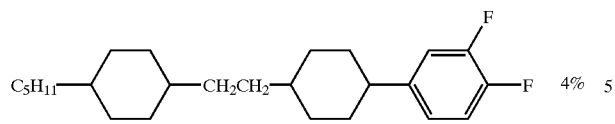 4%
Composition Example 2
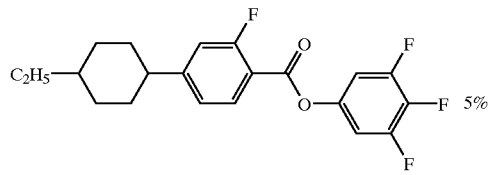 5%  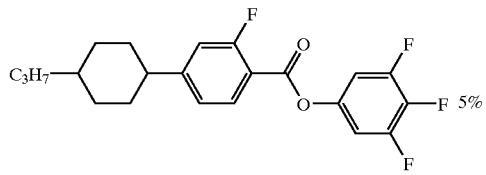 5%
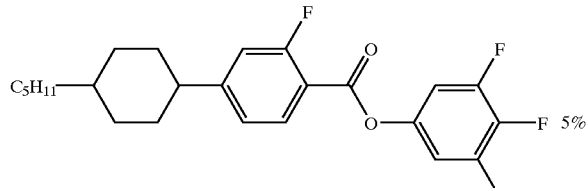 5%
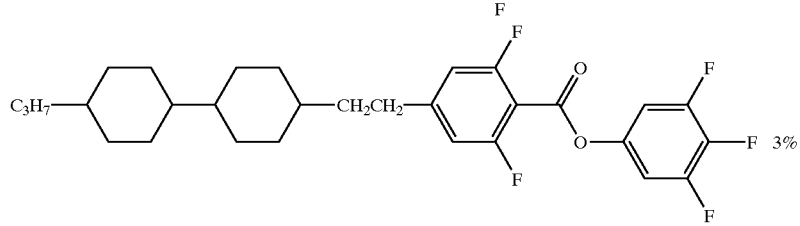 3%
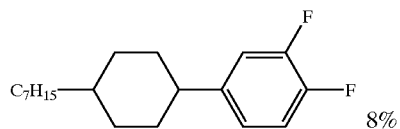 8%  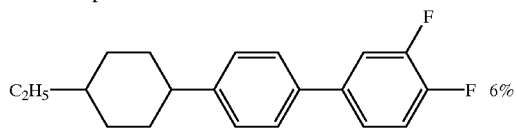 6%
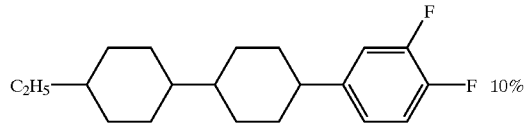 10%  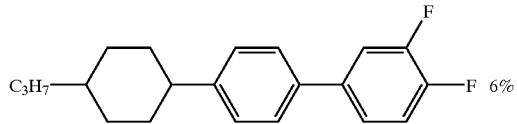 6%
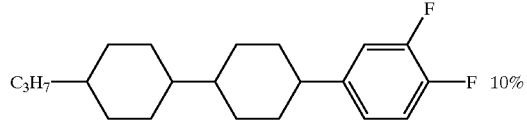 10%  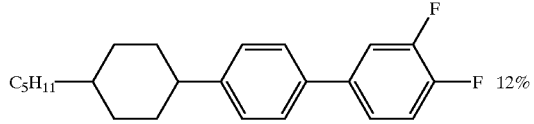 12%
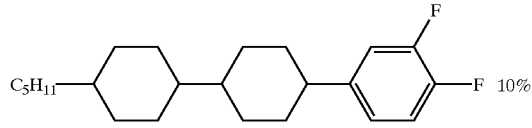 10%
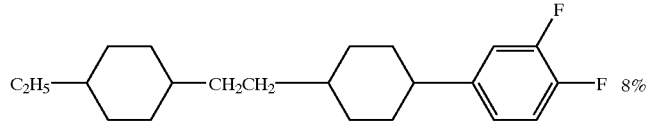 8%
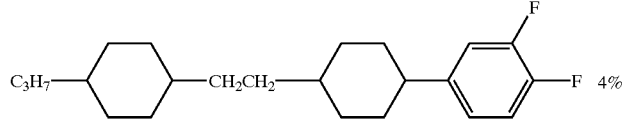 4%
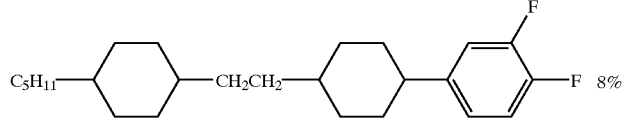 8%

Composition Example 3
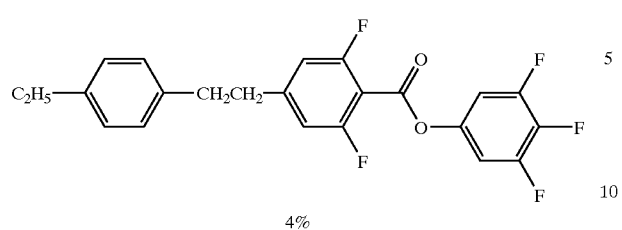
4%
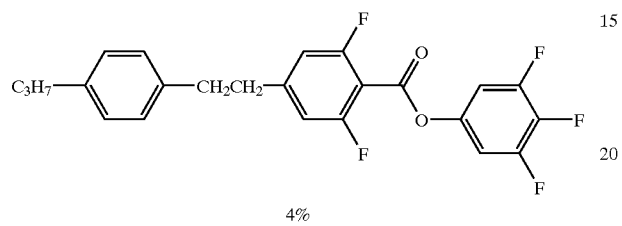
4%
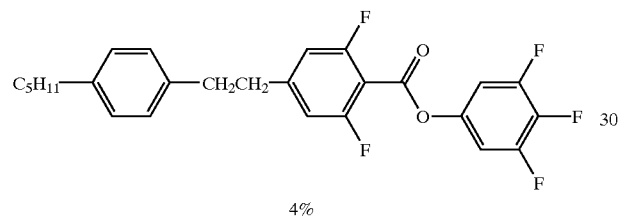
4%
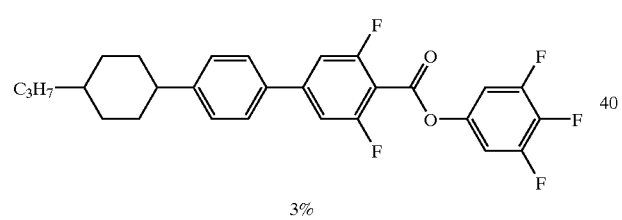
3%
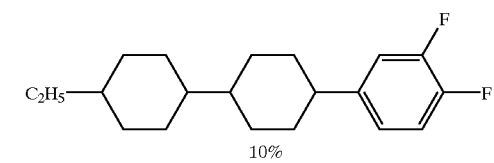
10%
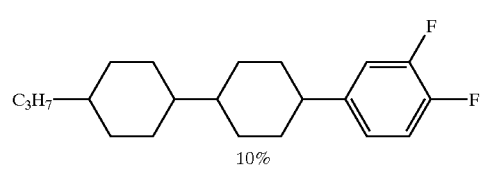
10%
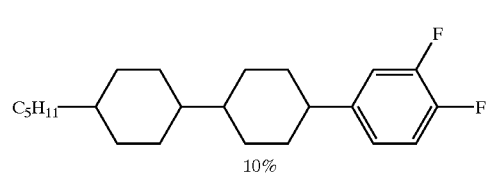
10%
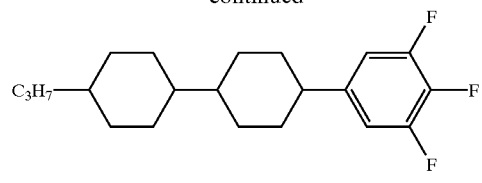
5%
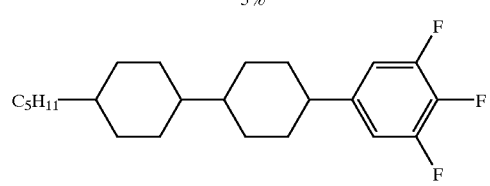
3%
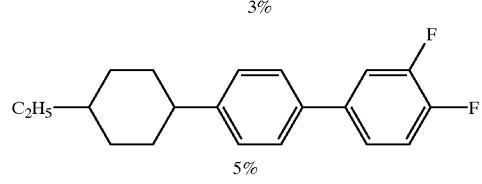
5%
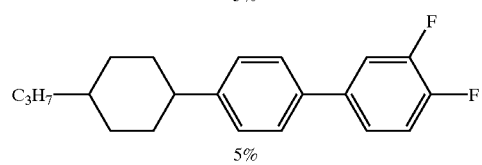
5%
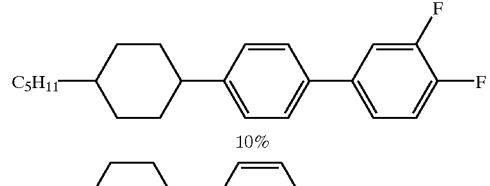
10%
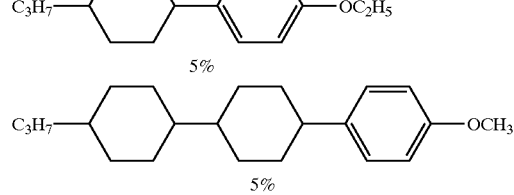
5%
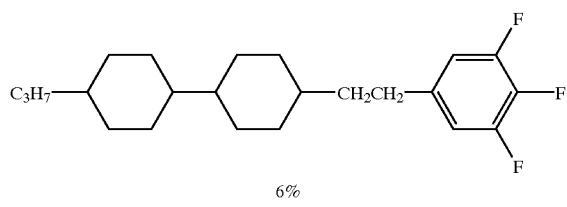
5%
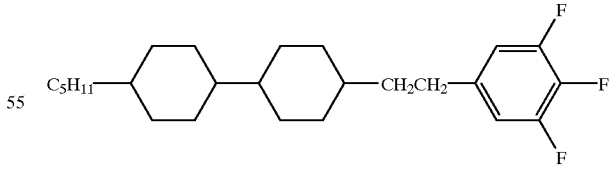
6%
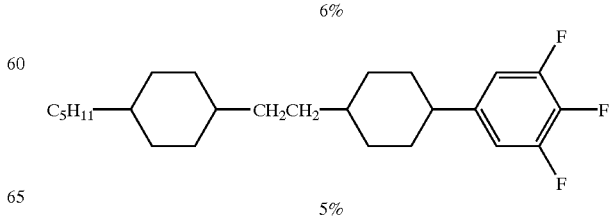
6%
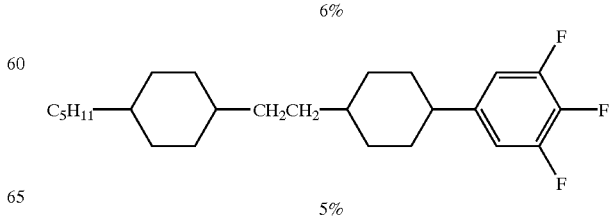
5%

Composition Example 4
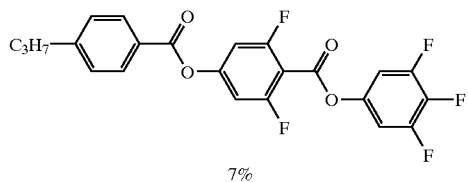
7%
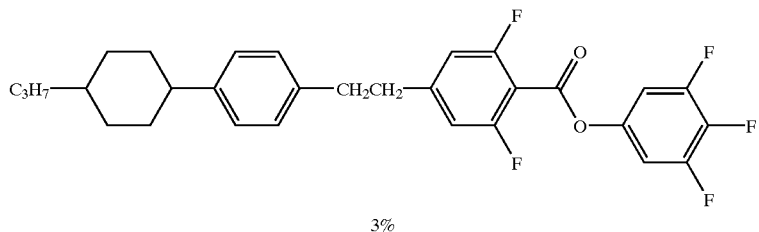
3%
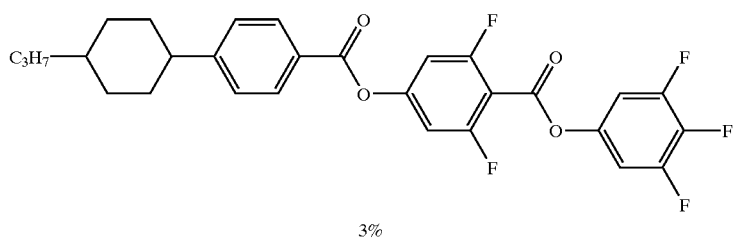
3%
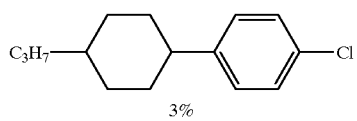
3%
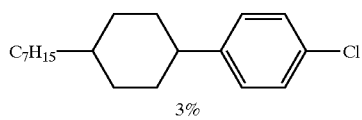
3%
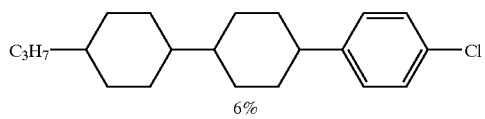
6%
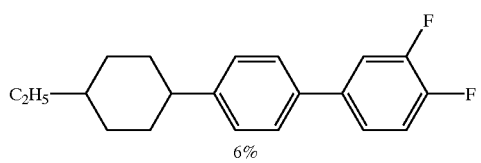
6%
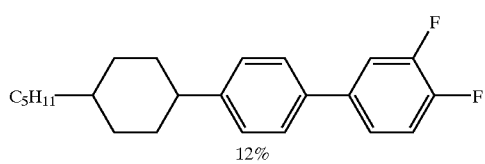
12%
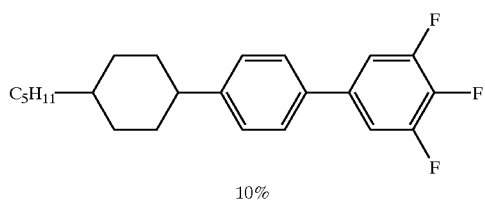
10%
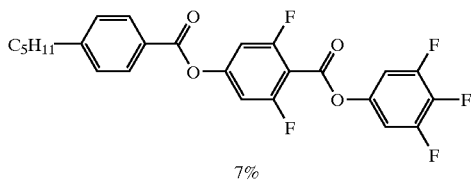
7%
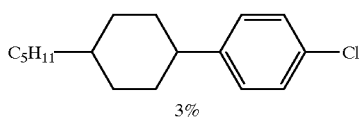
3%
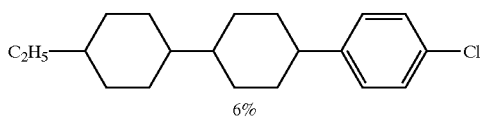
6%
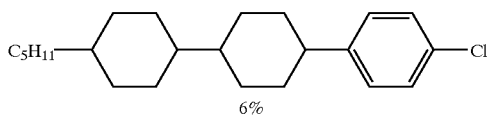
6%
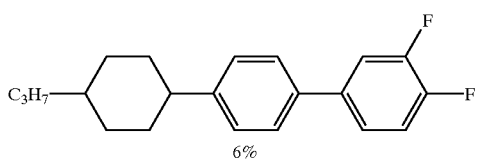
6%
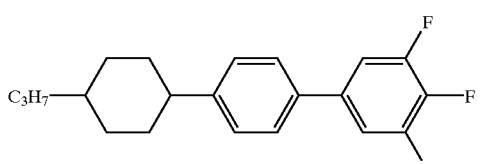
10%

-continued
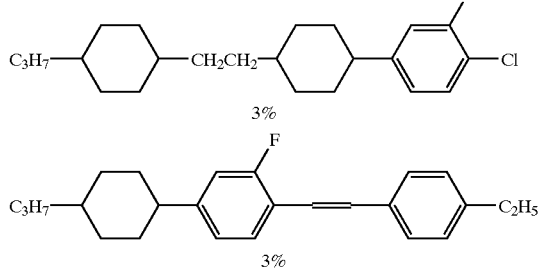 3%
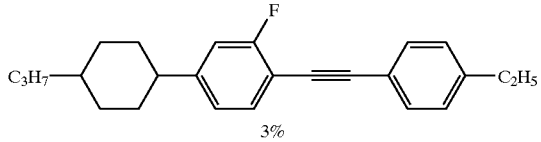 3%
Composition Example 5
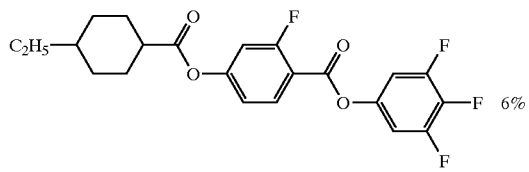 6%
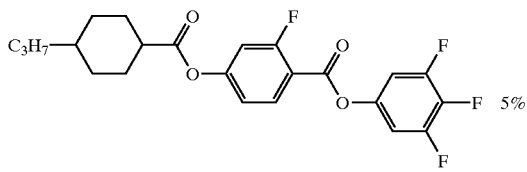 5%
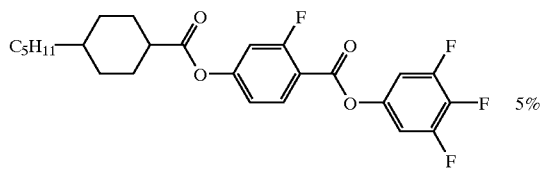 5%
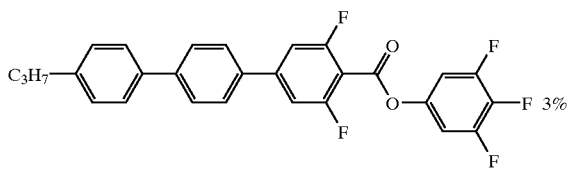 3%
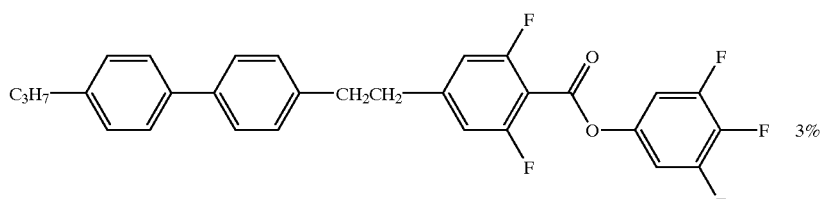 3%
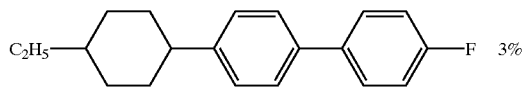 3%
 3%
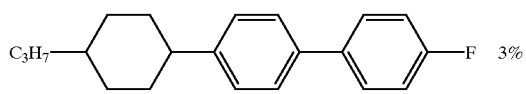 3%
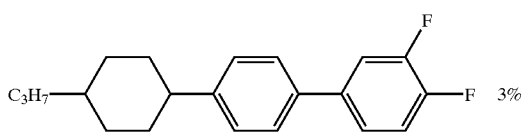 3%
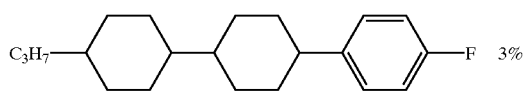 3%
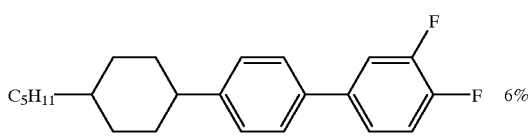 6%
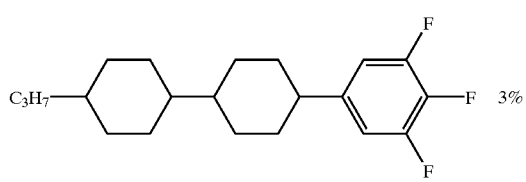 3%
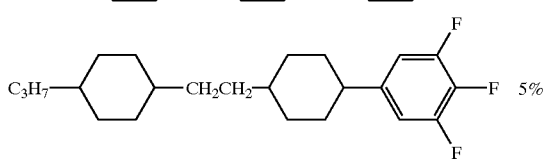 5%
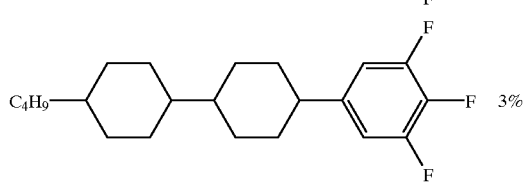 3%
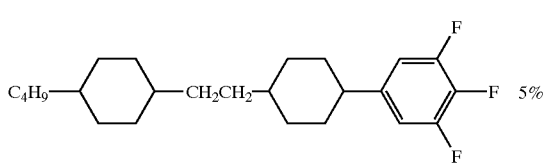 5%

-continued
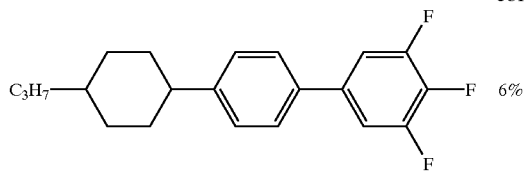 6%
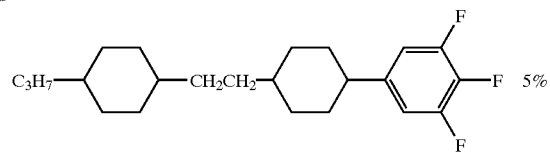 5%
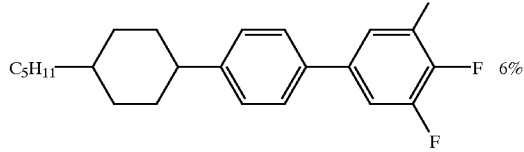 6%
 3%
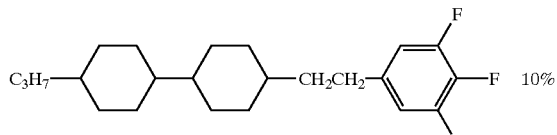 10%
 3%
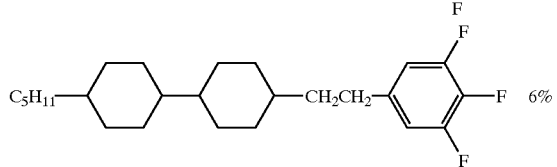 6%
Composition Example 6
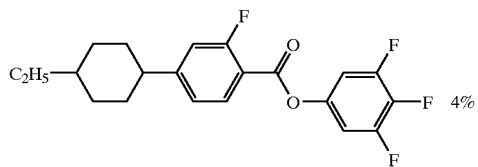 4%
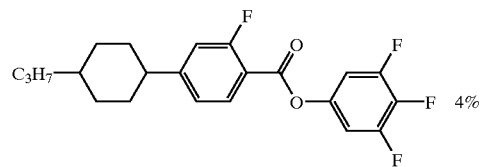 4%
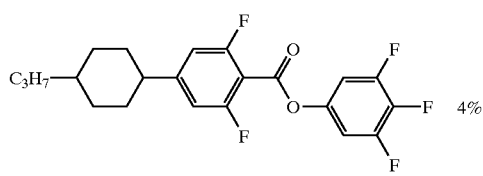 4%
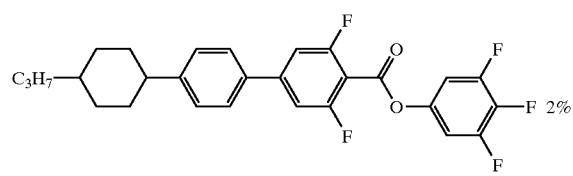 2%
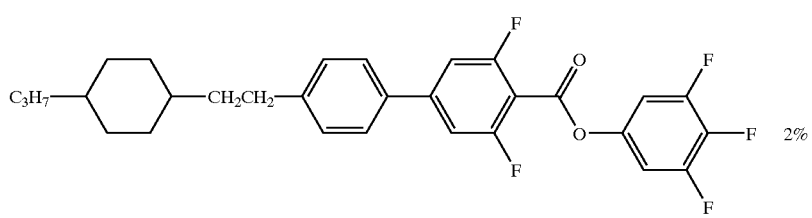 2%
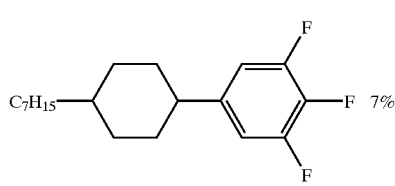 7%
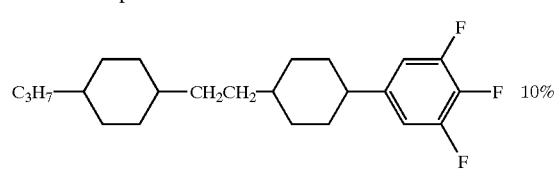 10%
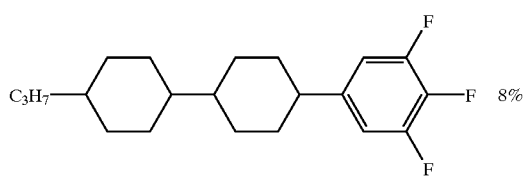 8%
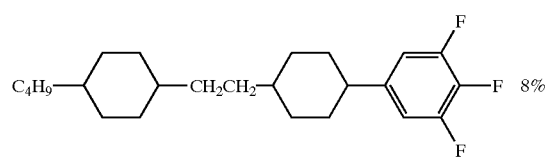 8%

-continued
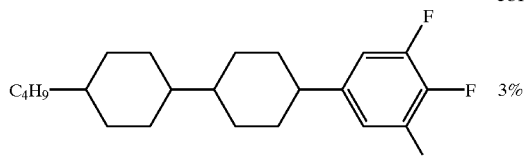 3%
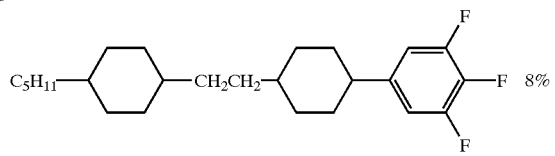 8%
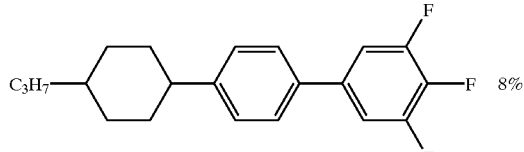 8%
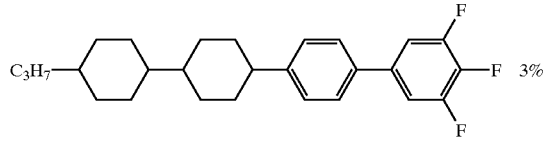 3%
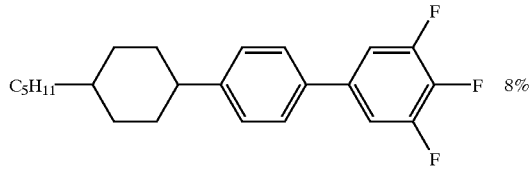 8%
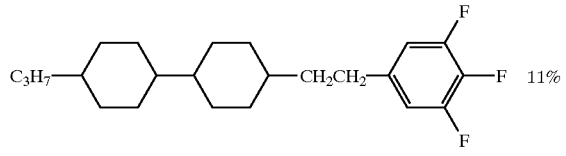 11%
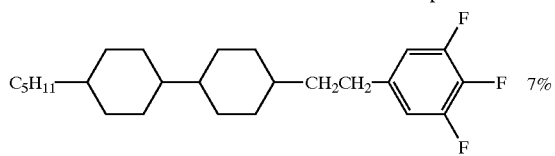 7%
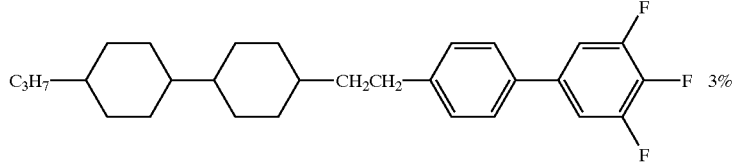 3%
Composition Example 7
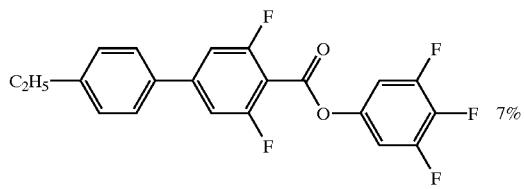 7%
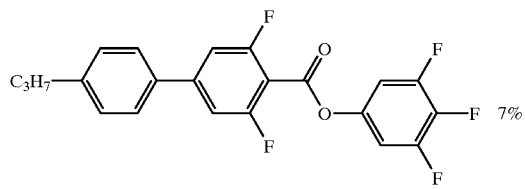 7%
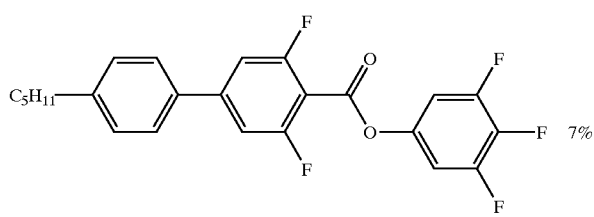 7%
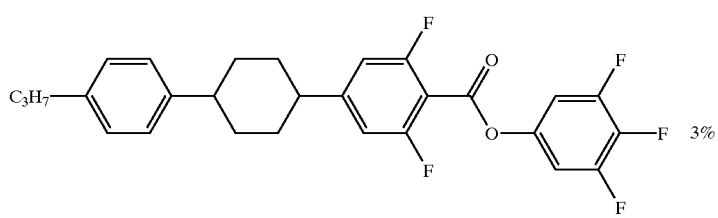 3%

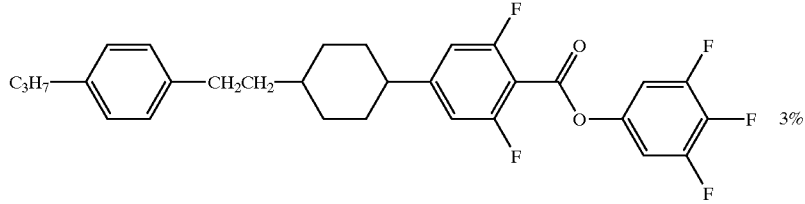 3%
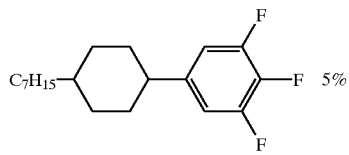 5%
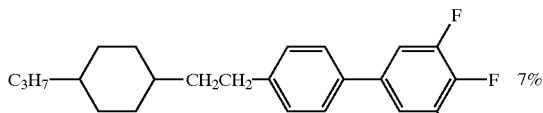 7%
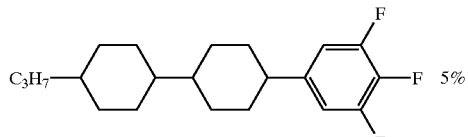 5%
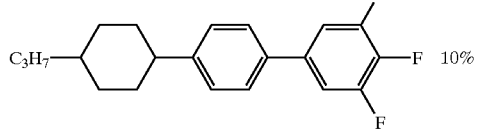 10%
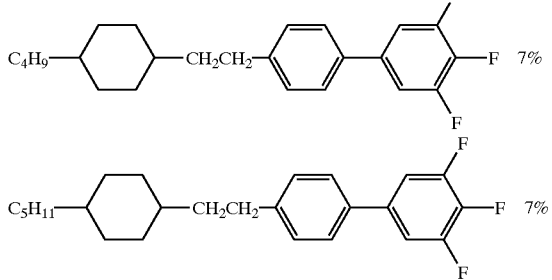 7%
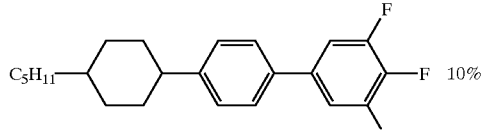 10%
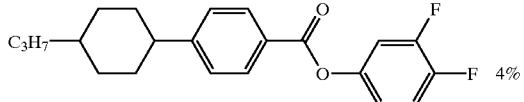 4%
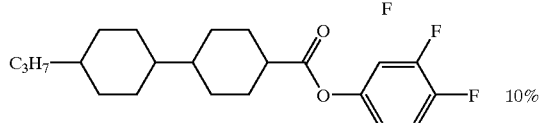 10%
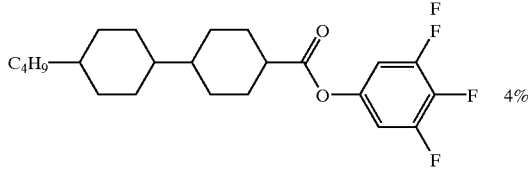 4%
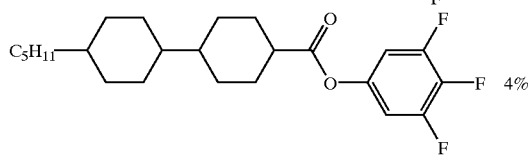 4%
Composition Example 8
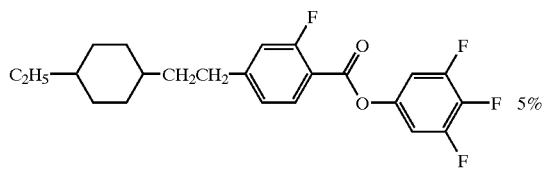 5%
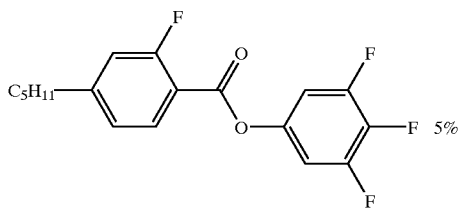 5%
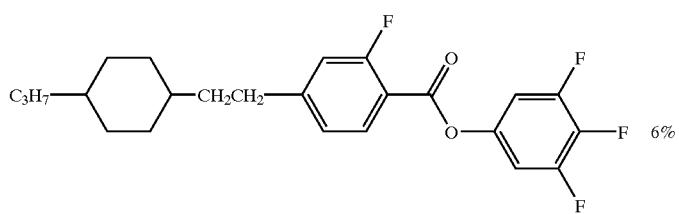 6%

-continued
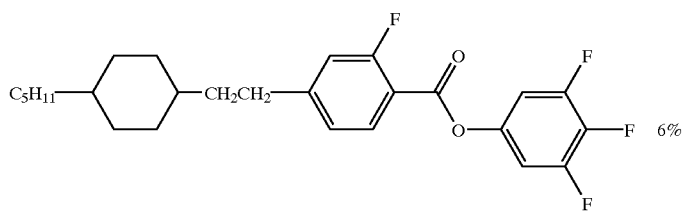 6%
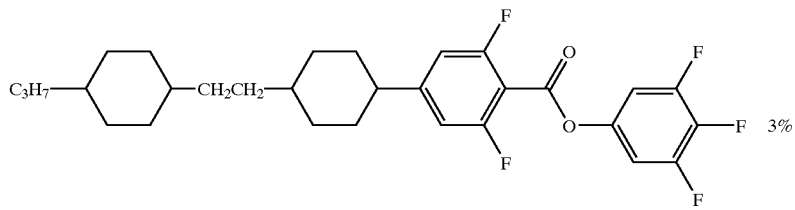 3%
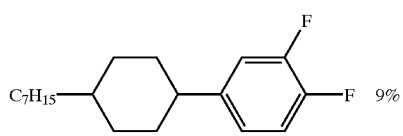 9%
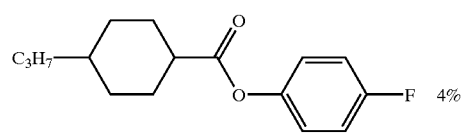 4%
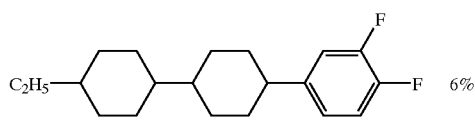 6%
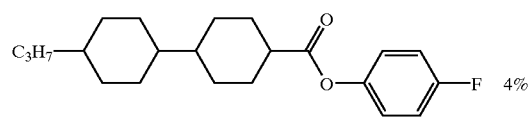 4%
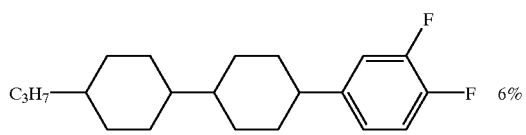 6%
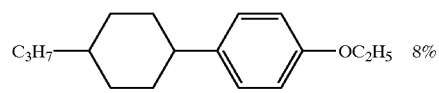 8%
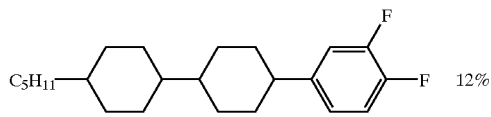 12%
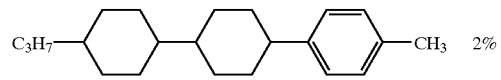 2%
 4%
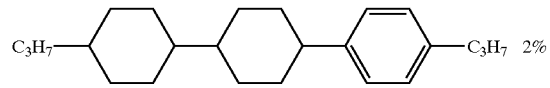 2%
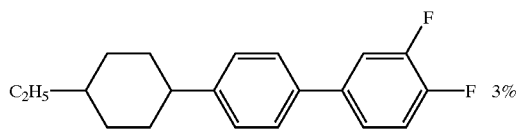 3%
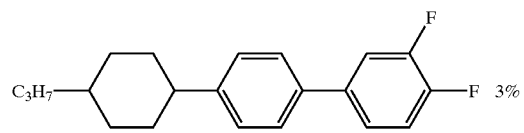 3%
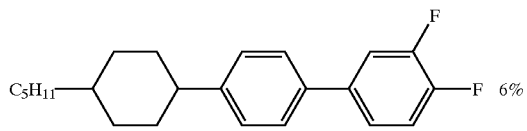 6%
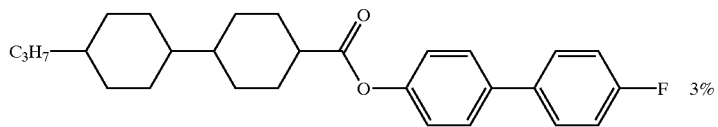 3%
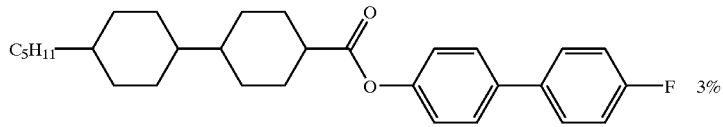 3%

Composition Example 9
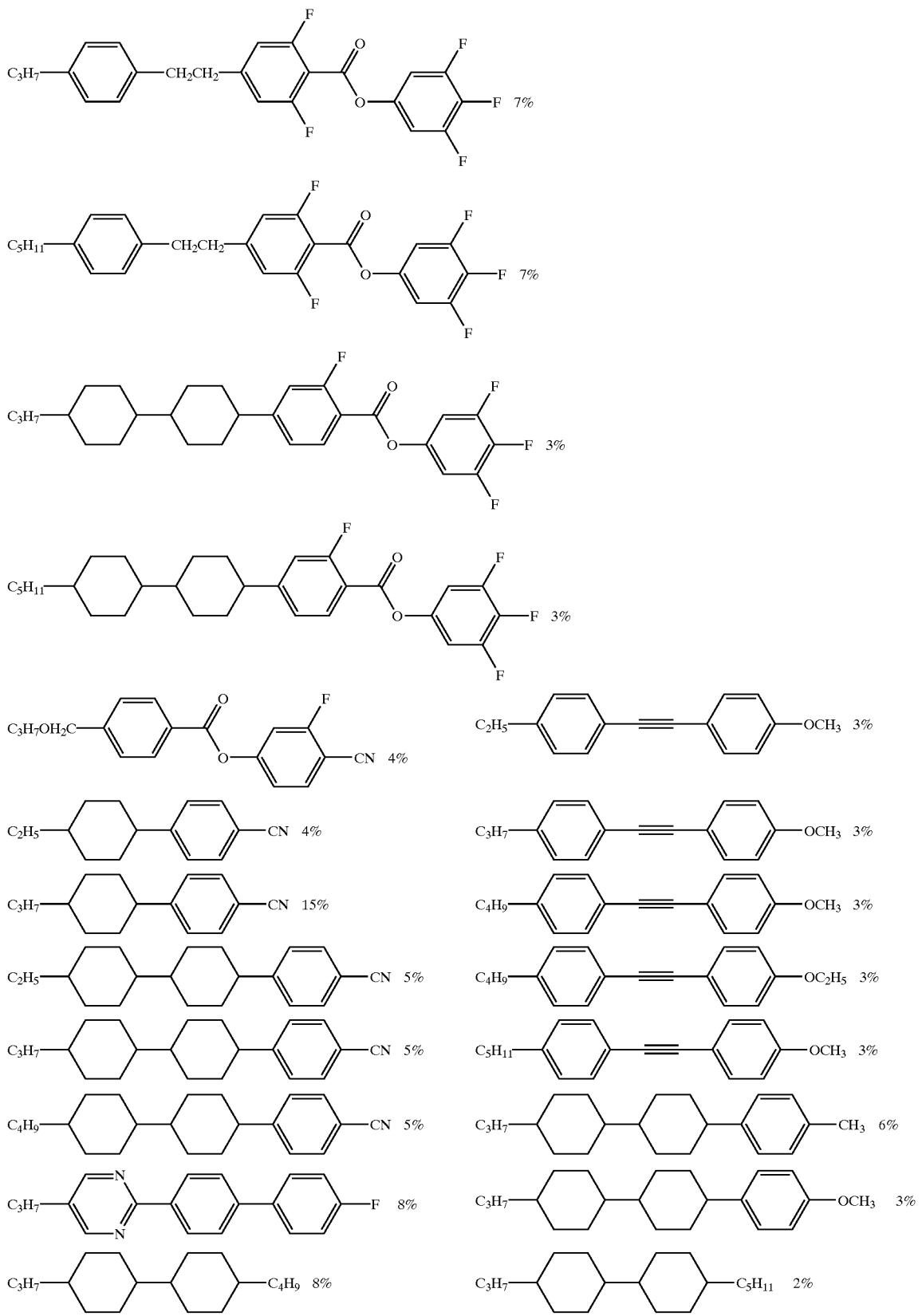

Composition Example 10
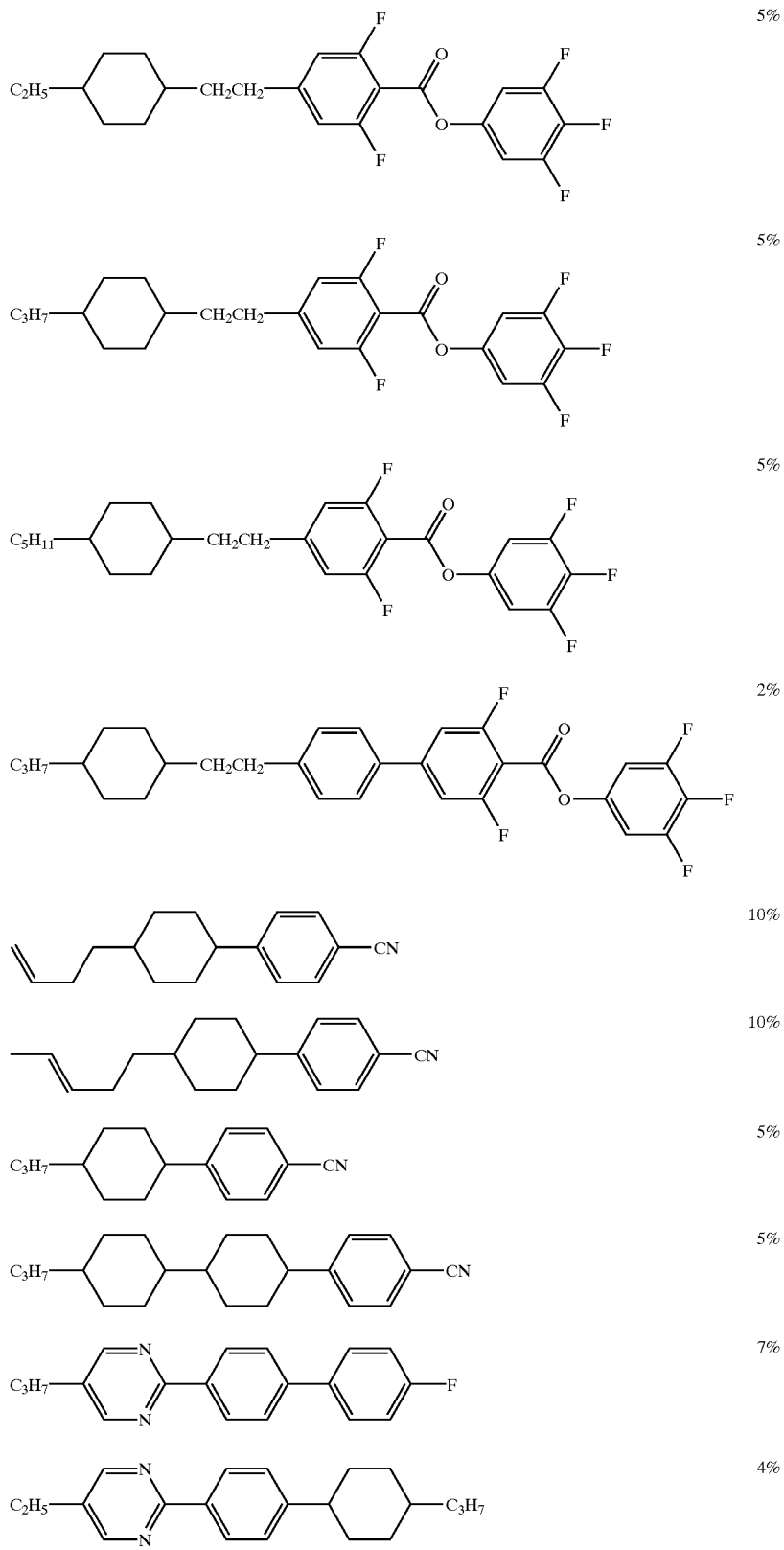

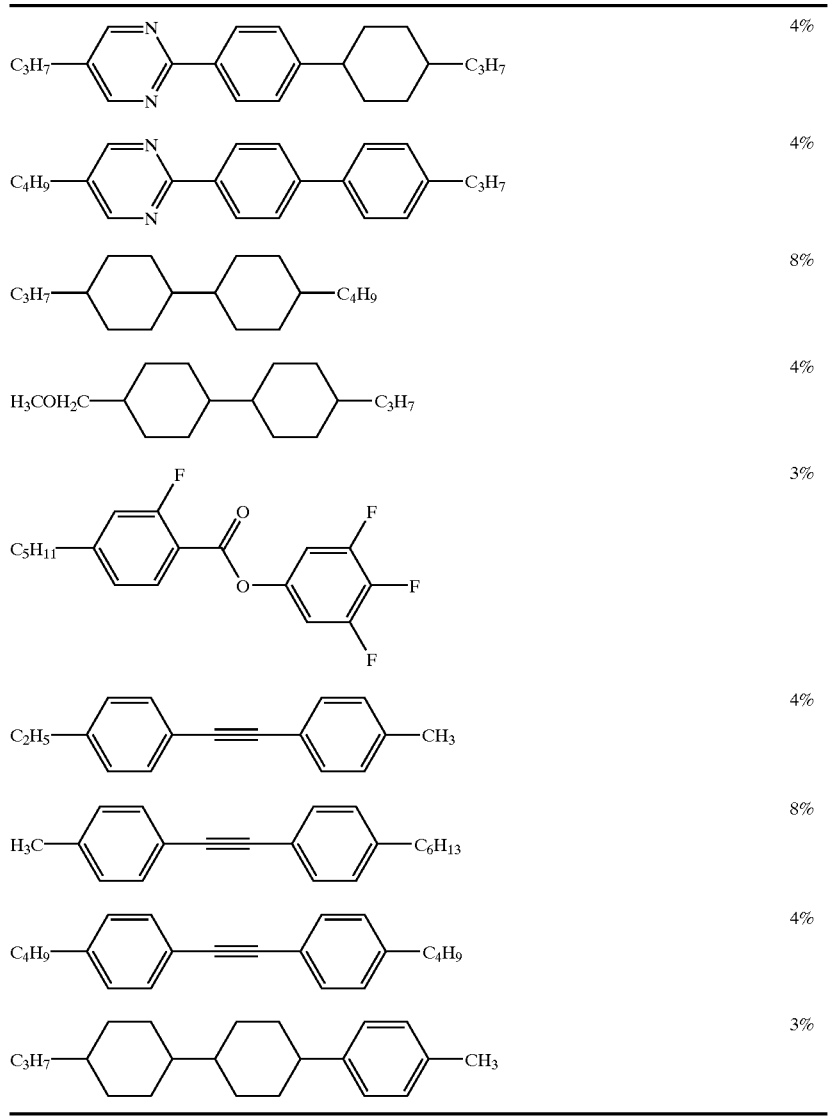
Composition Example 11
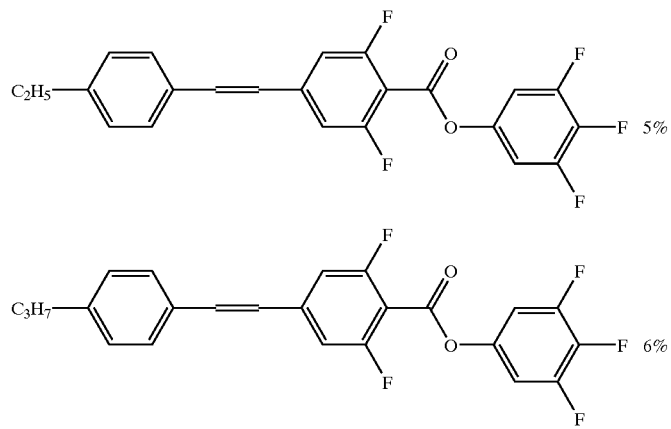

-continued
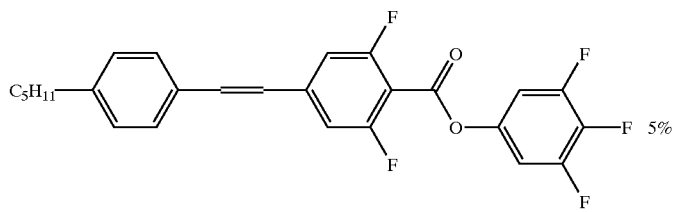 5%
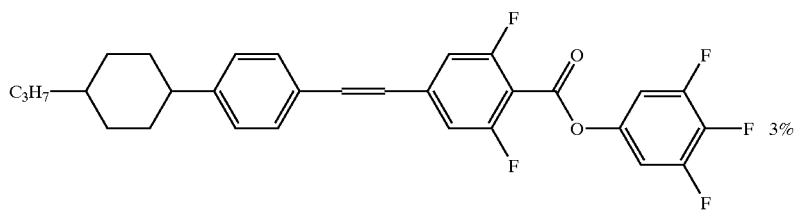 3%
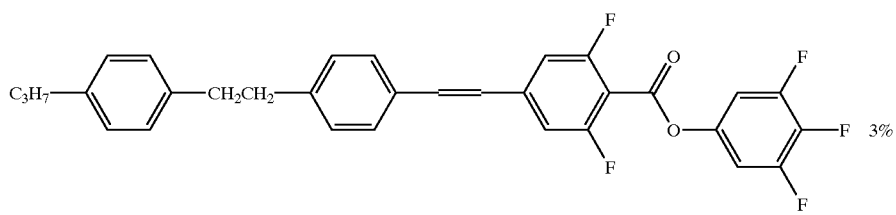 3%
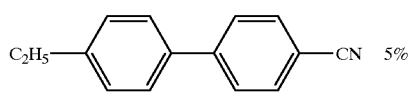 5%
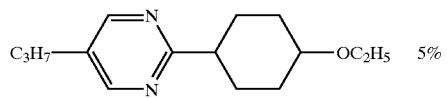 5%
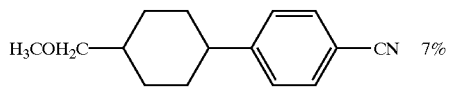 7%
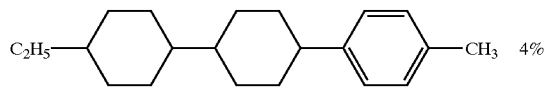 4%
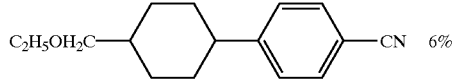 6%
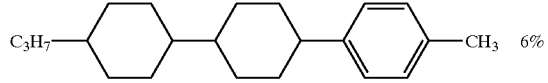 6%
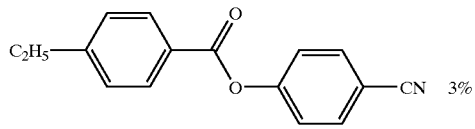 3%
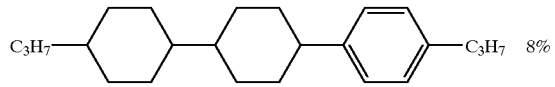 8%
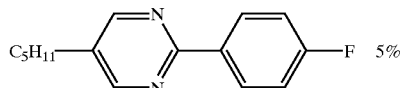 5%
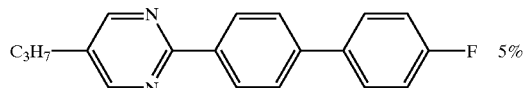 5%
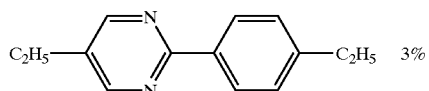 3%
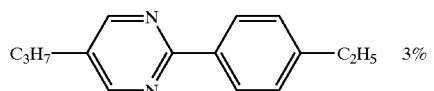 3%
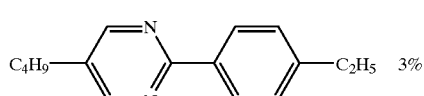 3%
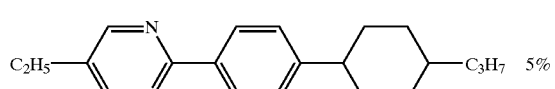 5%
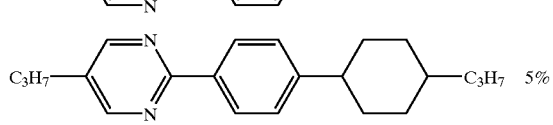 5%
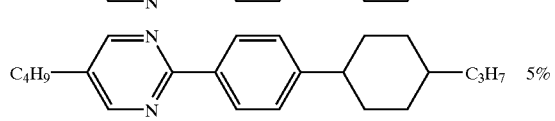 5%

Composition Example 12
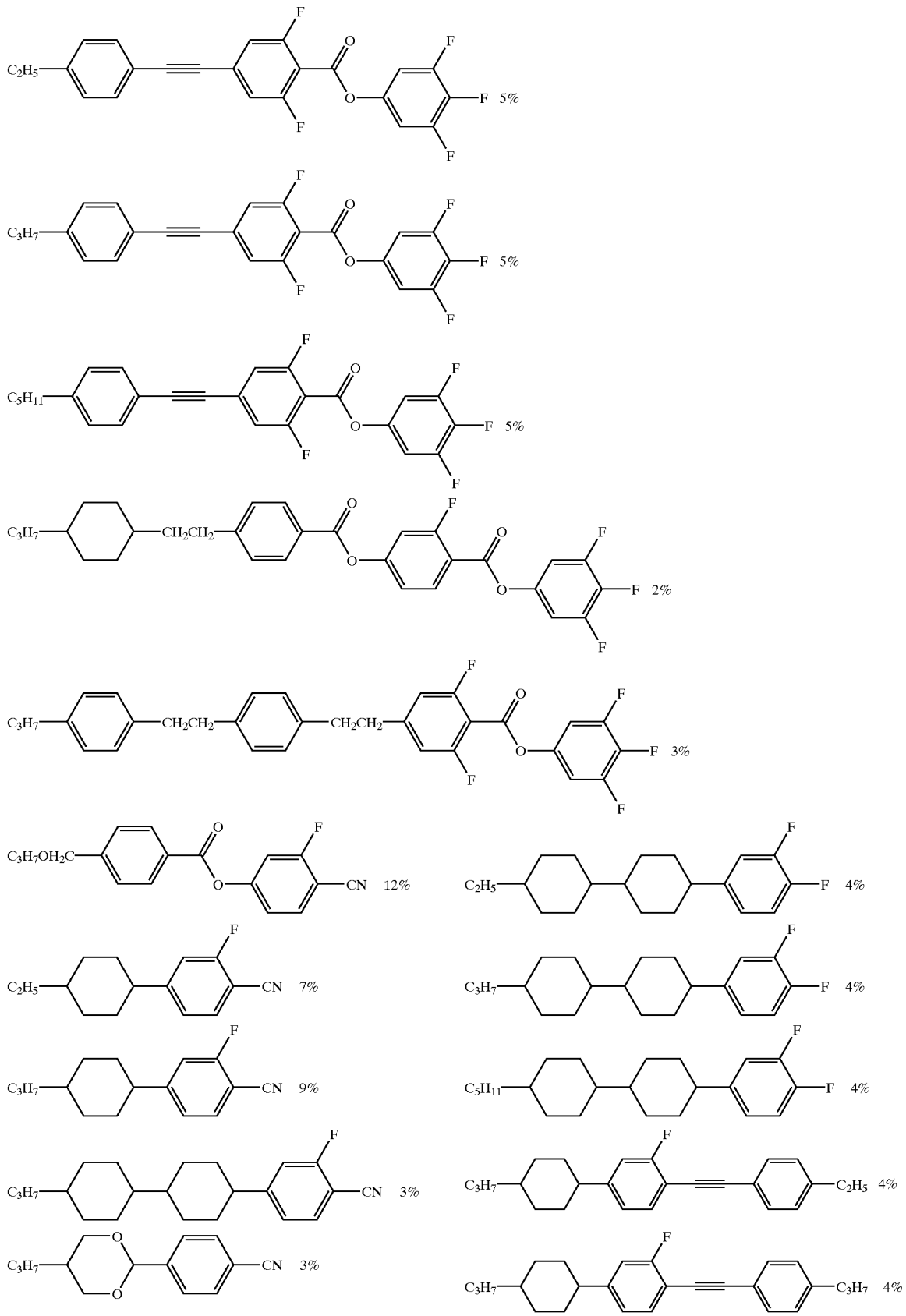

-continued
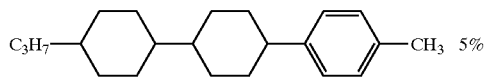 5%
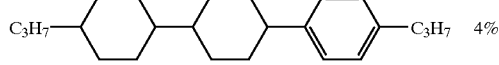 4%
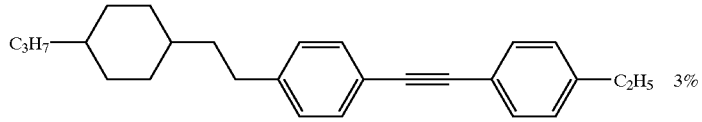 3%
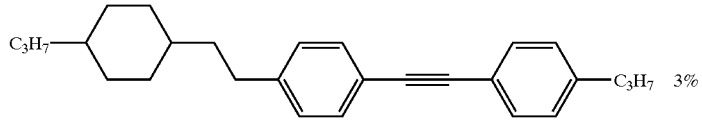 3%
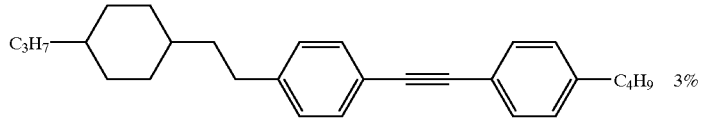 3%
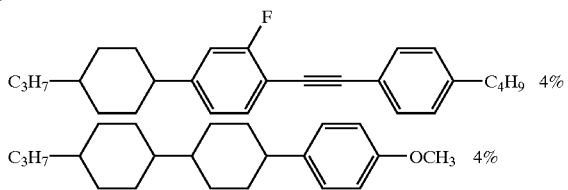 4%
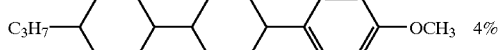 4%
Composition Example 13
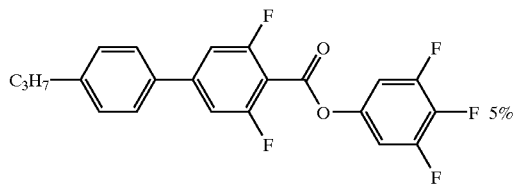 5%
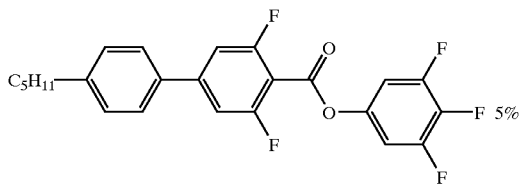 5%
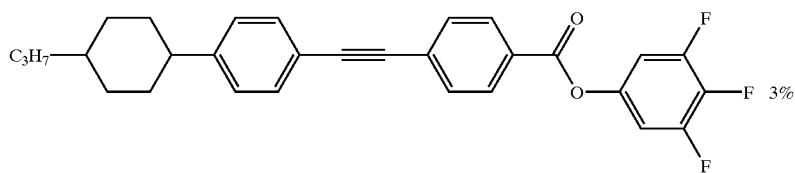 3%
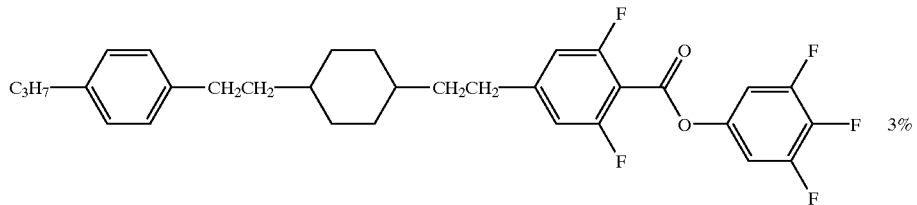 3%
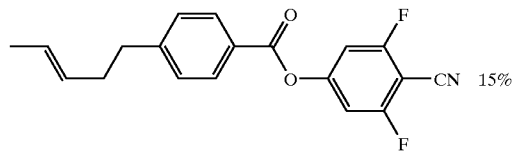 15%
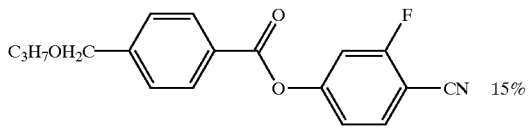 15%
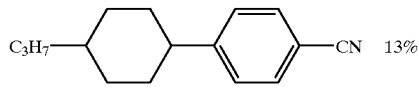 13%
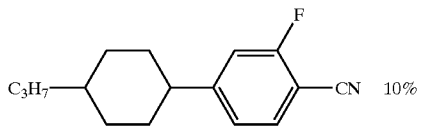 10%
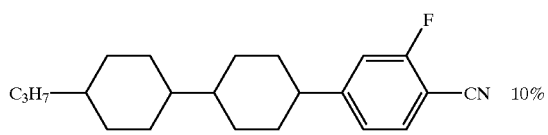 10%
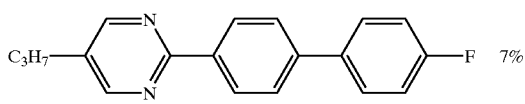 7%

-continued
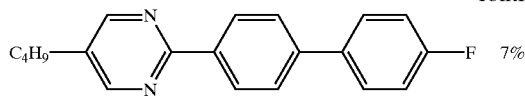 7%
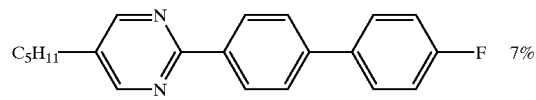 7%
Composition Example 14
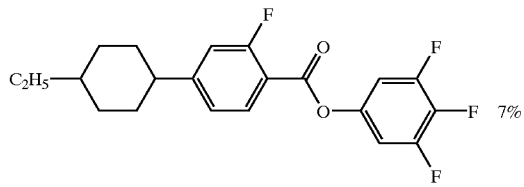 7%
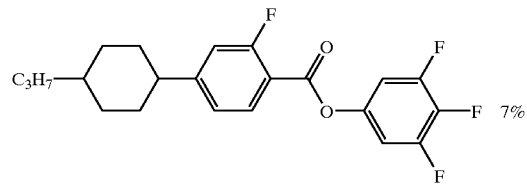 7%
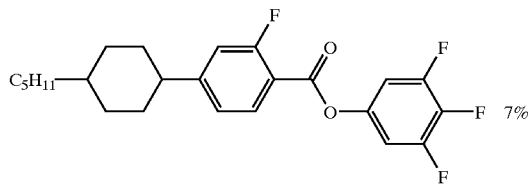 7%
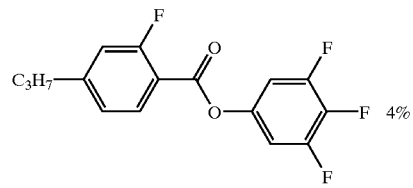 4%
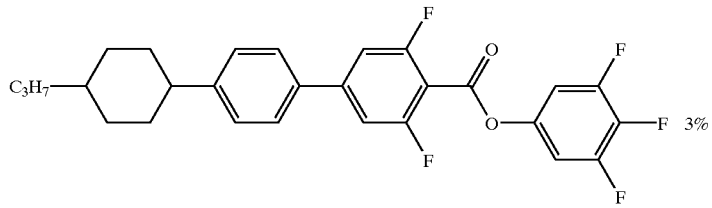 3%
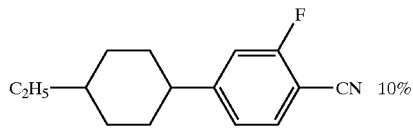 10%
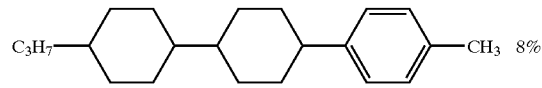 8%
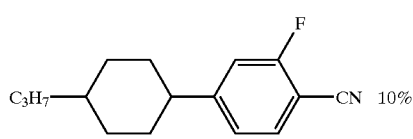 10%
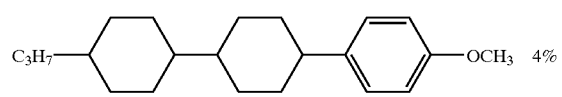 4%
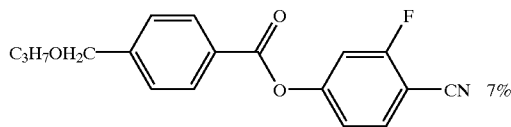 7%
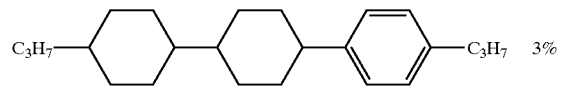 3%
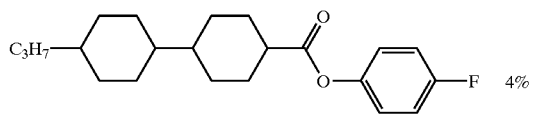 4%
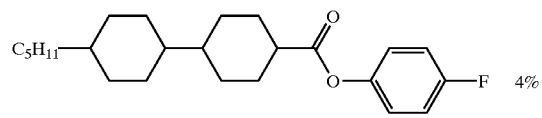 4%
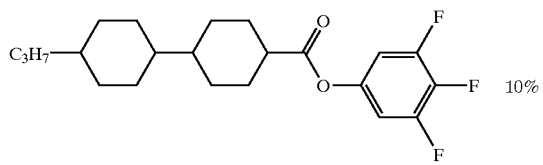 10%
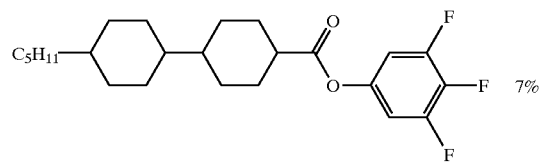 7%
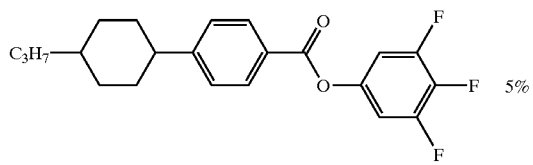 5%

Composition Example 15
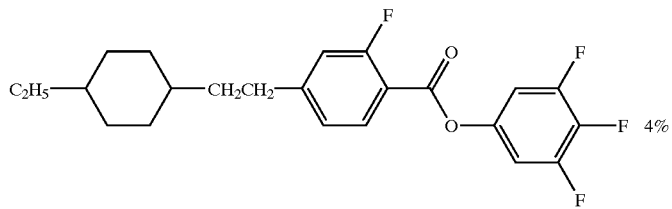 4%
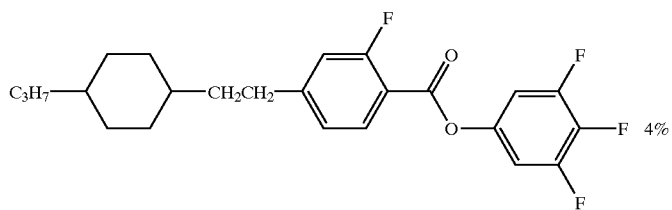 4%
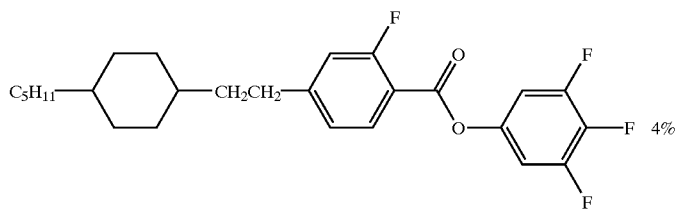 4%
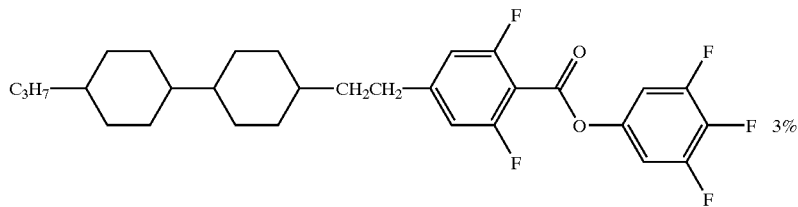 3%
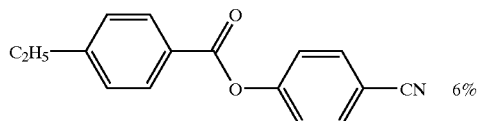 6%
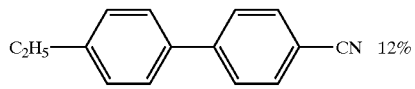 12%
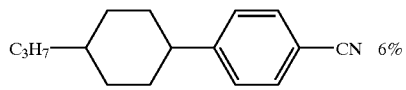 6%
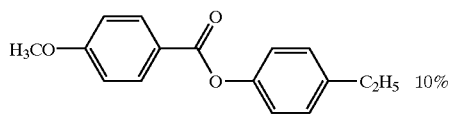 10%
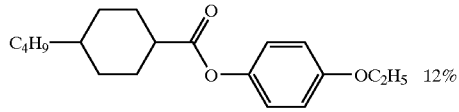 12%
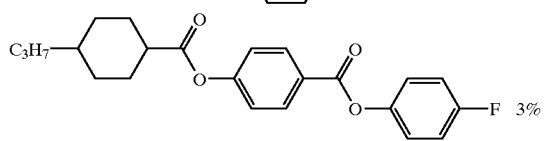 3%
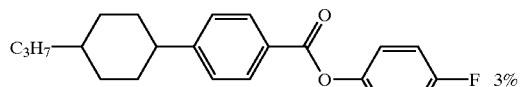 3%
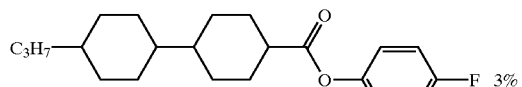 3%
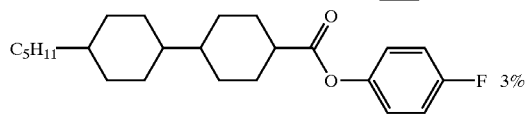 3%
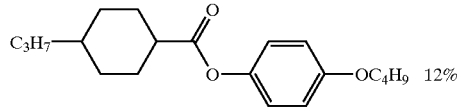 12%
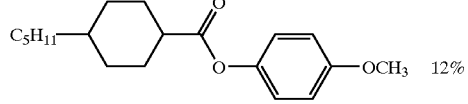 12%
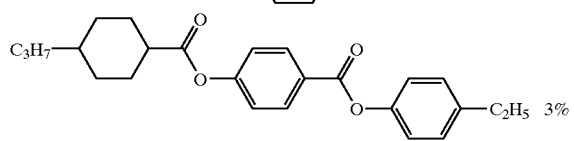 3%

Composition Example 16
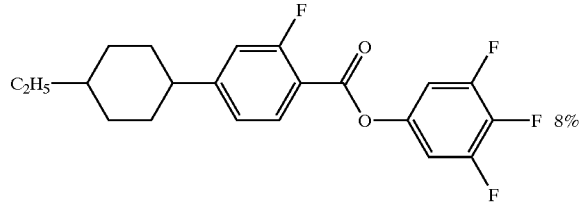 8%
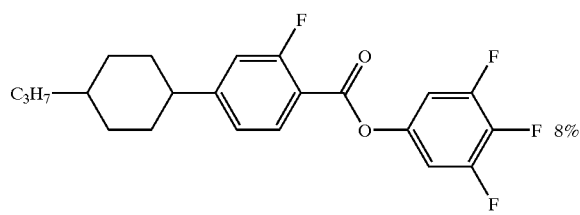 8%
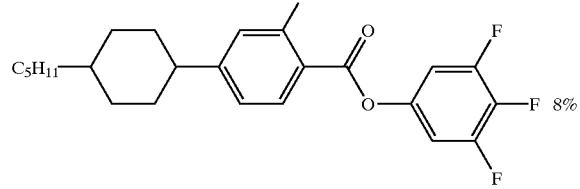 8%
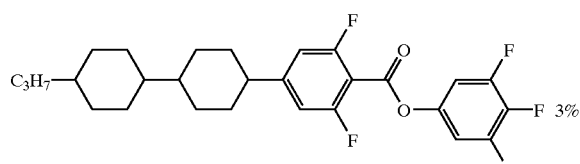 3%
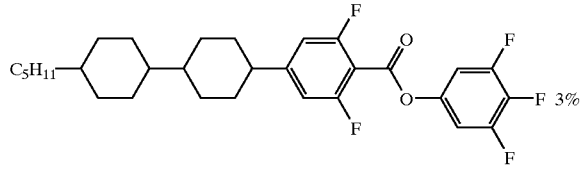 3%
 4%
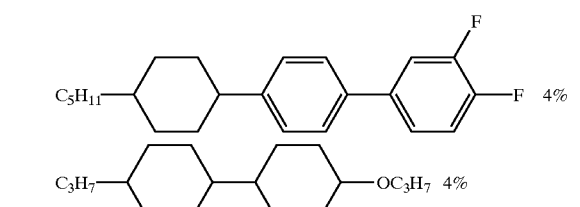 4%
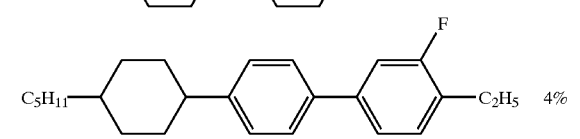 4%
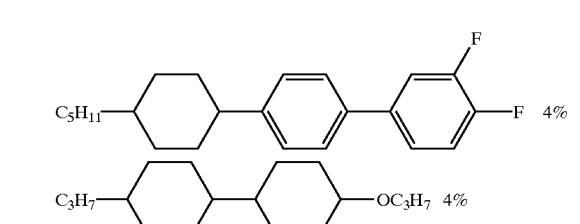 4%
-continued
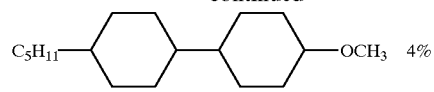 4%
 4%
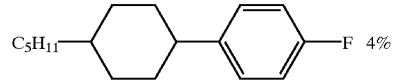 4%
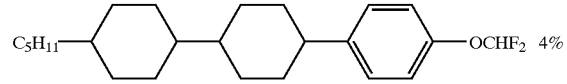 4%
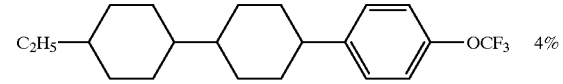 4%
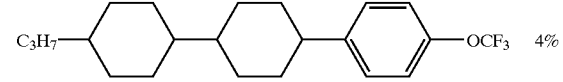 4%
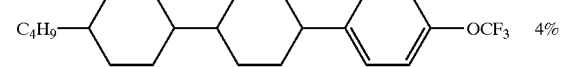 4%
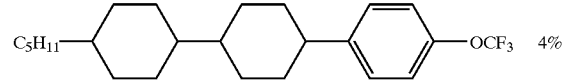 4%
 5%
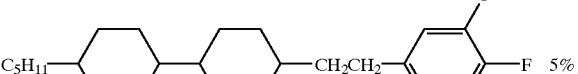 5%
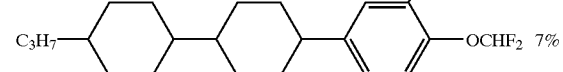 7%
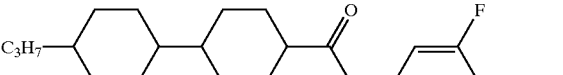 5%

Composition Example 17
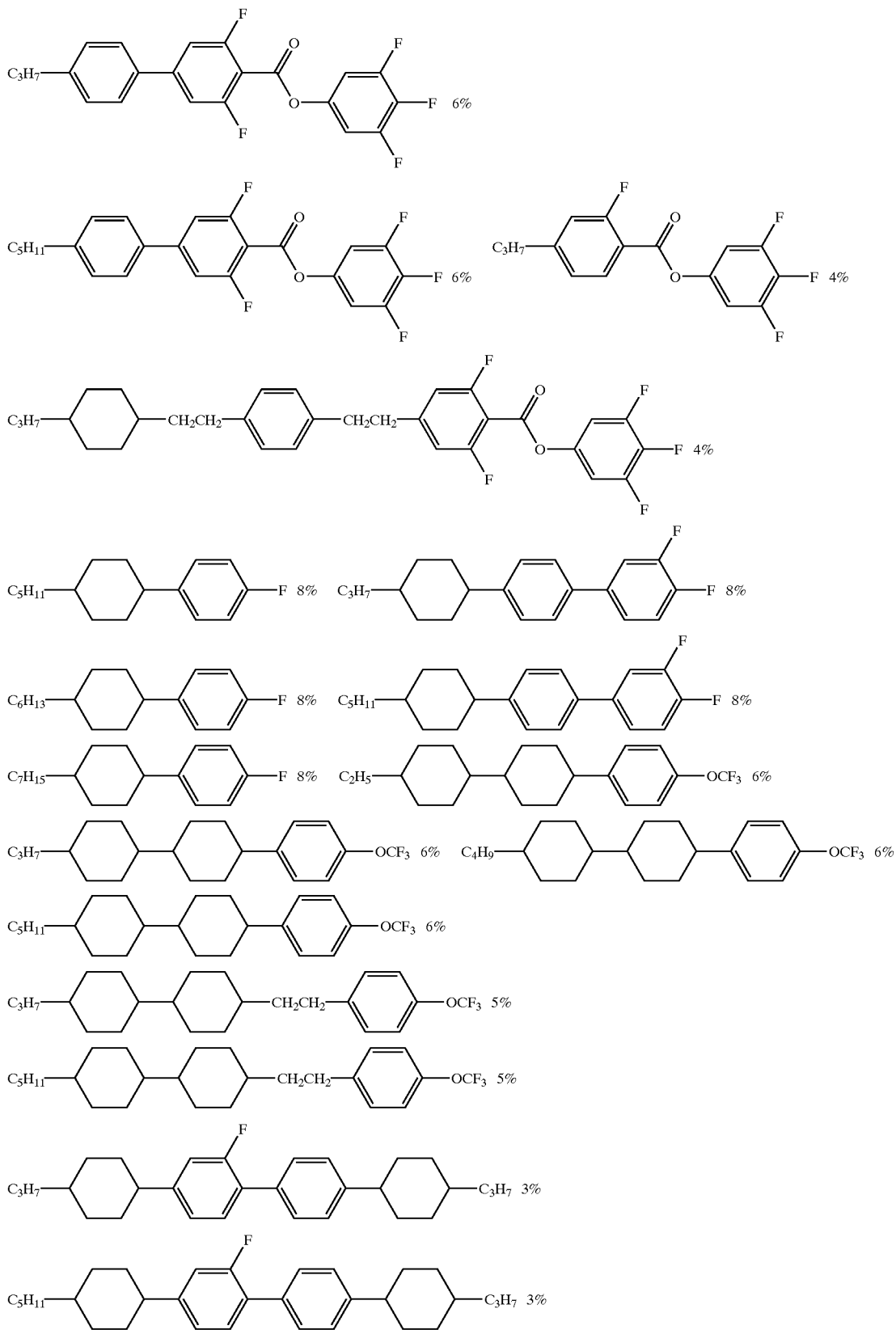

Composition Example 18
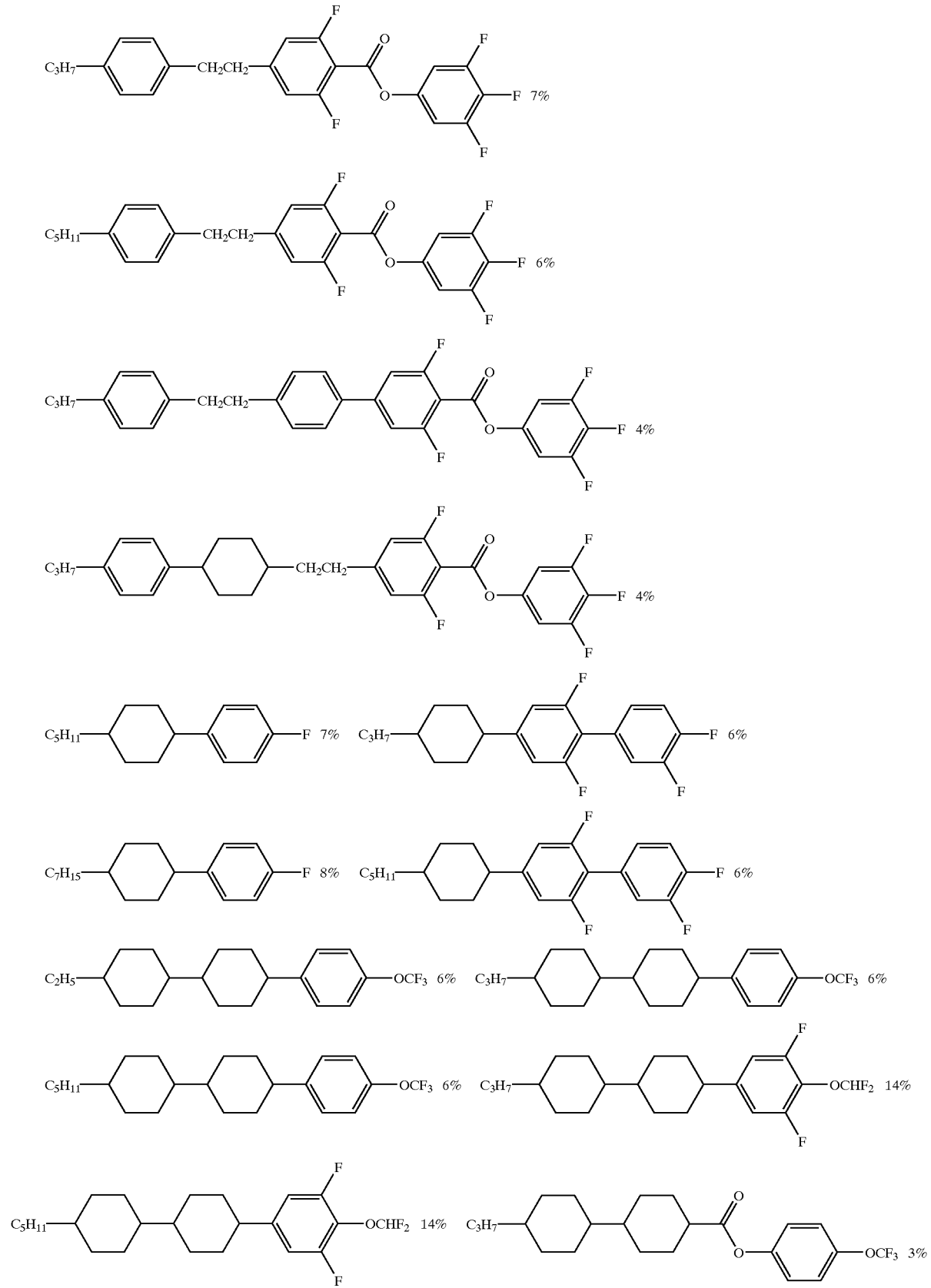

-continued
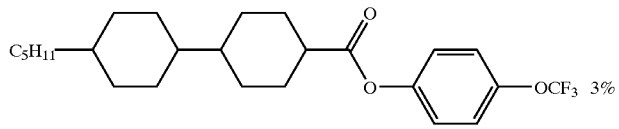 3%
Composition Example 19
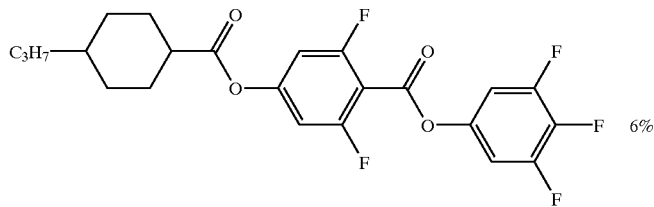 6%
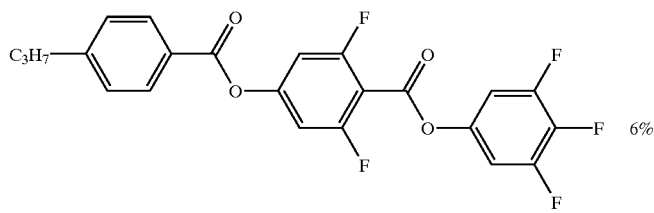 6%
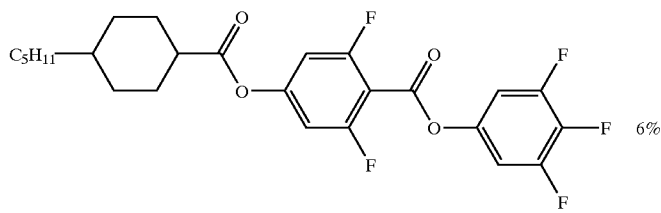 6%
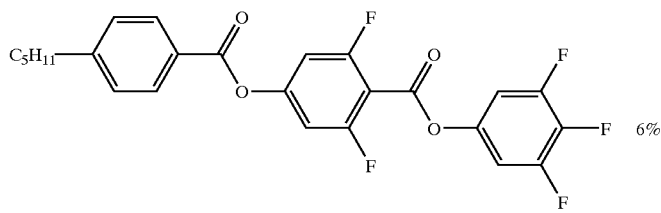 6%
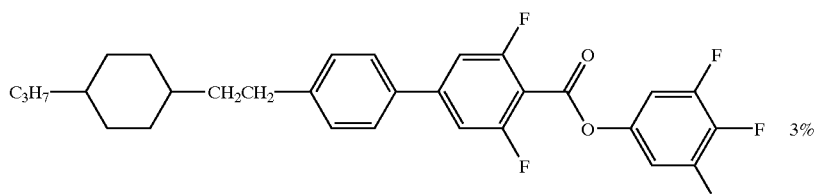 3%
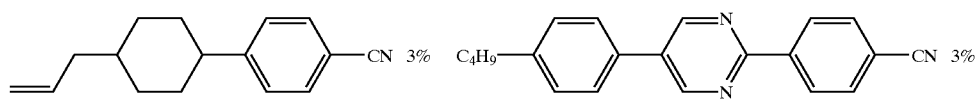
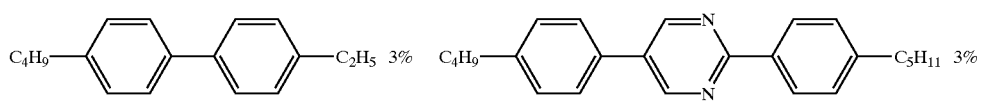
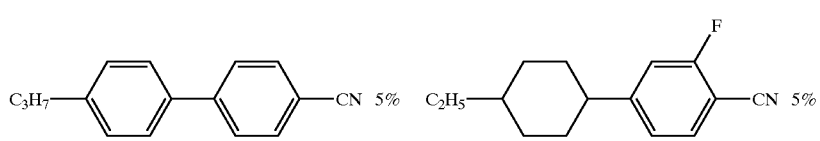

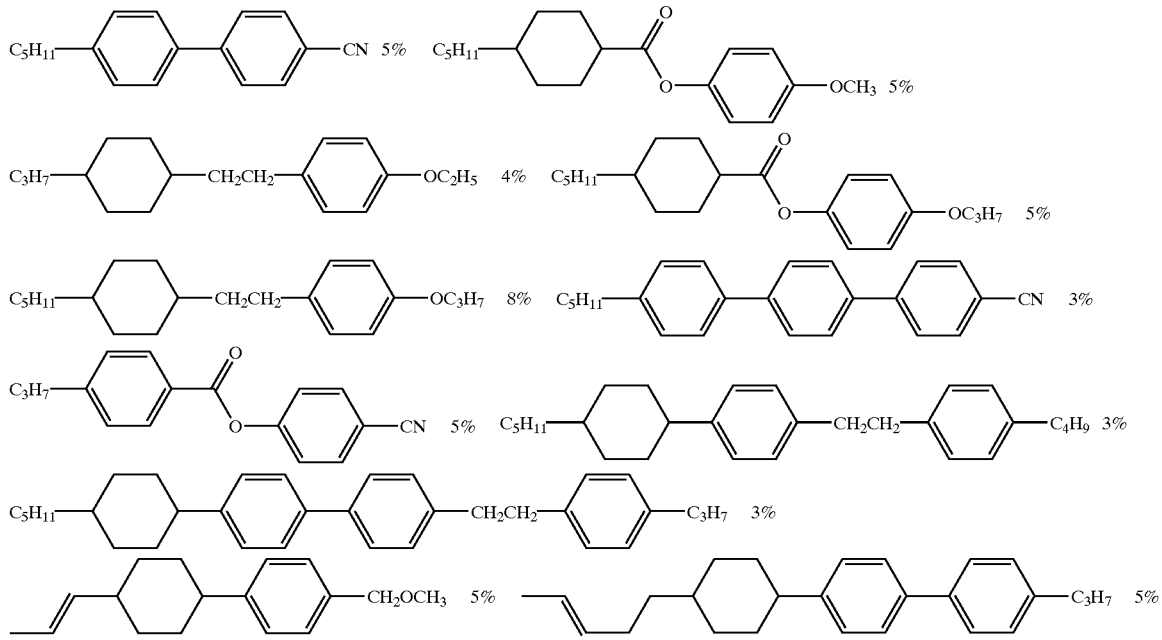
Composition Example 20
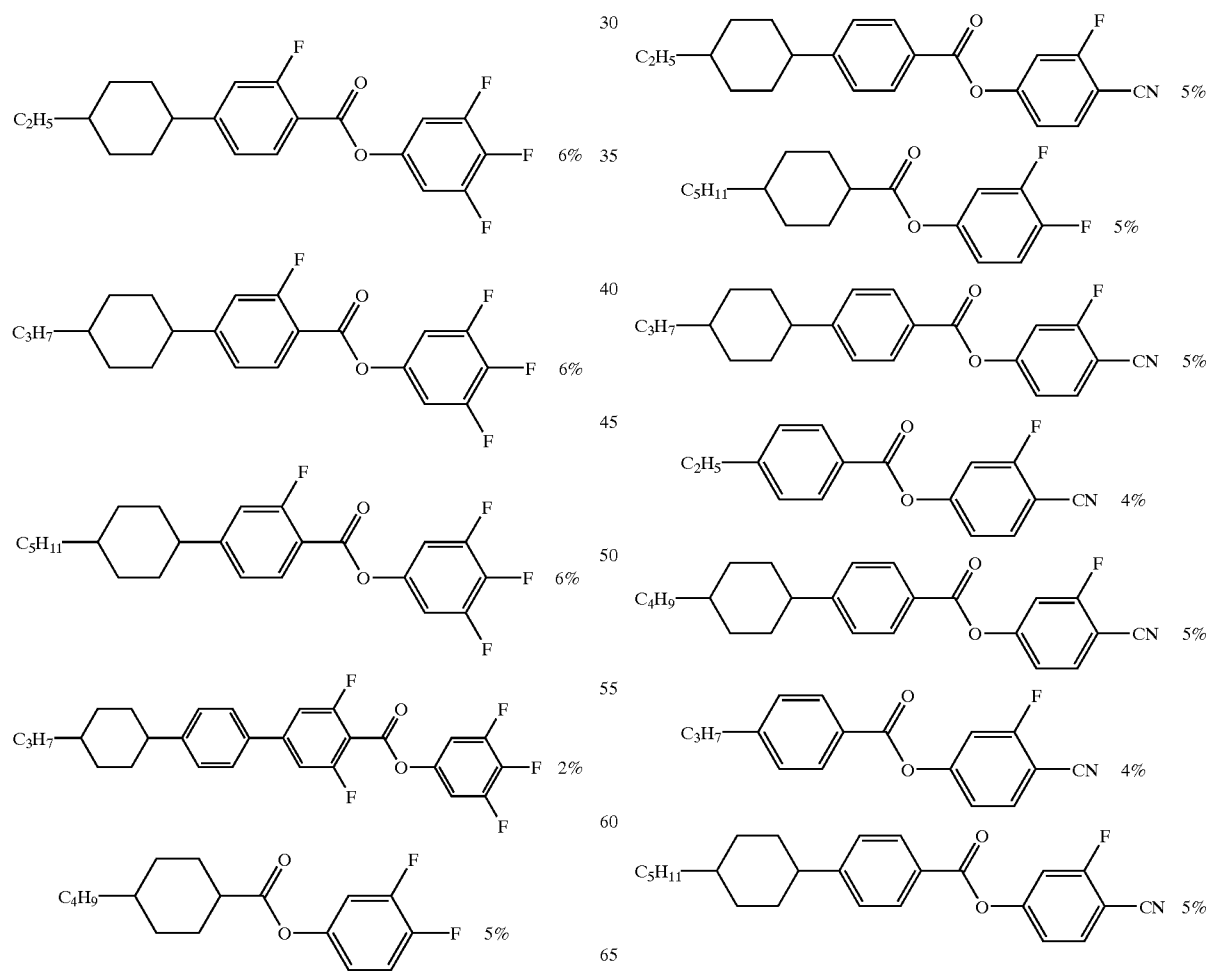

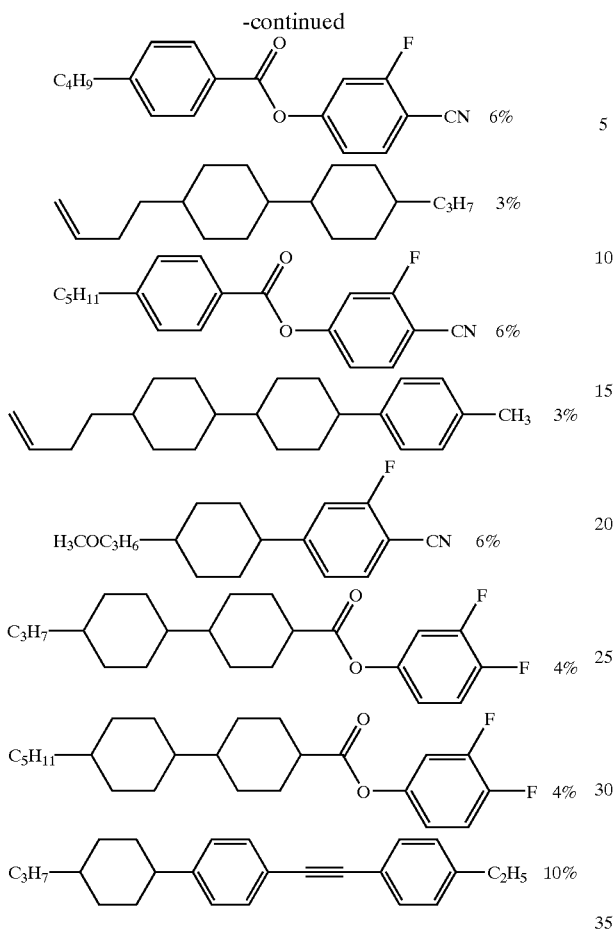

(Process for the Preparation of the Present Phenylbenzoate Derivatives)

For example, the preferred compounds represented by formula (1-a) can be prepared by reacting a lithium reagent generally known such as an alkyl lithium with 3-fluoroalkylbenzenes (1) to introduce lithium at the 4-position thereof, followed by reacting with a formylating agent such as formylpiperidine or N,N-dimethylformamide to form the corresponding aldehyde derivative and subsequently reacting with a suitable oxidizing agent to afford the corresponding carboxylic acid derivative (2).

Alternatively, the carboxylic acid derivative (2)g may be prepared by reacting the lithium derivative with $CO_2$. Alternatively, an acid chloride derivative of the compound (2) may be prepared by reacting the compounds (1) with oxalyl chloride according to Friedel-Crafts reaction. Subsequently, the carboxylic acid derivative (2) can be reacted with 3,4,5-trifluorophenol, in accordance with a general esterification process, for example, using as an acid catalyst, a mineral acid such as hydrochloric acid, sulfuric acid, an organic acid such as p-toluenesulfonic acid, a nonaqueous ion exchange resin such as Amberlite, or as a catalyst N,N-dicyclohexylcarbodiimide (DCC) to prepare the compounds (1-a). Alternatively, the compounds (1-a) may be prepared by reacting the compound (2) with thionyl chloride to form the corresponding acid chloride, followed by the reaction with 3,4,5-trifluorophenol in the presence of a base such as pyridine.

One of the starting materials, 3,4,5-trifluoro-phenol can be prepared using 3,4,5-trifluorobromobenzene as a starting material. More specifically, a Grignard reagent prepared from 3,4,5-trifluorobromobenzene is reacted with t-butyl hydroperoxide according to the method by S. O. Lawesson et al. (J. Am. Chem. Soc., 81, 4230(1959)), or the Grignard reagent is treated with a trialkyl borate to form the corresponding borate derivative and then oxidized with hydrogen peroxide aqueous solution according to the method by R. L. Kidwell et al. (Org. Synth., V, 918(1973)).

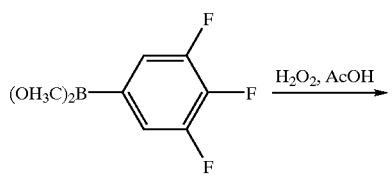

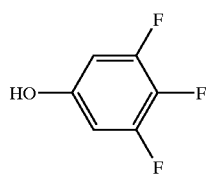

The compounds represented by formula (1-b) can be prepared according to the following reaction route. For the preparation of the compounds (1-b-1), alkyl substituted cyclohexanones (3) are reacted with a Grignard reagent prepared from a 3-fluorobromobenzene derivative (4) to form the corresponding alcohol derivatives (5), which are dehydrated using as an acid catalyst, a mineral acid such as 5 hydrochloric acid, sulfuric acid, an organic acid such as p-tolenesulfonic acid, a nonaqueous ion exchange resin such as Amberlite; followed by a catalytic hydrogenation in the presence of a noble metal catalyst such as Pt, Rh, and Pd to afford 1-(4-alkylcyclohexyl)-3-fluorobenzene derivatives (6). The compounds (1-b-1) can be prepared in the same manner as described above for the preparation of the compounds (1-a), by forming the corresponding carboxylic acid derivatives via the formation of the lithium derivative, followed by esterification with 15 3,4,5-trifluorophenol.

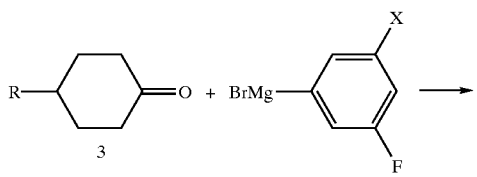

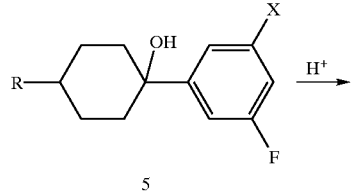

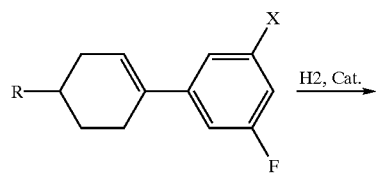

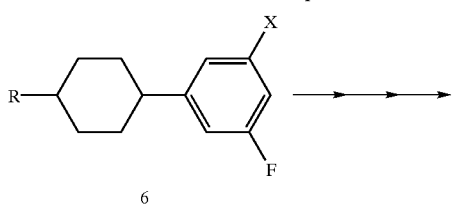

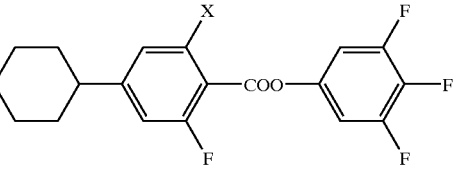

For the preparation of the compounds (1-b-2), 3-fluorophenol derivatives (7) as a starting material are reacted with sodium hydride, followed by protecting the phenolic hydroxyl group with chloromethyl methyl ether or the like to give the intermediates (8). The compounds (8) are treated in the same manner as described above for the preparation of the compounds (1-a) to give the ester intermediates (9). The compounds (9) are deprotected in the presence of a mineral acid such as hydrochloric acid, sulfuric acid, etc., and then reacted with an acid chloride prepared from the reaction of alkylcyclohexycarboxylic acids (11) and thionyl chloride in the presence of pyridine.

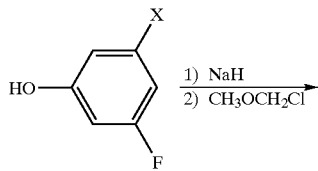

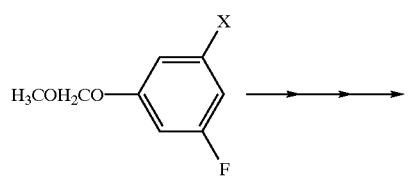

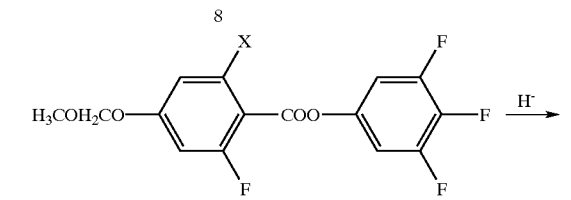

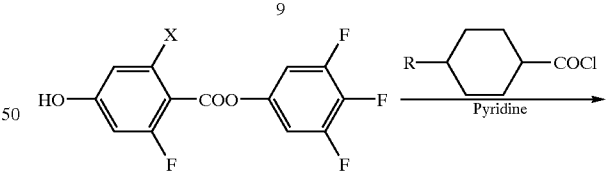

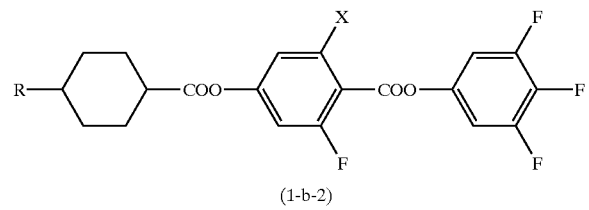

For the preparation of the compounds (1-b-3), the corresponding ylide compound prepared by reacting ethyl diethylphosphinoacetate with a base such as an alkyl lithium, sodium alcoholate, potassium t-butoxide, etc. is reacted with alkyl substituted cyclohexanones (3) to form intermediates

(12) having two carbon atoms increased, the olefin moiety is reduced by catalytic hydrogenation in the presence of a noble metal catalyst such as Pt, Rh, Pd, etc. and further the ester moiety is reduced with lithium aluminum hydride to give the corresponding alcohol derivatives (13). The derivatives (13) are reacted with pyridinium chlorochromate (PCC) or subjected to DMSO oxidation (Swern oxidation) to give the corresponding aldehyde derivatives (14). The derivatives (14) are reacted with a Grignard reagent prepared from the compounds (4) to form the alcohol products (15) which are then dehydrated using as an acid catalyst a mineral acid such as hydrochloric acid, sulfuric acid, etc., an organic acid such as p-toluenesulfonic acid, etc. or a non-aqueous ion exchange resin such as Amberlite, etc. and further subjected to catalytic hydrogenation in the presence of a noble catalyst such as Pt, Rh, Pd, etc. to prepare 1-(4-alkylcyclohexyl)-2-(3-fluorophenyl)ethanes (16). The compounds (16) can be treated in the same manner as described above for the preparation of the compounds (1-a) to prepare the compounds (1-b-3).

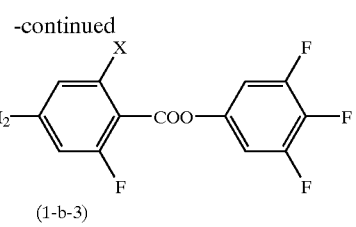

(1-b-3)

The compounds of formula (1-c) can be prepared according to the following reaction route. For the preparation of the compounds (1-c-1), a starting material, 4-alkyliodobenzenes (17) are reacted with a Grignard reagent prepared from the compounds (4) in the presence of a catalyst such as palladium chloride, etc. to form the corresponding biphenyl derivatives (18). The derivatives (18) can be treated in the same manner as described above for the preparation of the compounds (1-a) to prepare the compounds (1-c-l). Further, the compounds (1-c-2) can be prepared by esterification of the above compounds (10) with 4-alkyl substituted benzoic acid derivatives (19). For the preparation of the compounds (1-c-3) and (1-c-4), a starting material, 3-fluorobenzaldehydes (20) are protected for the aldehyde moiety with ethylene glycol in the presence of an acid catalyst and then treated in the same manner as described for the preparation of the compounds (1-a) to form the corresponding ester products (22). The ester products (22) are deprotected in the presence of an acid catalyst such as formic acid, acetic acid, etc. to form the compounds (23) which are then coupled with a Wittig reagent prepared from a 4-alkylbenzyl iodide to prepare the compounds (1-c-4). Subsequently, the compounds (1-c-4) can be subjected to catalytic hydrogenation in the presence of a noble catalyst such as Pt, Rh, Pd, etc. to prepare the compounds (1-c-3).

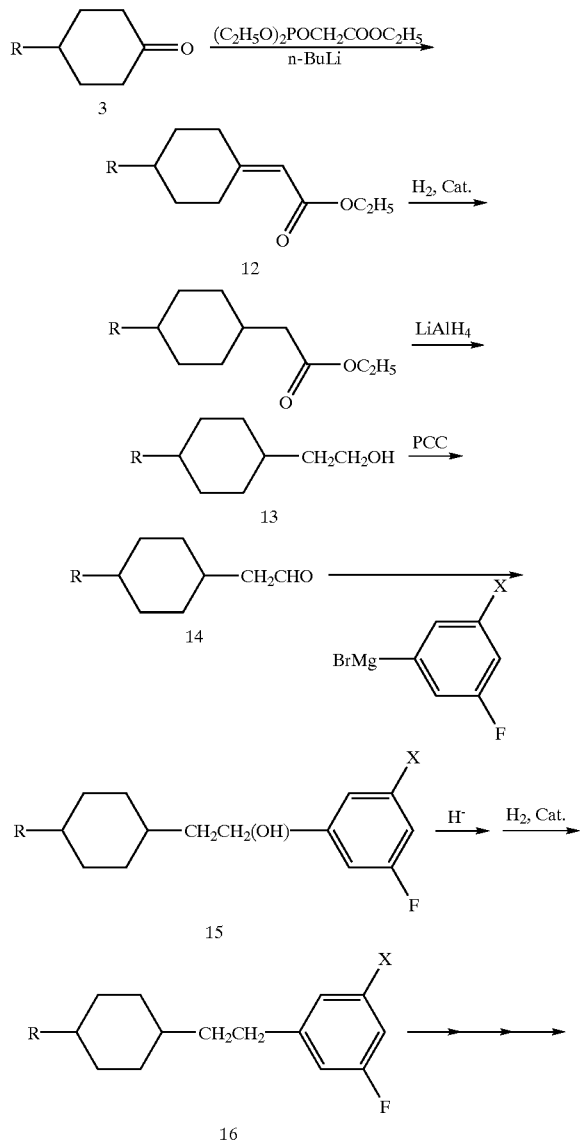

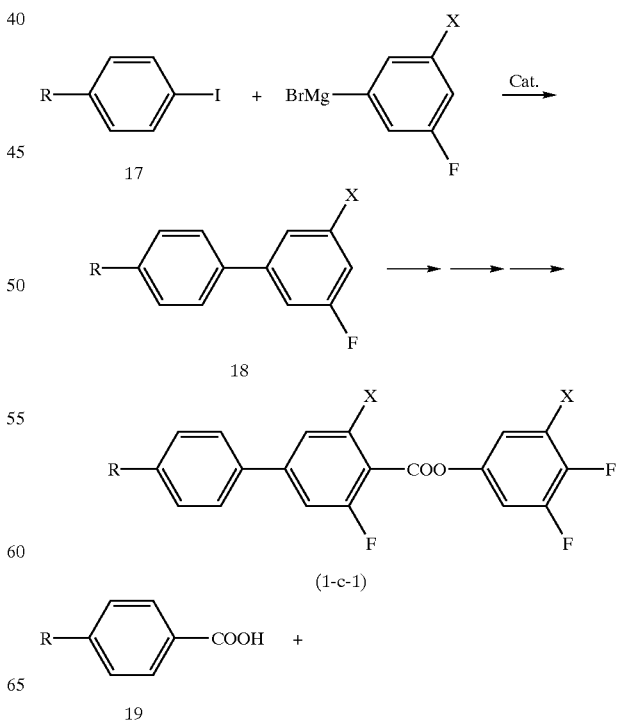

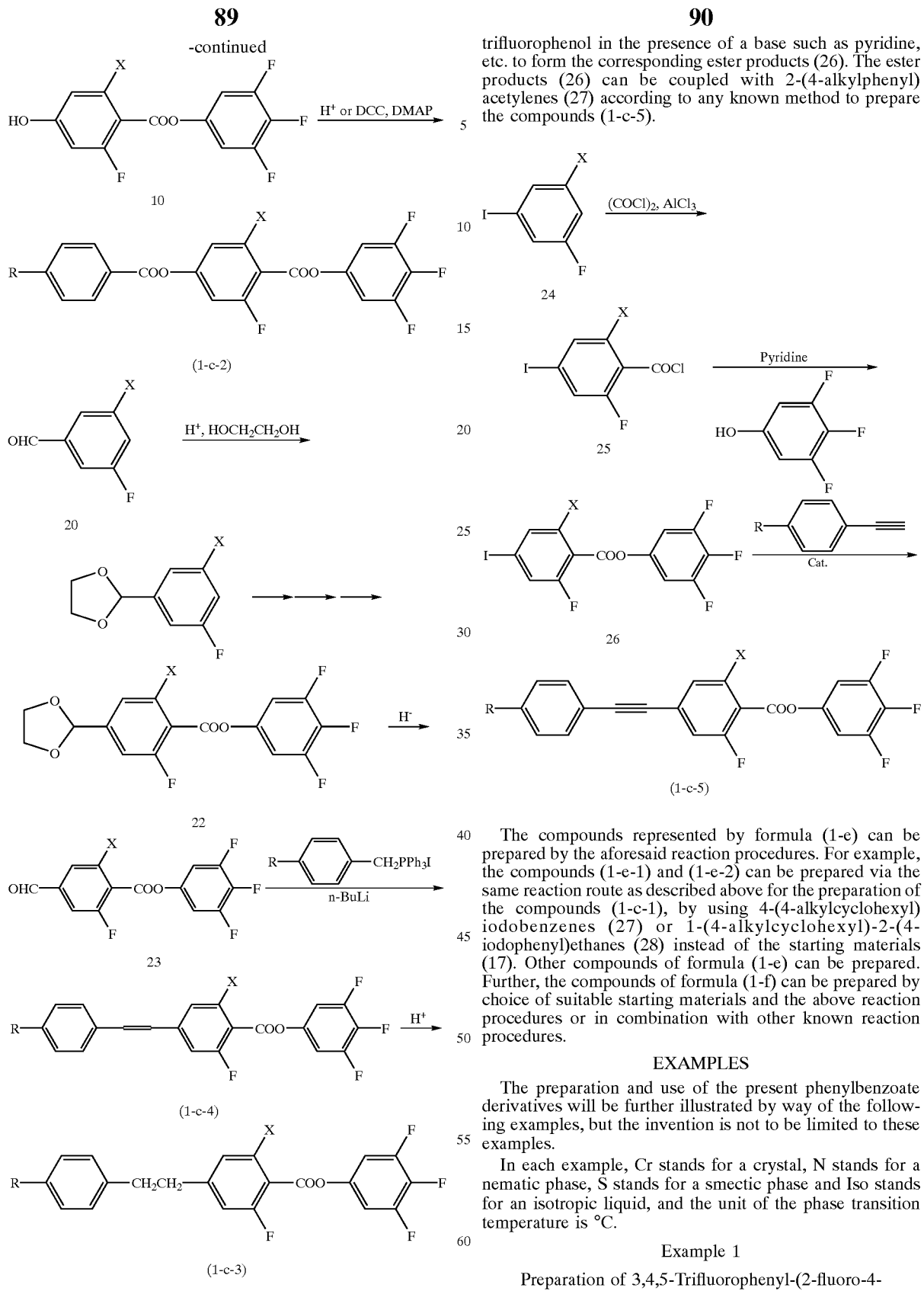

trifluorophenol in the presence of a base such as pyridine, etc. to form the corresponding ester products (26). The ester products (26) can be coupled with 2-(4-alkylphenyl)acetylenes (27) according to any known method to prepare the compounds (1-c-5).

For the preparation of the compounds (1-c-5), 3-fluoroiodobenzene derivatives (24) are reacted with oxalyl chloride according to Friedel-Crafts reaction to form the corresponding acid chloride (25) which is then reacted with The compounds represented by formula (1-e) can be prepared by the aforesaid reaction procedures. For example, the compounds (1-e-1) and (1-e-2) can be prepared via the same reaction route as described above for the preparation of the compounds (1-c-1), by using 4-(4-alkylcyclohexyl)iodobenzenes (27) or 1-(4-alkylcyclohexyl)-2-(4-iodophenyl)ethanes (28) instead of the starting materials (17). Other compounds of formula (1-e) can be prepared. Further, the compounds of formula (1-f) can be prepared by choice of suitable starting materials and the above reaction procedures or in combination with other known reaction procedures.

EXAMPLES

The preparation and use of the present phenylbenzoate derivatives will be further illustrated by way of the following examples, but the invention is not to be limited to these examples.

In each example, Cr stands for a crystal, N stands for a nematic phase, S stands for a smectic phase and Iso stands for an isotropic liquid, and the unit of the phase transition temperature is °C.

Example 1

Preparation of 3,4,5-Trifluorophenyl-(2-fluoro-4-propyl)benzoate (the Compound of Formula (1) wherein $R_1$=n—$C_3H_7$, m=n=0, $Z_1$ and $Z_2$ are a Covalent Bond and X=H)

The preparation steps are divided into two steps of 1) the preparation of a benzoic acid derivative via the formation of the lithium intermediate and 2) the esterification. Each of the preparation steps will be explained below in detail.

1) Preparation of 2-Fluoro-4-propylbenzoic Acid

In a 300 ml three-necked flask equipped with a thermometer, a nitrogen gas inlet tube and a dropping funnel, 25.0 g (0.18 mol) of 3-fluoropropylbenzene was dissolved in 100 ml of tetrahydrofuran (hereinafter abbreviated as THF), the solution was cooled to −50° C. or lower on an acetone-dry ice refrigerant bath while stirring with a magnetic stirrer under nitrogen atmosphere. Then, 133 ml (0.21 mol) of a solution of n-butyl lithium in hexane (1.62 M soln.) was added dropwise over 30 minutes while maintaining at −50° C. or lower. After completion of the dropwise addition, stirring was continued over 2 hours while maintaining at the same temperature and then a solution of 30.5 g (0.27 mol) of 1-formylpiperidine in 30 ml of THF was added dropwise over 20 minutes while maintaining at −50° C. or lower. After completion of the dropwise addition, the solution was gradually elevated to room temperature over 40 minutes and 50 ml of a saturated aqueous solution of ammonium chloride was added dropwise to complete the reaction. The reaction product was extracted with diethyl ether (100 ml×3), washed with water (200 ml×3) and dried over anhydrous magnesium sulfate. The extract was concentrated under reduced pressure to give 28.5 g of the reaction product (a brown oily product). The reaction product was treated with a column chromatography using silica gel as a packing material and toluene as a developing solvent to give 20.9 g of 2-fluoro-4-propyl-benzaldehyde as a colorless oily product. In a three-necked flask equipped with a condenser, a dropping funnel and a thermometer, 12.6 g (0.126 mol) of chromic acid were dissolved in a solution of 200 ml of acetic acid and 20 ml of water and a solution of 20.9 g of the benzaldehyde derivative obtained as described above in 20 ml of acetic acid was added dropwise over 15 minutes while stirring at room temperature. After the dropwise addition, the mixture was heated to 50° C. and stirred at the same temperature for 5 hours. After completion of the reaction, the reaction solution was poured into 200 ml of ice-water and extracted with diethyl ether (150 ml×2). The extract was washed with water (150 ml×3) and dried over anhydrous magnesium sulfate to give 24.5 g of a brown crystalline product which was 2-fluoro-4-propylbenzoic acid.

2) Preparation of 3,4,5-Trifluorophenyl-(2-fluoro-4-propyl) benzoate

Esterification was carried out according to a known method. In a 300 ml three-necked flask equipped with a thermometer, a nitrogen gas inlet tube and an alkali trap, 22.0 g of 2-fluoro-4-propylbenzoic acid obtained in the above procedure 1) and 0.1 ml of pyridine were dissolved and 17.1 g of thionyl chloride was added dropwise at room temperature over 10 minutes while stirring. After the dropwise addition, the mixture was heated to 50° C. on a water bath and stirred for 2 hours. After the reaction solution was cooled to room temperature, unreacted thionyl chloride and toluene were distilled off and concentrated under reduced pressure by a tap aspirator, and subjected to vacuum distillation to give 22.0 g of a colorless oily product which was 2-fluoro-4-propylbenzoyl chloride. Next, into a 200 ml three-necked flask equipped with a thermometer, a nitrogen gas inlet tube, a dropping funnel and a condenser were charged 23.1 g (0.156 mol) of 3,4,5-trifluorophenol, 50 ml of toluene and 9.5 g (0.12 mol) of pyridine, and a solution of 22.0 g of 2-fluoro-4-propylbenzoyl chloride in 20 ml of toluene was added dropwise over 15 minutes while stirring at room temperature. After the dropwise addition, the solution was stirred for 3 hours while heating at 50° C. on a water bath and aged. After cooling to room temperature, 50 ml of water was added, the solution was transferred into a separating funnel, an organic layer was separated and a lower layer was further extracted with toluene (100 ml). The combined extract was washed in turn with 40 ml of 1 N aqueous hydrochloric acid, water (100 ml×2), a saturated aqueous solution of sodium hydrogencarbonate (50 ml) and water (100 ml×2), dried over anhydrous magnesium sulfate and concentrated under reduced pressure to give 29.1 g of a pale yellow crystalline product. The reaction product was column chromatographed using silica gel as a packing material and toluene as a developing solvent and then recrystallized from a toluene-ether mixed solvent to give 18.6 g of a colorless crystalline product, which was 3,4,5-trifluoro-phenyl-(2-fluoro-4-propyl)benzoate.

Following the above procedures and using 3-fluoroalkylbenzenes having different alkyl groups instead of 3-fluoropropylbenzene, the following 3,4,5-trifluorophenyl-(2-fluoro-4-alkyl)benzoates can be prepared.

3,4,5-trifluorophenyl-(2-fluoro-4-methyl)benzoate,
3,4,5-trifluorophenyl-(2-fluoro-4-ethyl)benzoate,
3,4,5-trifluorophenyl-(2-fluoro-4-butyl)benzoate,
3,4,5-trifluorophenyl-(2-fluoro-4-pentyl)benzoate,
3,4,5-trifluorophenyl-(2-fluoro-4-hexyl)benzoate,
3,4,5-trifluorophenyl-(2-fluoro-4-heptyl)benzoate,
3,4,5-trifluorophenyl-(2-fluoro-4-octyl)benzoate,
3,4,5-trifluorophenyl-(2-fluoro-4-nonyl)benzoate, and
3,4,5-trifluorophenyl-(2-fluoro-4-decyl)benzoate.

Further, following the above procedure and using 3,5-difluoroalkylbenzenes instead of 3-fluoropropylbenzene, the following 3,4,5-trifluorophenyl-(2,6-difluoro-4-alkyl) benzoates can be prepared.

3,4,5-trifluorophenyl-(2,6-difluoro-4-methyl)benzoate,
3,4,5-trifluorophenyl-(2,6-difluoro-4-ethyl)benzoate,
3,4,5-trifluorophenyl-(2,6-difluoro-4-propyl )benzoate,
3,4,5-trifluorophenyl-(2,6-difluoro-4-butyl)benzoate,
3,4,5-trifluorophenyl-(2,6-difluoro-4pentyl)benzoate,
3,4,5-trifluorophenyl-(2,6-difluoro-4-hexyl)benzoate,
3,4,5-trifluorophenyl-(2,6-difluoro-4-heptyl )benzoate,
3,4,5-trifluorophenyl-(2,6-difluoro-4-octyl )benzoate,
3,4,5-trifluorophenyl-(2,6-difluoro-4-nonyl)benzoate, and
3,4,5-trifluorophenyl-(2,6-difluoro-4-decyl)benzoate.

Example 2

Preparation of 3,4,5-Trifluorophenyl-(2-fluoro-4-(trans-4-propyl-cyclohexyl))benzoate (the Compound of Formula (1) wherein $R_1$=n—$C_3H_7$, m=1, A is a Cyclohexylene Group, n=0, $Z_1$ and $Z_2$ are a Covalent Bond and X=H)

The reaction steps are separated into two steps of 1) the preparation of 2-fluoro-4-(trans-4-propylcyclohexyl) benzoic acid and 2) the esterification. Each step will be explained below in detail.

1) Preparation of 2-Fluoro-4-(trans-4-propylcyclohexyl) benzoic Acid

Into a 1 L three-necked flask equipped with a thermometer, a condenser and a stirrer were charged 400 ml of ethylene glycol, 40.0 g (163.0 mmol) of 2-fluoro-4-(trans-4-propylcyclohexyl)benzonitrile and an aqueous solution of sodium hydroxide (19.6 g, 489.1 mmol) dissolved in an equal amount of water, and the mixture was heated to 150°

C. and stirred for 10 hours. After the reaction solution was cooled down to room temperature while stirring, the reaction system was made acidic by the addition of 200 ml of water and 200 ml of a 6N aqueous hydrochloric acid solution and then the precipitated insolubles were recovered by filtration. The filtered product was thoroughly washed with water, dried under reduced pressure and recrystallized from toluene to give 30.5 g of a colorless crystalline product which was 2-fluoro-4-(trans-4-propylcyclohexyl)benzoic acid.

2) Preparation of 3,4,5-Trifluorophenyl-(2-fluoro-4-(trans-4-propylcyclohexyl))benzoate In a three-necked flask equipped with a thermometer, a condenser, a dropping funnel and an alkali trap, 20 g (75.7 mmol) of 2-fluoro-4-(trans-4-propyl-cyclohexyl)benzoic acid obtained in the above procedure 1) and 0.3 ml of pyridine were dissolved in 100 ml of toluene and 13.5 g (113.5 mmol) of thionyl chloride was added dropwise at room temperature over 10 minutes while stirring. After the dropwise addition, the mixture was heated to 60° C. on a water bath and stirred for 2 hours. After the reaction solution was cooled down to room temperature, unreacted thionyl chloride and toluene were distilled off and concentrated under reduced pressure by a tap aspirator and then the residue was subjected to vacuum distillation to recover the fractions at bp 158–160° C./1.0 mmHg, thereby yielding 19.2 g of a colorless oily product which was 2-fluoro-4-(trans-4-propylcyclohexyl)benzoyl chloride. Next, into a 200 ml three-necked flask equipped with a thermometer, a condenser, a dropping funnel and a stirrer were charged 5.2 g (35 mmol) of 3,4,5-trifluoro-phenol, 20 ml of toluene and 3.0 g (38.0 mmol) of pyridine and then 2-fluoro-4-(trans-4-propylcyclohexyl)benzoyl chloride was added dropwise over 15 minutes while stirring at room temperature. After the dropwise addition, the mixture was heated to 60° C. on a water bath and stirred for 2 hours.

After cooling down to room temperature, 100 ml of water were added to terminate the reaction. After a toluene layer was separated from the reaction solution, the water layer was extracted with toluene (50 ml×2). The combined organic layer was washed in turn with 50 ml of a 1N aqueous hydrochloric acid solution and water (50 ml×2), dried over anhydrous magnesium sulfate and concentrated under reduced pressure to give 23.1 g of a brown crystalline reaction product. The reaction product was column chromatographed using silica gel as a packing material and toluene as a developing solvent and then recrystallized from heptane to give 14.8 g of a colorless crystalline product which was 3,4,5-trifluoro-phenyl-(2-fluoro-4-(trans-4-propylcyclohexyl))benzoate.

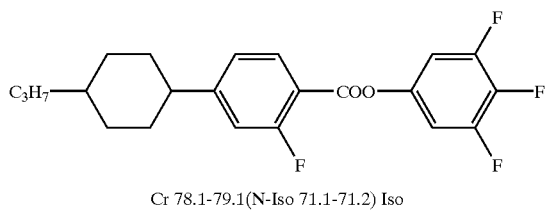

Cr 78.1–79.1(N-Iso 71.1-71.2) Iso

Following the above procedure and using 2-fluoro-4-(trans-4-alkylcyclohexyl)benzonitriles having different alkyl groups instead of 2-fluoro-4-(trans-4-propylcyclohexyl)benzonitrile, the following 3,4,5-trifluorophenyl-(2-fluoro-4-(trans-4-alkylcyclohexyl))benzoates can be prepared.

3,4,5-trifluorophenyl-(2-fluoro-4-(trans-4-methylcyclohexyl))benzoate, 3,4,5-trifluorophenyl-(2-fluoro-4-(trans-4-ethylcyclohexyl))benzoate, Cr 79.3–79.6 Iso, 3,4,5-trifluorophenyl-(2-fluoro-4-(trans-4-butylcyclohexyl))benzoate, 3,4,5-trifluorophenyl-(2-fluoro-4-(trans-4-pentylcyclohexyl))benzoate, Cr 73.8–74.7 N 85.0–85.1 Iso, 3,4,5-trifluorophenyl-(2-fluoro-4-(trans-4-hexylcyclohexyl))benzoate, 3,4,5-trifluorophenyl-(2-fluoro-4-(trans-4-heptylcyclohexyl))benzoate, 3,4,5-trifluorophenyl-(2-fluoro-4-(trans-4-octylcyclohexyl))benzoate, 3,4,5-trifluorophenyl-(2-fluoro-4-(trans-4-nonylcyclohexyl))benzoate, and 3,4,5-trifluorophenyl-(2-fluoro-4-(trans-4-decylcyclohexyl))benzoate.

Following the above procedure and using 2,6-difluoro-4-(trans-4-alkylcyclohexyl)benzonitriles instead of 2-fluoro-4-(trans-4-propylcyclohexyl)benzonitrile, the following 3,4,5-trifluorophenyl-(2,6-difluoro-4-(trans-4-alkylcyclohexyl))benzoates can be prepared.

3,4,5-trifluorophenyl-(2,6-difluoro-4-(trans-4-methylcyclohexyl))benzoate, 3,4,5-trifluorophenyl-(2,6-difluoro-4-(trans-4-ethylcyclohexyl))benzoate, 3,4,5-trifluorophenyl-(2,6-difluoro-4-(trans-4-propylcyclohexyl))benzoate, 3,4,5-trifluorophenyl-(2,6-difluoro-4-(trans-4-butylcyclohexyl))benzoate, 3,4,5-trifluorophenyl-(2,6-difluoro-4-(trans-4-pentylcyclohexyl))benzoate, Cr 76.8–77.1 (N 63.1–63.8) Iso, 3,4,5-trifluorophenyl-(2,6-difluoro-4-(trans-4-hexylcyclohexyl))benzoate, 3,4,5-trifluorophenyl-(2,6-difluoro-4-(trans-4-heptylcyclohexyl))benzoate, 3,4,5-trifluorophenyl-(2,6-difluoro-4-(trans-4-octylcyclohexyl))benzoate, 3,4,5-trifluorophenyl-(2,6-difluoro-4-(trans-4-nonylcyclohexyl))benzoate, and 3,4,5-trifluorophenyl-(2,6-difluoro-4-(trans-4-decylcyclohexyl))benzoate.

Example 3

Preparation of 3,4,5-Trifluorophenyl-(2-fluoro-4-(trans-4-(3-butenyl)cyclohexyl))benzoate (the Compound of Formula (1) wherein $R_1=C_4H_7$, m=1, n=0, A is a Cyclohexylene Group, $Z_1$ and $Z_2$ are a Covalent Bond and X=H)

In a 300 ml three-necked flask equipped with a thermometer, a condenser and a stirrer, 10 g (38.9 mmol) of 2-fluoro-4-(trans-4-(3-butenyl)benzonitrile and 5 ml of a solution of 3.9 g (97.1 mmol) of sodium hydroxide dissolved in an equal amount of water were dissolved under heat in 100 ml of ethylene glycol and the mixture was stirred for 5 hours while maintaining at 180° C. After the mixture was cooled down to room temperature, 50 ml of water and 20 ml of a 6N aqueous hydrochloric acid solution were added and the precipitated crystalline product was separated by filtration. The filtered product was repeatedly washed with water, dried and recrystallized from toluene to give 9.8 g of a colorless crystalline product which was 2-fluoro-4-(trans-4-(3-butenyl)cyclohexyl)benzoic acid.

In a 500 ml three-necked flask equipped with a stirrer, a thermometer, a dropping funnel and a nitrogen gas inlet tube, 9.8 g (35.4 mmol) of 2-fluoro-4-(trans-4-(3-butenyl) cyclohexyl)benzoic acid obtained in the above procedure, 8.0 g (38.9 mmol) of dicyclohexylcarbodiimide and 0.13 g (1.1 mmol) of 4-dimethylaminopyridine were suspended in 200 ml of dichloromethane and 6.8 g (46.0 mmol) of 3,4,5-trifluorophenol were added dropwise over 5 minutes. After the dropwise addition, the mixture was stirred at room temperature for 10 hours. After 100 ml of water were added to the reaction solution to terminate the reaction, the insolubles in dichloromethane were separated by filtration and then the dichloromethane layer was separated from the reaction solution. The aqueous layer was extracted with 100 ml of dichloromethane. The combined organic layer was washed with water (100 ml×3), dried over anhydrous magnesium sulfate and concentrated under reduced pressure to give 9.4 g of a pale yellow crystalline reaction product. The reaction product was purified by a silica gel column chromatography using toluene as a developing solvent and recrystallized from a toluene-heptane mixed solvent to give 4.9 g of a colorless crystalline product which was 3,4,5-trifluorophenyl-(2-fluoro-4-(trans-4-(3-butenyl) cyclohexyl))benzoate.

Following the above procedure and using 2-fluoro-4-(trans-4-((E)-alkenyl)cyclohexyl)benzonitriles having different alkyl groups or different positions of the olefin on the alkyl chain instead of 2-fluoro-4-(trans-4-(3-butenyl) cyclohexyl)benzonitrile, the following 3,4,5-trifluorophenyl-(2-fluoro-4-(trans-4-((E)-alkenyl) cyclohexyl))benzoates can be prepared.

3,4,5-trifluorophenyl-(2-fluoro-4-(trans-4-((E)-1-butenyl)cyclohexyl))benzoate, 3,4,5-trifluorophenyl-(2-fluoro-4-(trans-4-((E)-2-butenyl)cyclohexyl))benzoate, 3,4,5-trifluorophenyl-(2-fluoro-4-(trans-4-((E)-1-pentenyl)cyclohexyl))benzoate, 3,4,5-trifluorophenyl-(2-fluoro-4-(trans-4-((E)-2-pentenyl)cyclohexyl))benzoate, 3,4,5-trifluorophenyl-(2-fluoro-4-(trans-4-((E)-3-pentenyl)cyclohexyl))benzoate, 3,4,5-trifluorophenyl-(2-fluoro-4-(trans-4-(4-pentenyl) cyclohexyl))benzoate, 3,4,5-trifluorophenyl-(2-fluoro-4-(trans-4-((E)-1-hexenyl)cyclohexyl))benzoate, 3,4,5-trifluorophenyl-(2-fluoro-4-(trans-4-((E)-2-hexenyl)cyclohexyl))benzoate, 3,4,5-trifluorophenyl-(2-fluoro-4-(trans-4-((E)-3-hexenyl)cyclohexyl))benzoate, 3,4,5-trifluorophenyl-(2-fluoro-4-(trans-4-((E)-4-hexenyl)cyclohexyl))benzoate, and 3,4,5-trifluorophenyl-(2-fluoro-4-(trans-4-(5-hexenyl) cyclohexyl))benzoate.

Following the above procedure and using 2,6-difluoro-4-(trans-4-((E)-alkenyl)cyclohexyl)benzonitriles having different alkyl groups or different positions of the olefin on the alkyl chain instead of 2-fluoro-4-(trans-4-(3-butenyl) cyclohexyl)benzonitrile, the following 3,4,5-trifluorophenyl-(2,6-difluoro-4-(trans-4-((E)-alkenyl) cyclohexyl))benzoates can be prepared.

3,4,5-trifluorophenyl-(2,6-difluoro-4-(trans-4-((E)-1-butenyl)cyclohexyl))benzoate, 3,4,5-trifluorophenyl-(2,6-difluoro-4-(trans-4-((E)-2-butenyl)cyclohexyl))benzoate, 3,4,5-trifluorophenyl-(2,6-difluoro-4-(trans-4-((E)-1-pentenyl)cyclohexyl))benzoate, 3,4,5-trifluorophenyl-(2,6-difluoro-4-(trans-4-((E)-2-pentenyl)cyclohexyl))benzoate, 3,4,5-trifluorophenyl-(2,6-difluoro-4-(trans-4-((E)-3-pentenyl)cyclohexyl))benzoate, 3,4,5-trifluorophenyl-(2,6-difluoro-4-(trans-4-(4-pentenyl)cyclohexyl))benzoate, 3,4,5-trifluorophenyl-(2,6-difluoro-4-(trans-4-((E)-1-hexenyl)cyclohexyl))benzoate, 3,4,5-trifluorophenyl-(2,6-difluoro-4-(trans-4-((E)-2-hexenyl)cyclohexyl))benzoate, 3,4,5-trifluorophenyl-(2,6-difluoro-4-(trans-4-((E)-3-hexenyl)cyclohexyl))benzoate, 3,4,5-trifluorophenyl-(2,6-difluoro-4-(trans-4-((E)-4-hexenyl)cyclohexyl))benzoate, and 3,4,5-trifluorophenyl-(2,6-difluoro-4-(trans-4-(5-hexenyl)cyclohexyl))benzoate.

Example 4

Preparation of 3,4,5-Trifluorophenyl-(2-fluoro-(2-(trans-4-propylcyclohexyl)ethyl))benzoate (the Compound of Formula (1) wherein $R_1$=n—$C_3H_7$, m=1, A is a Cyclohexylene Group, n=0, $Z_1$=—$CH_2CH_2$—, $Z_2$ is a Covalent Bond and X=H)

The preparation steps are divided into two steps of 1) the preparation of 2-fluoro-(2-(trans-4-propylcyclo-hexyl)ethyl) benzoyl chloride and 2) the preparation of 3,4,5-trifluoro-(2-fluoro-(2-(trans-4-propylcyclohexyl)ethyl)benzoate by esterification. Each step will be explained below in detail.

1) Preparation of 2-Fluoro-(2-(trans-4-propylcyclohexyl) ethyl)benzoyl Chloride

In a 300 ml three-necked flask equipped with a thermometer, a condenser and a stirrer, 19.5 g (71.0 mmol) of 2-fluoro-(2-(trans-4-propylcyclohexyl)ethyl)benzonitrile (see, Example 4 of Japanese Patent Kokai 1-168659) and a solution of 7.1 g (177.0 mmol) of sodium hydroxide dissolved in an equal amount of water were dissolved in 100 ml of ethylene glycol and the mixture was stirred for 8 hours while heating to 150° C. After the reaction solution was cooled down to room temperature, 100 ml of water and 40 ml of a 6N aqueous hydrochloric acid solution were added and the precipitated insolubles were separated by filtration. The filtered product was washed with 300 ml of water, dried under reduced pressure and recrystallized from toluene to give 16.6 g of a colorless crystalline product which was 2-fluoro-(2-(trans-4-propyl-cyclohexyl)ethyl)benzoic acid. In a 300 ml Kjeldahl flask equipped with a thermometer and a dropping funnel, 16.6 g(57.0 mmol) of 2-fluoro-(2-(trans-4-propylcyclohexyl)ethyl)benzoic acid obtained in the above procedure and 0.5 g of pyridine were dissolved in 100 ml of toluene, the mixture was heated to 40° C. while stirring with a magnetic stirrer and 10.2 g (86.0 mmol) of thionyl chloride were added dropwise over 10 minutes while maintaining at 40° C. After the dropwise addition, the mixture was stirred at the same temperature for 1.5 hours. Unreacted thionyl chloride and toluene were distilled off from the reaction solution and concentrated under reduced pressure by a tap aspirator. Then, the concentrated residue was purified by vacuum distillation to give 15.7 g of a colorless oily productwhich was 2-fluoro-(2-(trans-4-propylcyclohexyl)ethyl)benzoyl chloride.

2) Preparation of 3,4,5-Trifluorophenyl-(2-fluoro-(2-(trans-4-propylcyclohexyl)ethyl))benzoate In a 200 ml three-necked flask equipped with a thermometer, a nitrogen gas inlet tube, a stirrer and a dropping funnel, 9.8 g (66.3 mmol) of 3,4,5-trifluorophenol were dissolved in 50 ml of toluene and 5.8 g (72.9 mmol) of pyridine was added. 15.7 g (51.0 mmol) of 2-fluoro-(2-(trans-4-propylcyclohexyl)ethyl)benzoyl chloride obtained in the above procedure 1) were added dropwise over 20 minutes while stirring at room temperature. After the dropwise addition, the mixture was maintained at 60° C. on a hot bath and aged for 2 hours, and then 100 ml of water were added to the reaction solution to terminate the reaction. From the reaction mixture was separated a toluene layer, and then the aqueous layer was further extracted with 100 ml of toluene.

The combined organic layer was washed in turn with 100 ml of water, 50 ml of a saturated aqueous solution of sodium hydrogencarbonate and water (100 ml×2), dried over anhydrous magnesium sulfate and concentrated to give 19.9 g of the reaction product. The reaction product was purified by a silica gel column chromatography using toluene as a developing solvent and then recrystallized from a toluene-heptane mixed solvent to give 12.9 g of a colorless crystalline product which was 3,4,5-trifluorophenyl-(2-fluoro-(2-(trans-4-propylcyclohexyl)ethyl))benzoate.

Following the above procedure and using 2-fluoro-(2-(trans-4-alkylcyclohexyl)ethyl)benzonitriles having different alkyl groups instead of 2-fluoro-(2-(trans-4-propylcyclohexyl)ethylbenzonitrile, the following 3,4,5-trifluorophenyl-(2-fluoro-(2-(trans-4-alkylcyclo-hexyl)ethyl))benzoates can be prepared.

3,4,5-trifluorophenyl-(2-fluoro-(2-(trans-4-methylcyclohexyl)ethyl))benzoate, 3,4,5-trifluorophenyl-(2-fluoro-(2-(trans-4-ethylcyclohexyl)ethyl))benzoate, 3,4,5-trifluorophenyl-(2-fluoro-(2-(trans-4-butylcyclohexyl)ethyl))benzoate, 3,4,5-trifluorophenyl-(2-fluoro-(2-(trans-4-pentylcyclohexyl)ethyl))benzoate, 3,4,5-trifluorophenyl-(2-fluoro-(2-(trans-4-hexylcyclohexyl)ethyl))benzoate, 3,4,5-trifluorophenyl-(2-fluoro-(2-(trans-4-heptylcyclohexyl)ethyl))benzoate, 3,4,5-trifluorophenyl-(2-fluoro-(2-(trans-4-octylcyclohexyl)ethyl))benzoate, 3,4,5-trifluorophenyl-(2-fluoro-(2-(trans-4-nonylcyclohexyl)ethyl))benzoate, and 3,4,5-trifluorophenyl-(2-fluoro-(2-(trans-4-decylcyclohexyl)ethyl))benzoate.

Following the above procedure and using 2,6-difluoro-(2-(trans-4-alkylcyclohexyl)ethyl)benzonitriles having different alkyl groups instead of 2-fluoro-(2-(trans-4-propylcyclohexyl)ethyl)benzonitrile, the following 3,4,5-trifluorophenyl-(2,6-difluoro-(2-(trans-4-alkylcyclohexyl)ethyl))benzoates can be prepared.

3,4,5-trifluorophenyl-(2,6-difluoro-(2-(trans-4-methylcyclohexyl)ethyl))benzoate, 3,4,5-trifluorophenyl-(2,6-difluoro-(2-(trans-4-ethylcyclohexyl)ethyl))benzoate, 3,4,5-trifluorophenyl-(2,6-difluoro-(2-(trans-4-propylcyclohexyl)ethyl))benzoate, 3,4,5-trifluorophenyl-(2,6-difluoro-(2-(trans-4-butylcyclohexyl)ethyl))benzoate, 3,4,5-trifluorophenyl-(2,6-difluoro-(2-(trans-4-pentylcyclohexyl)ethyl))benzoate, 3,4,5-trifluorophenyl-(2,6-difluoro-(2-(trans-4-hexylcyclohexyl)ethyl))benzoate, 3,4,5-trifluorophenyl-(2,6-difluoro-(2-(trans-4-heptylcyclohexyl)ethyl))benzoate, 3,4,5-trifluorophenyl-(2,6-difluoro-(2-(trans-4-octylcyclohexyl)ethyl))benzoate, 3,4,5-trifluorophenyl-(2,6-difluoro-(2-(trans-4-nonylcyclohexyl)ethyl))benzoate, and 3,4,5-trifluorophenyl-(2,6-difluoro-(2-(trans-4-decylcyclohexyl)ethyl))benzoate.

Example 5

Preparation of 3,4,5-Trifluorophenyl-(3-fluoro-4'-propylbiphenyl)carboxylate (the Compound of Formula (1) wherein $R_1=C_3H_7$, m=1, n=0, A is a 1,4-Phenylene Group, $Z_1$ and $Z_2$ are a Covalent Bond and X=H)

In a 300 ml Kjeldahl flask, 15 g (58.1 mmol) of 2-fluoro-4-(4-propylphenyl)benzoic acid were dissolved in 60 ml of toluene and 0.2 g of pyridine was added. Then, 8.9 g (75.5 mmol) of thionyl chloride were added dropwise at room temperature over 10 minutes while stirring. After the dropwise addition, the reaction was carried out for 2 hours by heating the mixture to 60° C. on a hot bath and maintaining it at the same temperature. Unreacted thionyl chloride and toluene were distilled off from the reaction solution under reduced pressure by a tap aspirator, concentrated, and distilled under reduced pressure to give the corresponding acid chloride derivative (colorless oily product 14.6 g). Then, in a 200 ml three-necked flask equipped with a stirrer, a nitrogen gas inlet tube, a thermometer and a dropping funnel, 10.2 g (68.6 mmol) of 3,4,5-trifluorophenol and 4.4 g (55.4 mmol) of pyridine were dissolved in 50 ml of toluene under a nitrogen atmosphere and 14.6 g (52.8 mmol) of the acid chloride derivative was added dropwise over 20 minutes while stirring. After the dropwise addition, the mixture was maintained at 60° C. on a hot bath and aged for 2 hours. 100 ml of water were added to the reaction solution to terminate the reaction. After the toluene layer was separated from the reaction solution, the aqueous layer was further extracted with 100 ml of toluene. The combined organic layer was washed in turn with 100 ml of water, 50 ml of a saturated aqueous solution of sodium hydrogencarbonate and water (100 ml×2), dried over anhydrous magnesium sulfate and concentrated to give 18.2 g of the reaction product. The reaction product was purified by a silica gel column chromatography using toluene as a developing solvent and then recrystallized from a toluene-heptane mixed solvent to give 11.3 g of a colorless crystalline product which was 3,4,5-trifluorophenyl-(3-fluoro-4'-propylbiphenyl)carboxylate.

Following the above procedure and using 2-fluoro-4-(4-alkylphenyl)benzoic acids having different alkyl groups instead of 2-fluoro-4-(4-propylphenyl)benzoic acid, the following 3,4,5-trifluorophenyl-(3-fluoro-4'-alkylbiphenyl)carboxylates can be prepared.

3,4,5-trifluorophenyl-(3-fluoro-4'-methylbiphenyl)carboxylate, 3,4,5-trifluorophenyl-(3-fluoro-4'-ethylbiphenyl)carboxylate, 3,4,5-trifluorophenyl-(3-fluoro-4'-butylbiphenyl)carboxylate, 3,4,5-trifluorophenyl-(3-fluoro-4'-pentylbiphenyl)carboxylate, 3,4,5-trifluorophenyl-(3-fluoro-4'-hexylbiphenyl)carboxylate, 3,4,5-trifluorophenyl-(3-fluoro-4'-heptylbiphenyl) carboxylate, 3,4,5-trifluorophenyl-(3-fluoro-4'-octylbiphenyl) carboxylate, 3,4,5-trifluorophenyl-(3-fluoro-4'-nonylbiphenyl) carboxylate, and 3,4,5-trifluorophenyl-(3-fluoro-4'-decylbiphenyl) carboxylate.

Following the above procedure and using 2,6-difluoro-4-(4-alkylphenyl)benzoic acids instead of 2-fluoro-4-(4-propylphenyl)benzoic acid, the following 3,4,5-trifluorophenyl-(3,5-difluoro-(4'-alkylbiphenyl)carboxylates can be prepared.

3,4,5-trifluorophenyl-(3,5-difluoro-4'-methylbiphenyl) carboxylate, 3,4,5-trifluorophenyl-(3,5-difluoro-4'-ethylbiphenyl) carboxylate, 3,4,5-trifluorophenyl-(3,5-difluoro-4'-propylbiphenyl) carboxylate, 3,4,5-trifluorophenyl-(3,5-difluoro-4'-butylbiphenyl) carboxylate, 3,4,5-trifluorophenyl-(3,5-difluoro-4'-pentylbiphenyl) carboxylate, 3,4,5-trifluorophenyl-(3,5-difluoro-4'-hexylbiphenyl) carboxylate, 3,4,5-trifluorophenyl-(3,5-difluoro-4'-heptylbiphenyl) carboxylate, 3,4,5-trifluorophenyl-(3,5-difluoro-4'-octylbiphenyl) carboxylate, 3,4,5-trifluorophenyl-(3,5-difluoro-4'-nonylbiphenyl) carboxylate, and 3,4,5-trifluorophenyl-(3,5-difluoro-4'-decylbiphenyl) carboxylate.

Example 6

Preparation of 3,4,5-Trifluorophenyl-(2-fluoro-4-(2-(4-propylphenyl)ethyl))benzoate (the Compound of Formula (1) wherein $R_1$=n-$C_3H_7$, m=1, n=0, A is a 1,4-Phenylene Group, $Z_1$=—$CH_2CH_2$— and $Z_2$ is a Covalent Bond and X=H)

In a 300 ml Kjeldahl flask, 15 g (52.4 mmol) of 2-fluoro-4-(2-(4-propylphenyl)ethyl)benzoic acid were dissolved in 80 ml of toluene and 0.2 g of pyridine was added. Then, 8.1 g (68.1 mmol) of thionyl chloride were added dropwise at room temperature over 10 minutes while stirring. After the dropwise addition, the reaction was carried out for 2 hours by heating the mixture to 60° C. on a hot bath and maintaining it at the same temperature. Unreacted thionyl chloride and toluene were distilled off from the reaction solution under reduced pressure by a tap aspirator, concentrated, and distilled under reduced pressure to give the corresponding acid chloride derivative (colorless oily product 13.9 g). Then, in a 200 ml three-necked flask equipped with a stirrer, a nitrogen gas inlet tube, a thermometer and a dropping funnel, 8.8 g (59.3 mmol) of 3,4,5-trifluorophenol and 3.9 g (50.2 mmol) of pyridine were dissolved in 50 ml of toluene under a nitrogen atmosphere and 13.9 g (45.6 mmol) of the acid chloride derivative were added dropwise over 15 minutes while stirring. After the dropwise addition, the mixture was maintained at 60° C. on a hot bath and aged for 2 hours. 100 ml of water were added to the reaction solution to terminate the reaction. After the toluene layer was separated from the reaction solution, the aqueous layer was further extracted with 100 ml of toluene. The combined organic layer was washed in turn with 100 ml of water, 50 ml of a saturated aqueous solution of sodium hydrogencarbonate and water (100 ml×2), dried over anhydrous magnesium sulfate and concentrated to give 13.7 g of the reaction product.

The reaction product was purified by a silica gel column chromatography using toluene as a developing solvent and then recrystallized from a toluene-heptane mixed solvent to give 8.6 g of a colorless crystalline product which was 3,4,5-trifluorophenyl-(2-fluoro-4-(2-(4-propylphenyl)ethyl))benzoate.

Following the above procedure and using 2-fluoro-4-(2-(4-alkylphenyl)ethyl)benzoic acids having different alkyl groups instead of 2-fluoro-4-(2-(4-propyl-phenyl)ethyl) benzoic acid, the following 3,4,5-trifluoro-phenyl-(2-fluoro-4-(2-(4-alkylphenyl)ethyl))benzoates can be prepared.

3,4,5-trifluorophenyl-(2-fluoro-4-(2-(4-methylphenyl) ethyl))benzoate, 3,4,5-trifluorophenyl-(2-fluoro-4-(2-(4-ethylphenyl) ethyl))benzoate, 3,4,5-trifluorophenyl-(2-fluoro-4-(2-(4-butylphenyl) ethyl))benzoate, 3,4,5-trifluorophenyl-(2-fluoro-4-(2-(4-pentylphenyl) ethyl))benzoate, 3,4,5-trifluorophenyl-(2-fluoro-4-(2-(4-hexylphenyl) ethyl))benzoate, 3,4,5-trifluorophenyl-(2-fluoro-4-(2-(4-heptylphenyl) ethyl))benzoate, 3,4,5-trifluorophenyl-(2-fluoro-4-(2-(4-octylphenyl) ethyl))benzoate, 3,4,5-trifluorophenyl-(2-fluoro-4-(2-(4-nonylphenyl) ethyl))benzoate, and 3,4,5-trifluorophenyl-(2-fluoro-4-(2-(4-decylphenyl) ethyl))benzoate.

Following the above procedure and using 2,6-difluoro-4-(2-(4-alkylphenyl)ethyl)benzoic acids having different alkyl groups instead of 2-fluoro-4-(2-(4-propylphenyl)ethyl) benzoic acid, the following 3,4,5-trifluorophenyl-(2,6-difluoro-4-(2-(4-alkylphenyl)ethyl))benzoates can be prepared.

3,4,5-trifluorophenyl-(2,6-difluoro-4-(2-(4-methylphenyl)ethyl))benzoate, 3,4,5-trifluorophenyl-(2,6-difluoro-4-(2-(4-ethylphenyl) ethyl))benzoate, 3,4,5-trifluorophenyl-(2,6-difluoro-4-(2-(4-propylphenyl)ethyl))benzoate, 3,4,5-trifluorophenyl-(2,6-difluoro-4-(2-(4-butylphenyl) ethyl))benzoate, 3,4,5-trifluorophenyl-(2,6-difluoro-4-(2-(4-pentylphenyl) ethyl))benzoate, 3,4,5-trifluorophenyl-(2,6-difluoro-4-(2-(4-hexylphenyl) ethyl))benzoate, 3,4,5-trifluorophenyl-(2,6-difluoro-4-(2-(4-heptylphenyl) ethyl))benzoate, 3,4,5-trifluorophenyl-(2,6-difluoro-4-(2-(4-octylphenyl) ethyl))benzoate, 3,4,5-trifluorophenyl-(2,6-difluoro-4-(2-(4-nonylphenyl) ethyl))benzoate, and 3,4,5-trifluorophenyl-(2,6-difluoro-4-(2-(4-decylphenyl) ethyl))benzoate.

Example 7

Preparation of 3,4,5-Trifluorophenyl-(2-fluoro-4-(trans-4-(trans-4-ethylcyclohexyl)cyclohexyl)) benzoate (the Compound of Formula (1) wherein $R_1$=$C_2H$, m=n=1, both A and B are a 1,4-Cyclohexylene Group, $Z_1$ and $Z_2$ are a Covalent Bond and X=H)

In a 300 ml three-necked flask equipped with a stirrer, a thermometer and a condenser, 10 g (31.9 mmol) of 2-fluoro- 4-(trans-4-(trans-4-ethylcyclohexyl)cyclohexyl)benzonitrile and 5 ml of an aqueous solution of 3.2 g (79.8 mmol) of sodium hydroxide dissolved in an equal amount of water were dissolved under heat in 100 ml of ethylene glycol and the mixture was stirred for 5 hours while maintaining at 180° C. After the mixture was cooled down to room temperature, 50 ml of water and 20 ml of a 6N aqueous hydrochloric acid solution were added and the precipitated crystalline product was separated by filtration. The filtered product was repeatedly washed with water, dried under reduced pressure and recrystallized from toluene to give 9.8 g of a colorless crystalline product which was 2-fluoro-4-(trans-4-(trans-4-ethylcyclohexyl)cyclohexyl)benzoic acid.

In a 300 ml Kjeldahl flask, 9.8 g (29.3 mmol) of 2-fluoro-4-(trans-4-(trans-4-ethylcyclohexyl)cyclohexyl)benzoic acid were dissolved in 100 ml of toluene and 0.2 g of pyridine was added. Then, 4.5 g (38.1 mmol) of thionyl chloride were added dropwise at room temperature over 3 minutes while stirring. After the dropwise addition, the reaction was carried out for 2 hours by heating the mixture to 60° C. on a hot bath and maintaining it at the same temperature. Unreacted thionyl chloride and toluene were distilled off from the reaction solution under reduced pressure by a tap aspirator, concentrated, and distilled under reduced pressure to give the corresponding acid it chloride derivative (colorless oily product 8.5 g). Then, in a 200 ml three-necked flask equipped with a stirrer, a nitrogen gas inlet tube, a thermometer and a dropping funnel, 4.3 g (29.2 mmol) of 3,4,5-trifluorophenol and 2.1 g (26.7 mmol) of pyridine were dissolved in 50 ml of toluene under a nitrogen atmosphere and 8.5 g (24.3 mmol) of the acid chloride derivative were added dropwise over 10 minutes while stirring. After the dropwise addition, the mixture was maintained at 60° C. on a hot bath and aged for 2 hours. 100 ml of water were added to the reaction solution to terminate the reaction. After the toluene layer was separated from the reaction solution, the aqueous layer was further extracted with 100 ml of diethyl ether. The combined organic layer was washed in turn with 100 ml of water, 50 ml of a 2N aqueous sodium hydroxide solution and water (100 ml×2), dried over anhydrous magnesium sulfate and concentrated to give 9.7 g of the reaction product. The reaction product was purified by a silica gel column chromatography using toluene as a developing solvent and recrystallized from a toluene-heptane mixed solvent to give 5.7 g of a colorless crystalline product which was 3,4,5-trifluorophenyl-(2-fluoro-4-5 (trans-4-(trans-4-ethylcyclohexyl)cyclohexyl)) benzoate.

Following the above procedure and using 2-fluoro-4-(trans-4-(trans-4-alkylcyclohexyl)cyclohexyl)benzonitriles having different alkyl groups instead of 2-fluoro-4-(trans-4-(trans-4-ethylcyclohexyl)cyclohexyl)benzonitrile, the following 3,4,5-trifluorophenyl-(2-fluoro-4-(trans-4-(trans-4-alkylcyclohexyl)cyclohexyl))benzoates can be prepared.

3,4,5-trifluorophenyl-(2-fluoro-4-(trans-4-(trans-4-methylcyclohexyl)cyclohexyl))benzoate, 3,4,5-trifluorophenyl-(2-fluoro-4-(trans-4-(trans-4-propylcyclohexyl)cyclohexyl))benzoate, Cr 110.1–110.9 N 248.9–249.7 Iso, 3,4,5-trifluorophenyl-(2-fluoro-4-(trans-4-(trans-4-butylcyclohexyl)cyclohexyl))benzoate, 3,4,5-trifluorophenyl-(2-fluoro-4-(trans-4-(trans-4-pentylcyclohexyl)cyclohexyl))benzoate, 3,4,5-trifluorophenyl-(2-fluoro-4-(trans-4-(trans-4-hexylcyclohexyl)cyclohexyl))benzoate, 3,4,5-trifluorophenyl-(2-fluoro-4-(trans-4-(trans-4-heptylcyclohexyl)cyclohexyl))benzoate, 3,4,5-trifluorophenyl-(2-fluoro-4-(trans-4-(trans-4-octylcyclohexyl)cyclohexyl))benzoate, 3,4,5-trifluorophenyl-(2-fluoro-4-(trans-4-(trans-4-nonylcyclohexyl)cyclohexyl))benzoate, and 3,4,5-trifluorophenyl-(2-fluoro-4-(trans-4-(trans-4-decylcyclohexyl)cyclohexyl))benzoate.

Following the above procedure and using 2,6-difluoro-4-(trans-4-(trans-4-alkylcyclohexyl)cyclohexyl)benzonitriles having different alkyl groups instead of 2-fluoro-4-(trans-4-(trans-4-ethylcyclohexyl)cyclohexyl)benzonitrile, the following 3,4,5-trifluorophenyl-(2,6-difluoro-4-(trans-4-(trans-4-alkylcyclohexyl)cyclohexyl))benzoates can be prepared.

3,4,5-trifluorophenyl-(2,6-difluoro-4-(trans-4-(trans-4-methylcyclohexyl)cyclohexyl))benzoate, 3,4,5-trifluorophenyl-(2,6-difluoro-4-(trans-4-(trans-4-ethylcyclohexyl)cyclohexyl))benzoate, 3,4,5-trifluorophenyl-(2,6-difluoro-4-(trans-4-(trans-4-propylcyclohexyl)cyclohexyl))benzoate, 3,4,5-trifluorophenyl-(2,6-difluoro-4-(trans-4-(trans-4-butylcyclohexyl)cyclohexyl))benzoate, 3,4,5-trifluorophenyl-(2,6-difluoro-4-(trans-4-(trans-4-pentylcyclohexyl)cyclohexyl))benzoate, 3,4,5-trifluorophenyl-(2,6-difluoro-4-(trans-4-(trans-4-hexylcyclohexyl)cyclohexyl))benzoate, 3,4,5-trifluorophenyl-(2,6-difluoro-4-(trans-4-(trans-4-heptylcyclohexyl)cyclohexyl))benzoate, 3,4,5-trifluorophenyl-(2,6-difluoro-4-(trans-4-(trans-4-octylcyclohexyl)cyclohexyl))benzoate, 3,4,5-trifluorophenyl-(2,6-difluoro-4-(trans-4-(trans-4-nonylcyclohexyl)cyclohexyl))benzoate, and 3,4,5-trifluorophenyl-(2,6-difluoro-4-(trans-4-(trans-4-decylcyclohexyl)cyclohexyl))benzoate.

Example 8

Preparation of 3,4,5-Trifluorophenyl-(2-fluoro-4-(4-(trans-4-propylcyclohexyl)phenyl))benzoate (the Compound of Formula (1) wherein $R_1=C_3H_7$, m=n=1, A is a 1,4-Cyclohexylene Group, B is a 1,4-Phenylene Group, $Z_1$ and $Z_2$ are a Covalent Bond and X=H)

In a 300 ml three-necked flask equipped with a stirrer, a thermometer and a condenser, 5 g (15.6 mmol) of 2-fluoro-4-(4-(trans-4-propylcyclohexyl)phenyl)benzonitrile and 1.6 g (38.9 mmol) of sodium hydroxide were dissolved under heat in 50 ml of ethylene glycol and the mixture was stirred for 5 hours while maintaining at 180° C. After the mixture was cooled down to room temperature while stirring, 30 ml of water and 15 ml of a 6N aqueous hydrochloric acid solution were added and the precipitated crystalline product was separated by filtration. The filtered product was repeatedly washed with water, dried and recrystallized from toluene to give 4.1 g of a colorless crystalline product which was 2-fluoro-4-(4-(trans-4-propylcyclohexyl)phenyl)benzoic acid.

In a 200 ml Kjeldahl flask, 4.1 g (11.9 mmol) of 2-fluoro-4-(4-(trans-4-propylcyclohexyl)phenyl)benzoic acid were dissolved in 50 ml of toluene and 0.1 g of pyridine was added. 1.8 g (15.5 mmol) of thionyl chloride were added dropwise at room temperature while stirring. After the dropwise addition, the reaction was carried out for 2 hours by heating the mixture to 60° C. on a hot bath and maintaining it at the same temperature. Unreacted thionyl chloride and toluene were distilled off from the reaction solution under reduced pressure by a tap aspirator and concentrated. Then, in a 100 ml three-necked flask equipped with a stirrer, a nitrogen gas inlet tube, a thermometer and a dropping funnel, 2.5 g (16.7 mmol) of 3,4,5-trifluorophenol and 1.1 g (13.1 mmol) of pyridine were dissolved in 30 ml of toluene under a nitrogen atmosphere and the concentrate obtained in the above procedure was added dropwise over 5 minutes while stirring. After the dropwise addition, the mixture was maintained at 60° C. on a hot bath and aged for 2 hours. 50 ml of water were added to the reaction solution to terminate the reaction. After the toluene layer was separated from the reaction solution, the aqueous layer was further extracted with 100 ml of diethyl ether. The combined organic layer was washed in turn with 100 ml of water, 50 ml of a 2N aqueous sodium hydroxide solution and water (100 ml×2), dried over anhydrous magnesium sulfate and concentrated to give 4.1 g of the reaction product. The reaction product was purified by a silica gel column chromatography using toluene as a developing solvent and recrystallized from toluene to give 3.0 g of a colorless crystalline product which was 3,4,5-trifluorophenyl-(2-fluoro-4-(4-(trans-4-propylcyclohexyl)phenyl))benzoate.

Following the above procedure and using 2-fluoro-4-(4-(trans-4-alkylcyclohexyl)phenyl)benzonitriles having different alkyl groups instead of 2-fluoro-4-(4-(trans-4-propylcyclohexyl)phenyl)benzonitrile, the following 3,4,5-trifluorophenyl-(2-fluoro-4-(4-(trans-4-alkylcyclohexyl)phenyl))benzoates can be prepared.

3,4,5-trifluorophenyl-(2-fluoro-4-(4-(trans-4-methylcyclohexyl)phenyl))benzoate, 3,4,5-trifluorophenyl-(2-fluoro-4-(4-(trans-4-ethylcyclohexyl)phenyl))benzoate, 3,4,5-trifluorophenyl-(2-fluoro-4-(4-(trans-4-butylcyclohexyl )phenyl))benzoate, 3,4,5-trifluorophenyl-(2-fluoro-4-(4-(trans-4-pentylcyclohexyl )phenyl))benzoate, 3,4,5-trifluorophenyl-(2-fluoro-4-(4-(trans-4-hexylcyclohexyl)phenyl))benzoate, 3,4,5-trifluorophenyl-(2-fluoro-4-(4-(trans-4-heptylcyclohexyl )phenyl))benzoate, 3,4,5-trifluorophenyl-(2-fluoro-4-(4-(trans-4-octylcyclohexyl)phenyl))benzoate, 3,4,5-trifluorophenyl-(2-fluoro-4-(4-(trans-4-nonylcyclohexyl)phenyl))benzoate, and 3,4,5-trifluorophenyl-(2-fluoro-4-(4-(trans-4-decylcyclohexyl)phenyl))benzoate.

Further, following the above procedure and using 2,6-difluoro-4-(4-(trans-4-alkylcyclohexyl)phenyl)benzonitriles having different alkyl groups instead of 2-fluoro-4-(4-(trans-4-propylcyclohexyl)phenyl)benzonitrile, the following 3,4,5-trifluorophenyl-(2,6-difluoro-4-(4-(trans-4-alkylcyclohexyl)phenyl))benzoates can be prepared.

3,4,5-trifluorophenyl-(2,6-difluoro-4-(4-(trans-4-methylcyclohexyl)phenyl))benzoate, 3,4,5-trifluorophenyl-(2,6-difluoro-4-(4-(trans-4-ethylcyclohexyl)phenyl))benzoate, 3,4,5-trifluorophenyl-(2,6-difluoro-4-(4-(trans-4-propylcyclohexyl)phenyl))benzoate, 3,4,5-trifluorophenyl-(2,6-difluoro-4-(4-(trans-4-butylcyclohexyl)phenyl))benzoate, 3,4,5-trifluorophenyl-(2,6-difluoro-4-(4-(trans-4-pentylcyclohexyl)phenyl))benzoate, 3,4,5-trifluorophenyl-(2,6-difluoro-4-(4-(trans-4-hexylcyclohexyl)phenyl))benzoate, 3,4,5-trifluorophenyl-(2,6-difluoro-4-(4-(trans-4-heptylcyclohexyl)phenyl))benzoate, 3,4,5-trifluorophenyl-(2,6-difluoro-4-(4-(trans-4-octylcyclohexyl)phenyl))benzoate, 3,4,5-trifluorophenyl-(2,6-difluoro-4-(4-(trans-4-nonylcyclohexyl)phenyl))benzoate, and 3,4,5-trifluorophenyl-(2,6-difluoro-4-(4-(trans-4-decylcyclohexyl)phenyl))benzoate.

Example 9

Preparation of 3,4,5-Trifluorophenyl-(2-fluoro-4-(4-(2-(trans-4-propylcyclohexyl)ethyl)phenyl))benzoate (the Compound of Formula (1) wherein $R_1=C_3H_7$, m=n=1, A is a 1,4-Cyclohexylene Group, B is a 1, 4-Phenylene Group, $Z_1=5—CH_2CH_2—$ and $Z_2$ is a Covalent Bond and X=H)

In a 200 ml three-necked flask equipped with a stirrer, a thermometer and a condenser, 8 g (22.9 mmol) of 2-fluoro-4-(4-(2-(trans-4-propylcyclohexyl)ethyl)phenyl) benzonitrile and 2.3 g (57.3 mmol) of sodium hydroxide were dissolved under heat in 50 ml of ethylene glycol and the mixture was stirred for 5 hours while maintaining at 180° C. After the mixture was cooled down to room temperature, 30 ml of water and 15 ml of a 6N aqueous hydrochloric acid solution were added and the precipitated crystalline product was separated by filtration. The filtered product was repeatedly washed with water, dried and recrystallized from toluene to give 7.3 g of a colorless crystalline product which was 2-fluoro-4-(4-(2-(trans-4-propylcyclohexyl)ethyl)phenyl) benzoic acid.

In a 200 ml Kjeldahl flask, 7.3 g (19.9 mmol) of 2-fluoro-4-(4-(2-(trans-4-propylcyclohexyl)ethyl)phenyl)benzoic acid were dissolved in 50 ml of toluene and 0.1 g of pyridine was added. Then, 3.1 g (25.9 mmol) of thionyl chloride were added dropwise at room temperature while stirring. After the dropwise addition, the reaction was carried out for 2 hours by heating the mixture to 60° C. on a hot bath and maintaining it at the same temperature.

Unreacted thionyl chloride and toluene were distilled off from the reaction solution under reduced pressure by a tap aspirator and concentrated. Then, in a 100 ml three-necked flask equipped with a stirrer, a nitrogen gas inlet tube, a thermometer and a dropping funnel, 3.8 g (25.9 mmol) of 3,4,5-trifluorophenol and 1.7 g (21.9 mmol) of pyridine were dissolved in 30 ml of toluene under nitrogen atmosphere and the concentrate obtained in the above procedure was added dropwise over 5 minutes while stirring. After the dropwise addition, the reaction mixture was maintained at 60° C. on a hot bath and aged for 2 hours. 50 ml of water were added to the reaction solution to terminate the reaction. After the toluene layer was separated from the reaction solution, the aqueous layer was further extracted with 100 ml of diethyl ether. The combined organic layer was washed in turn with 100 ml of water, 50 ml of a 2N aqueous sodium hydroxide solution and water (100 ml×2), dried over anhydrous magnesium sulfate and concentrated to give 6.7 g of the reaction product. The reaction product was purified by a silica gel column chromatography using toluene as a developing solvent and recrystallized from toluene to give 3.7 g of a colorless crystalline product which was 3,4,5-trifluorophenyl-(2-fluoro-4-(4-(2-(trans-4-propylcyclohexyl)ethyl)phenyl))benzoate.

Following the above procedure and using 2-fluoro-4-(4-(2-(trans-4-alkylcyclohexyl)ethyl)phenyl)benzonitriles having different alkyl groups instead of 2-fluoro-4-(4-(2-(trans- 4-propylcyclohexyl)ethyl)phenyl)benzonitrile, the following 3,4,5-trifluorophenyl-(2-fluoro-4-(4-(2-(trans-4-alkylcyclohexyl)ethyl)phenyl))benzoates can be prepared. 3,4,5-trifluorophenyl-(2-fluoro-4-(4-(2-(trans-4-methylcyclohexyl)ethyl)phenyl))benzoate, 3,4,5-trifluorophenyl-(2-fluoro-4-(4-(2-(trans-4-ethylcyclohexyl)ethyl)phenyl))benzoate, 3,4,5-trifluorophenyl-(2-fluoro-4-(4-(2-(trans-4-butylcyclohexyl)ethyl)phenyl))benzoate, 3,4,5-trifluorophenyl-(2-fluoro-4-(4-(2-(trans-4-pentylcyclohexyl)ethyl)phenyl))benzoate, 3,4,5-trifluorophenyl-(2-fluoro-4-(4-(2-(trans-4-hexylcyclohexyl)ethyl)phenyl))benzoate, 3,4,5-trifluorophenyl-(2-fluoro-4-(4-(2-(trans-4-heptylcyclohexyl)ethyl)phenyl))benzoate, 3,4,5-trifluorophenyl-(2-fluoro-4-(4-(2-(trans-4-octylcyclohexyl)ethyl)phenyl))benzoate, 3,4,5-trifluorophenyl-(2-fluoro-4-(4-(2-(trans-4-nonylcyclohexyl)ethyl)phenyl))benzoate, and 3,4,5-trifluorophenyl-(2-fluoro-4-(4-(2-(trans-4-decylcyclohexyl)ethyl)phenyl))benzoate.

Further, following the above procedure and using 2,6-difluoro-4-(4-(2-(trans-4-alkylcyclohexyl)ethyl)phenyl) benzonitriles having different alkyl groups instead of 2-fluoro-4-(4-(2-(trans-4-propylcyclohexyl)ethyl)phenyl) benzonitrile, the following 3,4,5-trifluorophenyl-(2,6-difluoro-4-(4-(2-(trans-4-alkylcyclohexyl)ethyl)phenyl)) benzoates can be prepared.

3,4,5-trifluorophenyl-(2,6-difluoro-4-(4-(2-(trans-4-methylcyclohexyl)ethyl)phenyl))benzoate, 3,4,5-trifluorophenyl-(2,6-difluoro-4-(4-(2-(trans-4-ethylcyclohexyl)ethyl)phenyl))benzoate, 3,4,5-trifluorophenyl-(2,6-difluoro-4-(4-(2-(trans-4-propylcyclohexyl)ethyl)phenyl))benzoate, 3,4,5-trifluorophenyl-(2,6-difluoro-4-(4-(2-(trans-4-butylcyclohexyl)ethyl)phenyl))benzoate, 3,4,5-trifluorophenyl-(2,6-difluoro-4-(4-(2-(trans-4-pentylcyclohexyl)ethyl)phenyl))benzoate, 3,4,5-trifluorophenyl-(2,6-difluoro-4-(4-(2-(trans-4-hexylcyclohexyl)ethyl)phenyl))benzoate, 3,4,5-trifluorophenyl-(2,6-difluoro-4-(4-(2-(trans-4-heptylcyclohexyl)ethyl)phenyl))benzoate, 3,4,5-trifluorophenyl-(2,6-difluoro-4-(4-(2-(trans-4-octylcyclohexyl)ethyl)phenyl))benzoate, 3,4,5-trifluorophenyl-(2,6-difluoro-4-(4-(2-(trans-4-nonylcyclohexyl)ethyl)phenyl))benzoate, and 3,4,5-trifluorophenyl-(2,6-difluoro-4-(4-(2-(trans-4-decylcyclohexyl)ethyl)phenyl))benzoate.

Example 10 (Use Example 1)

A nematic liquid crystal composed of a liquid crystal composition having the following formulation has a clearing point(Cp) of 72.4° C.

4-(trans-4-propylcyclohexyl)benzonitrile 24%
4-(trans-4-pentylcyclohexyl)benzonitrile 36%
4-(trans-4-heptylcyclohexyl)benzonitrile 25%
4-(4-propylphenyl)benzonitrile 15%

(All % are by weight. The same will be applied to the following examples.)

This liquid crystal composition was sealed into a TN cell (a twisted nematic cell) with a cell thickness of 9 μm, which had an operating threshold voltage ($V_{th}$) of 1.78 V, a dielectric anisotropy (Δ∈) of +11.0, an optical anisotropy (Δn) of 0.137 and a viscosity at 20° C. ($\eta_{20}$) of 27.0 cP.

With 85 parts of said liquid crystal composition as a mother liquid crystal were mixed 15 parts of 3,4,5-trifluorophenyl(2-fluoro-4-(trans-4-propylcyclohexyl)) benzoate and the mixture was measured for its physical properties, with the following results. Cp: 70.3° C., $V_{th}$:1.45 V, Δ∈: 13.3, on: 0.133, and $\eta_{20}$: 32.8 cP. When this composition was allowed to stand in a freezer at −20° C. for 20 days, no precipitation of crystals was observed.

Example 11 (Use Example 2)

With 85 parts of the liquid crystal composition shown in Use Example 1 as a mother liquid crystal was mixed 15 parts of 3,4,5-trifluorophenyl(2-fluoro-4-(trans-4-pentylcyclohexyl))benzoate and the mixture was measured for its physical properties, with the following results. Cp: 71.4° C., $V_{th}$: 1.47 V, Δ∈: 12.9, Δn: 0.133, and $\eta_{20}$: 32.5 cP. When this composition was allowed to stand in a freezer at −20° C. for 20 days, no precipitation of crystals was observed.

In addition, the following Composition Examples (Examples 12–24) are given as a nematic liquid crystal composition containing the present compound. In these Examples, the compounds used in the compositions are shown in terms of the abbreviations as defined below. More specifically, the left terminal groups are shown with s, sO, sOt, Vs and sVt, the linking groups with 2, E, T and V, the ring structures with B, B(F), B(F,F), H and Py, and the right terminal groups with F, CL, C, OCF3, OCF2H, w, Ow, EMe, wV and wVx.

| Left Terminal Group | Symbol |
|---|---|
| $C_sH_{2s+1}-$ | s- |
| $C_sH_{2s+1}O-$ | sO— |
| $C_sH_{2s+1}OC_tH_{2t}-$ | sOt- |
| $H_2C=CHC_sH_{2s}-$ | Vs- |
| $C_sH_{2s+1}CH=CHC_tH_{2t}-$ | sVt- |

| Linking Group | Symbol |
|---|---|
| $-CH_2CH_2-$ | 2 |
| $-COO-$ | E |
| $-C\equiv C-$ | T |
| $-C=C-$ | V |

| Ring Structure | Symbol |
|---|---|
| 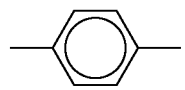 | B |
| 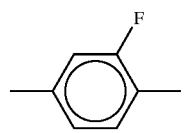 | B(F) |
| 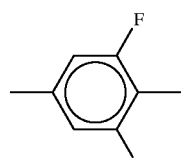 | B (F, F) |

-continued

| | |
|---|---|
| (cyclohexane structure) | H |
| (pyridine structure) | Py |

| Right Terminal Group | Symbol |
|---|---|
| —F | —F |
| —Cl | -CL |
| —CN | —C |
| —OCF$_3$ | —OCF3 |
| —OCF$_2$H | —OCF2H |
| —C$_w$H$_{2w+1}$ | -w |
| —OC$_w$H$_{2w+1}$ | —Ow |
| —COOCH$_3$ | -EMe |
| —C$_w$H$_{2w}$CH=CH$_2$ | -wV |
| —C$_w$H$_{2w}$CH=CHC$_x$H$_{2x+1}$ | -wVx |

Example 12

| | |
|---|---|
| 2-HB (E) EB (F, F)—F | 7.0% |
| 3-HB (F) EB (F, F)—F | 5.0% |
| 5-HB (F) EB (F, F)—F | 8.0% |
| 7-HB (F)—F | 9.0% |
| 2-HHB (F)—F | 11.0% |
| 3-HHB (F)—F | 11.0% |
| 5-HHB (F)—F | 11.0% |
| 2-H2HB (F)—F | 7.0% |
| 3-H2HB (F)—F | 7.0% |
| 5-H2HB (F)—F | 14.0% |
| 2-HBB (F)—F | 4.0% |
| 3-HBB (F)—F | 2.0% |
| 5-HBB (F)—F | 4.0% |

Cρ = 74.2 [° C.]
η = 27.7 [cP]
Δn = 0.097
Δε = 8.5
V$_{th}$ = 1.46 [V]

Example 13

| | |
|---|---|
| 2-HB (F) EB (F, F)—F | 5.0% |
| 5-HB (F) EB (F, F)—F | 5.0% |
| 5-HB—CL | 10.0% |
| 2-HBB (F)—F | 5.0% |
| 3-HBB (F)—F | 5.0% |
| 5-HBB (F)—F | 10.0% |
| 4-H2BB (F)—F | 5.0% |
| 5-H2BB (F)—F | 5.0% |
| 2-HHB—CL | 5.0% |
| 4-HHB—CL | 10.0% |
| 5-HHB—CL | 5.0% |
| 3-HBB (F, F)—F | 10.0% |
| 5-HBB (F, F)—F | 10.0% |
| 3-HB (F) VB-2 | 5.0% |
| 3-HB (F) VB-3 | 5.0% |

Cρ = 103.4 [° C.]
η = 29.3 [cP]
Δn = 0.139
Δε = 7.1
V$_{th}$ = 2.05 [V]

Example 14

| | |
|---|---|
| 5-HB (F) EB (F, F)—F | 8.0% |
| 5-H2B (F)—F | 10.0% |
| 2-HHB (F)—F | 10.0% |
| 3-HHB (F)—F | 10.0% |
| 5-HHB (F)—F | 10.0% |
| 2-H2HB (F)—F | 4.0% |
| 3-H2HB (F)—F | 2.0% |
| 5-H2HB (F)—F | 4.0% |
| 3-H2HB (F, F)—F | 6.0% |
| 4-H2HB (F, F)—F | 5.0% |
| 5-H2HB (F, F)—F | 5.0% |
| 3-HHB (F, F)—F | 8.0% |
| 3-HH2B (F, F)—F | 8.0% |
| 5-HH2B (F, F)—F | 7.0% |
| 1O1-HBBH-3 | 3.0% |

Cρ = 85.1 [° C.]
η = 24.2 [cP]
Δn = 0.078
Δε = 7.2
V$_{th}$ = 1.81 [V]

Example 15

| | |
|---|---|
| 5-HB (F, F) EB (F, F)—F | 5.0% |
| 2-HHB (F)—F | 10.0% |
| 3-HHB (F)—F | 10.0% |
| 5-HHB (F)—F | 10.0% |
| 2-HBB (F)—F | 5.0% |
| 3-HBB (F)—F | 5.0% |
| 5-HBB (F)—F | 10.0% |
| 3-HHB (F, F)—F | 7.0% |
| 5-HHB (F, F)—F | 4.0% |
| 3-HH2B (F, F)—F | 9.0% |
| 5-HH2B (F, F)—F | 9.0% |
| 5-H2HB (F, F)—F | 5.0% |
| 5-HHEBB—F | 3.0% |
| 3-HB—O2 | 5.0% |
| 3-HHB—O1 | 3.0% |

Cρ = 98.6 [° C.]
η = 26.8 [cP]
Δn = 0.095
Δε = 7.3
V$_{th}$ = 1.98 [V]

Example 16

| | |
|---|---|
| 3-HHB (F) EB (F, F)—F | 5.0% |
| 5-HEB—F | 2.5% |
| 7-HEB—F | 2.5% |
| 2-HHB (F)—F | 8.0% |
| 3-HHB (F)—F | 8.0% |
| 5-HHB (F)—F | 8.0% |
| 2-HBB (F)—F | 5.0% |
| 3-HBB (F)—F | 5.0% |
| 5-HBB (F)—F | 10.0% |
| 3-H2HB (F, F)—F | 10.0% |
| 3-HHB (F, F)—F | 10.0% |
| 3-HH2B (F, F)—F | 12.0% |
| 5-HH2B (F, F)—F | 10.0% |
| 3-HBB—F | 4.0% |

Cρ = 93.5 [° C.]
η = 27.8 [cP]
Δn = 0.095
Δε = 7.4
V$_{th}$ = 1.50 [V]

Example 17

| | |
|---|---|
| 3-HB (F) EB (F, F)—F | 4.0% |
| 5-HB (F) EB (F, F)—F | 10.0% |
| 3O1-BEB (F)—C | 12.0% |
| 5O1-BEB (F)—C | 4.0% |
| 1V2-BEB (F, F)—C | 10.0% |
| 5-HHEB—F | 5.0% |
| 3-HBEB—F | 6.0% |
| 3-HHB—F | 3.0% |
| 3-HB—O2 | 10.0% |
| 3-HH-4 | 5.0% |
| 3-HHB-1 | 8.0% |
| 3-HHB-3 | 6.0% |
| 3-HHB-O1 | 4.0% |
| 3-H2BTB-2 | 4.0% |
| 3-H2BTB-3 | 4.0% |
| 3-HB (F) TB-2 | 5.0% |

$C\rho = 93.7 \,[^\circ C.]$
$\eta = 37.3 \,[cP]$
$\Delta n = 0.132$
$\Delta\epsilon = 22.4$
$V_{th} = 1.12 \,[V]$

Example 18

| | |
|---|---|
| 2-HB (F) EB (F, F)—F | 6.0% |
| 3-HB (F) EB (F, F)—F | 4.0% |
| V2-HB—C | 12.0% |
| 1V2-HB—C | 12.0% |
| 3-HB—C | 7.0% |
| 3-HHB—C | 6.0% |
| 3-PyBB—F | 8.0% |
| 2-PyBH-3 | 6.0% |
| 3-PyBH-3 | 3.0% |
| 4-PyBB-3 | 3.0% |
| 3-HH-4 | 6.0% |
| 1O1-HH-3 | 5.0% |
| 2-BTB-1 | 3.8% |
| 1-BTB-6 | 7.4% |
| 4-BTB-4 | 3.8% |
| 3-HHB-1 | 4.0% |
| 3-HH—EMe | 3.0% |

$C\rho = 83.4 \,[^\circ C.]$
$\eta = 24.5 \,[cP]$
$\Delta n = 0.152$
$\Delta\epsilon = 9.2$
$V_{th} = 1.71 \,[V]$

Example 19

| | |
|---|---|
| 2-HB(F)EB(F, F)-F | 10.0% |
| V2-HB-C | 11.0% |
| 1V2-HB-C | 10.0% |
| 1O1-HB-C | 10.0% |
| 2-HB-C | 5.0% |
| 3-HB-C | 5.0% |
| 3-HH-4 | 12.0% |
| 2-BTB-O1 | 4.0% |
| 3-BTB-O1 | 4.0% |
| 4-BTB-O1 | 4.0% |
| 4-BTB-O2 | 4.0% |
| 5-BTB-O1 | 4.0% |
| 2-HHB-C | 5.0% |
| 3-HHB-C | 5.0% |
| 3-HHB-F | 4.0% |
| 3-HHB-1 | 3.0% |

$Cp = 67.1 \,[^\circ C.]$
$\eta = 21.5 \,[cP]$
$\Delta n = 0.139$
$\Delta\epsilon = 10.2$
$V_{th} = 1.43 \,[V]$

Example 20

| | |
|---|---|
| 3-HB (F) EB (F, F)—F | 5.0% |
| 5-HB (F) FB (F, F)—F | 5.0% |
| 2-BB—C | 12.0% |
| 3-HB (F)—C | 12.0% |
| 5-HB (F)—C | 8.0% |
| 2-BEB—C | 12.0% |
| 2-HHB (F)—C | 6.0% |
| 3-HHB (F)—C | 5.0% |
| 2-HHB—C | 3.0% |
| 3-HHB—C | 3.0% |
| 3-PyB-2 | 4.0% |
| 6-PyB—O4 | 4.0% |
| 3-HB—O2 | 7.0% |
| 3-HB (F) VB-2 | 7.0% |
| 3-HB (F) VB-3 | 7.0% |

$C\rho = 76.0 \,[^\circ C.]$
$\eta = 42.1 \,[cP]$
$\Delta n = 0.158$
$\Delta\epsilon = 16.1$
$V_{th} = 1.14 \,[V]$

Example 21

| | |
|---|---|
| 5-HB (F) EB (F, F)—F | 5.0% |
| 3-DB—C | 10.0% |
| 4-DB—C | 10.0% |
| 2-BEB—C | 12.0% |
| 3-PyB (F)—F | 6.0% |
| 3-HEB—O4 | 6.0% |
| 4-HEB—O2 | 4.6% |
| 5-HEB—O1 | 4.6% |
| 3-HEB—O2 | 3.8% |
| 5-HEB—O2 | 3.0% |
| 5-HEB-1 | 3.0% |
| 1O-BEB-2 | 3.0% |
| 3-HHB-1 | 10.0% |
| 3-HHEBB—C | 3.0% |
| 3-HBEBB—C | 3.0% |
| 5-PyB—F | 3.0% |
| 3-HEBEB-1 | 5.0% |
| 3-HEBEB—F | 5.0% |

$C\rho = 79.5 \,[^\circ C.]$
$\eta = 46.4 \,[cP]$
$\Delta n = 0.125$
$\Delta\epsilon = 12.4$
$V_{th} = 1.31 \,[V]$

Example 22

| | |
|---|---|
| 2-HB (F) EB (F, F)—F | 5.0% |
| 5-HB (F) EB (F, F)—F | 5.0% |
| 7-HB-F | 11.0% |
| 3-HHB—OCF3 | 12.0% |
| 5-HHB—OCF3 | 8.0% |
| 2-H2HB—OCF3 | 5.0% |
| 5-H2HB—OCF 3 | 5.0% |
| 3-HH2B (F)—F | 10.0% |
| 5-HH2B (F)—F | 10.0% |
| 3-H2HB (F, F)—F | 6.0% |
| 4-H2HB (F, F)—F | 5.0% |

-continued

| | |
|---|---|
| 5-H2HB (F, F)—F | 5.0% |
| 3-HBB (F, F)—F | 8.0% |
| 3-HH2B (F, F)—F | 5.0% |

Cp = 86.1 [° C.]
η = 20.6 [cP]
Δn = 0.084
Δε = 7.3
$V_{th}$ = 1.81 [V]

Example 23

| | |
|---|---|
| 5-HB (F, F) EB (F, F)—F | 5.0% |
| 5-HB—F | 6.0% |
| 7-HB—F | 6.0% |
| 2-HHB—OCF3 | 8.0% |
| 3-HHB—OCF3 | 7.0% |
| 5-HHB—OCF3 | 5.0% |
| 3-HHB—OCF2H | 5.0% |
| 5-HHB—OCF2H | 4.0% |
| 3-HHB (F, F)—OCF2H | 7.0% |
| 5-HHB (F, F)—OCF2H | 11.0% |
| 3-HH2B (F)—F | 11.0% |
| 5-HH2B (F)—F | 11.0% |
| 3-HHEB (F)—F | 5.0% |
| 3-HHEB (F)—F | 5.0% |
| 3-HB (F, F) B (F)—F | 2.0% |
| 3-HHEB—OCF3 | 2.0% |

Cp = 100.9 [° C.]
η = 23.6 [cP]
Δn = 0.084
Δε = 6.4
$V_{th}$ = 2.20 [V]

Example 24

| | |
|---|---|
| 5-HB (F) EB (F, F)—F | 5.0% |
| 3-HB (F)—C | 5.0% |
| 3O1-BEB (F)—C | 10.0% |
| V-HB—C | 10.0% |
| 1V-HB—C | 10.0% |
| 2-BTB—O1 | 10.0% |
| 3-HB—O2 | 10.0% |
| V2-HH-3 | 5.0% |
| V-HH-4 | 5.0% |
| V-HHB-1 | 10.0% |
| 1V2-HBB-2 | 10.0% |
| 3-HHB-1 | 10.0% |

Cp = 69.4 [° C.]
η = 17.2 [cP]
Δn = 0.130
Δε = 8.8
$V_{th}$ = 1.55 [V]

Comparative Example

A nematic liquid crystal composed of a liquid crystal composition having the following formulation has a clearing point (Cp) of 52.3° C.

4-(trans-4-propylcyclohexyl)benzonitrile 30%
4-(trans-4-pentylcyclohexyl)benzonitrile 40%
4-(trans-4-heptylcyclohexyl)benzonitrile 30%

(% is by weight.)

This liquid crystal composition was sealed into a TN cell (a twisted nematic cell) with a cell thickness of 9 μm, which had an operating threshold voltage ($V_{th}$) of 1.60 V, a dielectric anisotropy (Δε) of +10.7, an optical anisotropy (Δn) of 0.119 and a viscosity at 20° C. ($η_{20}$) of 21.7 cP.

With 85 parts of said liquid crystal composition as a mother liquid crystal were mixed 15 parts of a mixture of 3,4,5-trifluorophenyl(2-fluoro-4-(trans-4-propyl-cyclohexyl))benzoate with 3,4,5-trifluorophenyl(2-fluoro-4-(trans-4-pentylcyclohexyl))benzoate in an equal amount to prepare a new composition. For comparison, a new composition was similarly prepared from the compounds represented by formula (c) (U.S. Pat. No. 5,032,313) as shown in the BACKGROUND ART, which have the same alkyl chain length as those shown in the above Example. Each of these compositions was measured for its physical properties and the results were compared. In regard to compatibility, the compositions as prepared were allowed to stand in a freezer at −20° C. and compared by observing the precipitation of crystals. The results of the measured physical properties and the test results on compatibility are shown in Table 1.

TABLE 1

| Compounds | Cp (° C.) | Δε | Δn | $V_{th}$ | $η_{20}$ (cP) | Compatibility (days)* |
|---|---|---|---|---|---|---|
| mother liquid crystal | 52.3 | 10.7 | 0.119 | 1.60 | 21.7 | |
| 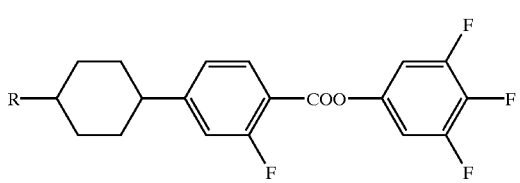 | 52.5 | 13.5 | 0.114 | 1.19 | 28.3 | >20 |
| 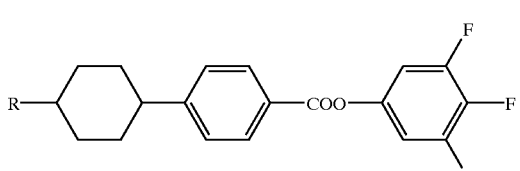 | 54.6 | 13.1 | 0.116 | 1.28 | 28.1 | 3 |

TABLE 1-continued

| Compounds | Cp (° C.) | Δε | Δn | $V_{th}$ | $\eta_{20}$ (cP) | Compatibility (days)* |
|---|---|---|---|---|---|---|

*The number of days ranging from the day when the composition was allowed to stand in a freezer at −20° C., up to the day when precipitation of crystals was observed in the composition As can be seen from Table 1, it was found that the present phenylbenzoate derivatives show an equal level of viscosity as compared with the prior art compounds, while they show a lower value of threshold voltage ($V_{th}$) by approximately 10% as compared with the prior art compounds. With regard to compatibility, precipitation of crystals was observed in the compositions prepared from the prior art compounds on the 3rd day after the composition was allowed to stand, whereas no precipitation of crystals was observed in the compositions prepared from the present compounds even over 20 days.

As can be seen from the above results, the present phenylbenzoate derivatives are novel liquid crystalline compounds which have a relatively lower viscosity and a higher dielectric anisotropy together with a lower optical anisotropy, and have an excellent compatibility, in particular, a low temperature compatibility, with other known liquid crystalline compounds. By using the present compounds in a liquid crystal composition, a threshold voltage can be effectively reduced with a less noticeable increase in viscosity to provide a liquid crystal composition having improved characteristics.

INDUSTRIAL APPLICABILITY

The phenylbenzoate derivatives of the present invention have a very high dielectric anisotropy (Δε) but a lower optical anisotropy and also they have excellent characteristics as a liquid crystal material for TN drive, especially, a low voltage TN of a first-minimum system and for a low voltage TFT. Further, the phenylbenzoate derivatives of the invention have a good compatibility with many other liquid crystalline compounds including the ester, Schiff base, biphenyl, phenylcyclohexane, bicyclohexane, heterocyclic and fluorine types, in particular, good compatibility with them at a low temperature. Furthermore, the addition of the present compounds as an ingredient of the liquid crystal composition can drastically reduce a driving voltage, while inhibiting an increase in viscosity and a reduction in nematic liquid crystal phase temperature range.

What is claimed is:

1. A phenylbenzoate derivative represented by formula I-b-1:

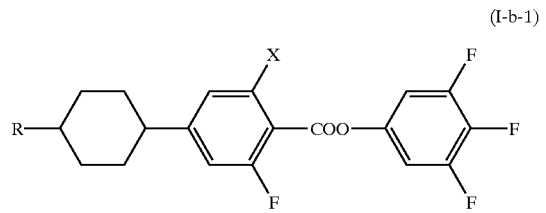

(I-b-1)

wherein R is a hydrogen atom or a straight or branched-chain alkyl group of 1–10 carbons, one or two non-adjacent $CH_2$ groups of which may be replaced by an oxygen atom or —CH=CH—group, and X is a hydrogen atom or a halogen atom.

2. A phenylbenzoate derivative represented by formula I-b-1 as claimed in claim 1, wherein R is a hydrogen atom or a straight or branched-chain alkyl group of 1–9 carbons, one or two non-adjacent $CH_2$ groups of which may be replaced by an oxygen atom or —CH=CH-group, and X is a hydrogen atom or a halogen atom.

3. A liquid crystal composition comprising at least two different liquid crystal compounds, wherein at least one of said two liquid crystal compounds is a phenylbenzoate derivative of claim 1.

4. A liquid crystal composition comprising at least two different liquid crystal compounds, wherein at least one of said two liquid crystal compounds is a phenylbenzoate derivative of claim 2.

5. A liquid crystal display element comprising a liquid crystal composition, said composition comprising at least two different liquid crystal compounds, at least one of said two liquid crystal compounds being a phenylbenzoate derivative according to claim 1.

6. A liquid crystal display element comprising a liquid crystal composition, said composition comprising at least two different liquid crystal compounds, at least one of said two liquid crystal compounds being a phenylbenzoate derivative according to claim 2.

7. A liquid crystal composition which comprises as a first component at least one of the phenylbenzoate derivatives as claimed in claim 1 and as a second component one or more compounds selected from the group consisting of the compounds of formulae (2), (3) and (4)

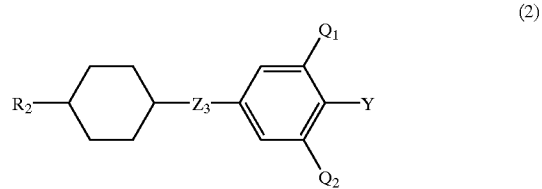

(2)

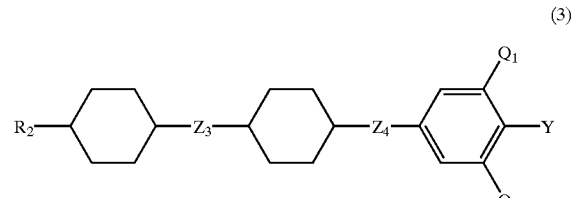

(3)

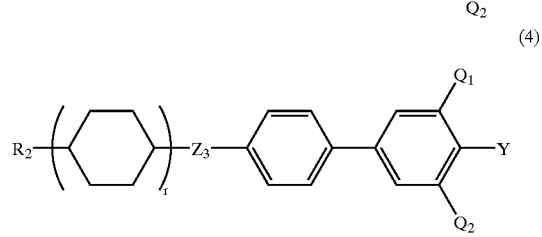

(4)

wherein $R_2$ is an alkyl group of 1–10 carbons, Y is F or Cl, $Q_1$ and $Q_2$ each independently represent H or F, r is 1 or 2, and $Z_3$ and $Z_4$ each independently represent —$CH_2CH_2$— or a covalent bond.

8. A liquid crystal composition which comprises as a first component at least one of the phenylbenzoate derivatives as claimed in claim 1 and as a second component one or more compounds selected from the group consisting of the compounds of formulae (5), (6), (7), (8) and (9)

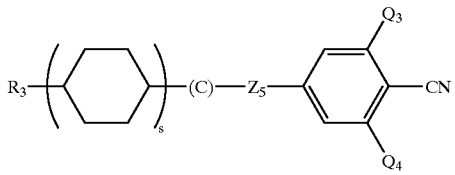
(5)

wherein $R_3$ is an alkyl group of 1–10 carbons or an alkenyl group of 2–10 carbons and in any case methylene group (—$CH_2$—) may be replaced by an oxygen atom (—O—), but two or more methylene groups are not consecutively replaced by an oxygen atom, $Z_5$ is —$CH_2CH_2$—, —COO— or a covalent bond, $Q_3$ and $Q_4$ represent H or F, C stands for a cyclohexane ring, a benzene ring or a 1,3-dioxane ring, and s is 0 or 1,

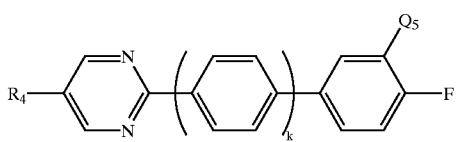
(6)

wherein $R_4$ is an alkyl group of 1–10 carbons, $Q_5$ represents H or F, and k is 0 or 1,

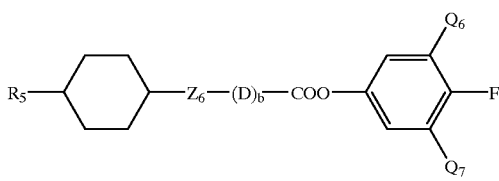
(7)

wherein $R_5$ is an alkyl group of 1–10 carbons, D stands for a cyclohexane ring or a benzene ring, $Q_6$ and $Q_7$ each independently represent H or F, $Z_6$ is —COO— or a covalent bond, and h is 0 or 1,

(8)

wherein $R_6$ and $R_7$ each independently represent an alkyl, alkyloxy or alkyloxymethyl group of 1–10 carbons, E stands for a cyclohexane ring, a pyrimidine ring or a benzene ring, F stands for a cyclohexane ring or a benzene ring, and $Z_7$ is —C≡C—, —COO—, —$CH_2CH_2$— or a covalent bond,

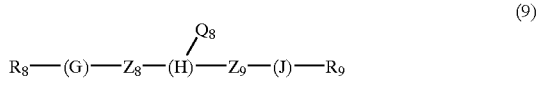
(9)

wherein $R_8$ is an alkyl or alkyloxy group of 1–10 carbons, $R_9$ is an alkyl, alkyloxy or alkyloxymethyl group of 1–10 carbons, G stands for a cyclohexane ring or a pyrimidine ring, H and J each independently represent a cyclohexane ring or a benzene ring, $Z_8$ is —COO—, —$CH_2CH_2$— or a covalent bond, $Z_9$ is —C≡C—, —COO— or a covalent bond, and $Q_8$ is H or F.

9. A liquid crystal display element comprising a liquid crystal composition as claimed in claim 7.

10. A liquid crystal display element comprising a liquid crystal composition as claimed in claim 8.

11. A phenylbenzoate derivative as claimed in claim 1, wherein X is a fluorine atom.

12. A phenylbenzoate derivative as claimed in claim 2 wherein X is a fluorine atom.

13. A liquid crystal composition as claimed in claim 3, wherein X is a fluorine atom.

14. A liquid crystal composition as claimed in claim 4, wherein X is a fluorine atom.

15. A liquid crystal display element as claimed in claim 5, wherein X is a fluorine atom.

16. A liquid crystal display element as claimed in claim 6, wherein X is a fluorine atom.

* * * * *